(12) United States Patent
Chen et al.

(10) Patent No.: US 8,129,434 B2
(45) Date of Patent: Mar. 6, 2012

(54) BENZYLPHENYL CYCLOHEXANE DERIVATIVES AND METHODS OF USE

(75) Inventors: Yuanwei Chen, North Haven, CT (US); Kun Peng, Shanghai (CN); Lili Zhang, Shanghai (CN); Binhua Lv, Shanghai (CN); Baihua Xu, Shanghai (CN); Jiajia Dong, Shanghai (CN); Jiyan Du, Shanghai (CN); Yan Feng, Shanghai (CN); Ge Xu, Shanghai (CN); Vasanthakumar Rajappan, San Diego, CA (US); Brian Seed, Derry, NH (US)

(73) Assignee: Theracos, Inc., Sunnyvale, CA (US)

( * ) Notice: Subject to any disclaimer, the term of this patent is extended or adjusted under 35 U.S.C. 154(b) by 517 days.

(21) Appl. No.: 12/333,190

(22) Filed: Dec. 11, 2008

(65) Prior Publication Data

US 2009/0156516 A1   Jun. 18, 2009

Related U.S. Application Data

(60) Provisional application No. 61/013,517, filed on Dec. 13, 2007.

(51) Int. Cl.
A61K 31/015 (2006.01)
C07C 15/12 (2006.01)
(52) U.S. Cl. .......................... 514/764; 585/25
(58) Field of Classification Search .............. 585/25
See application file for complete search history.

(56) References Cited

U.S. PATENT DOCUMENTS

| | | |
|---|---|---|
| 5,663,377 A | 9/1997 | Curley, Jr. et al. |
| 6,069,238 A | 5/2000 | Hitchcock et al. |
| 6,414,126 B1 | 7/2002 | Ellsworth et al. |
| 6,515,117 B2 | 2/2003 | Ellsworth et al. |
| 6,555,519 B2 | 4/2003 | Washburn |
| 6,683,056 B2 | 1/2004 | Washburn et al. |
| 6,774,112 B2 | 8/2004 | Gougoutas |
| 6,936,590 B2 | 8/2005 | Washburn et al. |
| 7,022,725 B2 | 4/2006 | Momose et al. |
| 7,094,763 B2 | 8/2006 | Rybczynski et al. |
| 7,371,732 B2 | 5/2008 | Eickelmann et al. |
| 7,375,090 B2 | 5/2008 | Himmelsbach et al. |
| 7,375,213 B2 | 5/2008 | Deshpande et al. |
| 7,393,836 B2 | 7/2008 | Eckhardt et al. |
| 7,417,032 B2 | 8/2008 | Eckhardt et al. |
| 7,419,959 B2 | 9/2008 | Eckhardt et al. |
| 7,838,498 B2 | 11/2010 | Chen et al. |
| 2002/0111315 A1 | 8/2002 | Washburn et al. |
| 2003/0064935 A1 | 4/2003 | Gougoutas |
| 2003/0087843 A1 | 5/2003 | Washburn |
| 2003/0114390 A1 | 6/2003 | Washburn et al. |
| 2004/0138148 A1 | 7/2004 | Fushimi et al. |
| 2004/0138439 A1 | 7/2004 | Deshpande et al. |
| 2004/0259819 A1 | 12/2004 | Frick et al. |
| 2005/0014704 A1 | 1/2005 | Frick et al. |
| 2005/0032712 A1 | 2/2005 | Urbanski |
| 2005/0037980 A1 | 2/2005 | Rybczynski et al. |
| 2005/0187168 A1 | 8/2005 | Eickelmann et al. |
| 2005/0209166 A1 | 9/2005 | Eckhardt et al. |
| 2005/0209309 A1 | 9/2005 | Sato et al. |
| 2005/0233982 A1 | 10/2005 | Himmelsbach et al. |
| 2005/0233988 A1 | 10/2005 | Nomura et al. |
| 2006/0009400 A1 | 1/2006 | Eckhardt et al. |
| 2006/0019948 A1 | 1/2006 | Eckhardt et al. |
| 2006/0025349 A1 | 2/2006 | Eckhardt et al. |
| 2006/0035841 A1 | 2/2006 | Eckhardt et al. |
| 2006/0063722 A1 | 3/2006 | Washburn et al. |
| 2006/0074031 A1 | 4/2006 | Eckhardt et al. |
| 2006/0122126 A1 | 6/2006 | Imamura et al. |
| 2006/0142210 A1 | 6/2006 | Eckhardt et al. |
| 2006/0166899 A1 | 7/2006 | Teranishi et al. |
| 2006/0189548 A1 | 8/2006 | Himmelsbach et al. |
| 2006/0234953 A1 | 10/2006 | Himmelsbach et al. |
| 2006/0234954 A1 | 10/2006 | Urbanski |
| 2006/0235062 A1 | 10/2006 | Neogi et al. |
| 2006/0247179 A1 | 11/2006 | Fushimi et al. |
| 2006/0251728 A1 | 11/2006 | Himmelsbach et al. |
| 2006/0258749 A1 | 11/2006 | Eckhardt et al. |
| 2007/0004648 A1 | 1/2007 | Himmelsbach et al. |
| 2007/0027092 A1 | 2/2007 | Himmelsbach et al. |
| 2007/0049537 A1 | 3/2007 | Eckhardt et al. |
| 2007/0054867 A1 | 3/2007 | Eckhardt et al. |
| 2007/0072896 A1 | 3/2007 | Khan et al. |
| 2007/0161787 A1 | 7/2007 | Imamura et al. |
| 2007/0185197 A1 | 8/2007 | Fujikura et al. |
| 2007/0197450 A1 | 8/2007 | Fushimi et al. |
| 2007/0249544 A1 | 10/2007 | Himmelsbach et al. |
| 2007/0275907 A1 | 11/2007 | Chen et al. |

(Continued)

FOREIGN PATENT DOCUMENTS

| | | |
|---|---|---|
| CA | 2 539 032 A1 | 3/2005 |
| CA | 2 548 353 A1 | 7/2005 |
| EP | 1 783 110 A1 | 5/2007 |

(Continued)

OTHER PUBLICATIONS

International Search Report mailed on Feb. 13, 2009, for International Application No. PCT/US08/86472 filed on Dec. 11, 2008, 1 page Isaji, M., "Sodium-glucose cotransporter inhibitors for diabetes," *Current Opinion in Investigational Drugs*, 2007, vol. 8, No. 4, pp. 285-292.

*Primary Examiner* — Elli Peselev

(74) *Attorney, Agent, or Firm* — Kilpatrick Townsend & Stockton LLP

(57) ABSTRACT

Provided are compounds having an inhibitory effect on sodium-dependent glucose cotransporter SGLT. The invention also provides pharmaceutical compositions, methods of preparing the compounds, synthetic intermediates, and methods of using the compounds, independently or in combination with other therapeutic agents, for treating diseases and conditions which are affected by SGLT inhibition.

28 Claims, 5 Drawing Sheets

U.S. PATENT DOCUMENTS

| | | |
|---|---|---|
| 2008/0004336 A1 | 1/2008 | Gougoutas et al. |
| 2008/0027014 A1 | 1/2008 | Nomura et al. |
| 2008/0132563 A1 | 6/2008 | Kakinuma et al. |
| 2008/0139484 A1 | 6/2008 | Teranishi et al. |
| 2008/0318874 A1 | 12/2008 | Matsuoka et al. |
| 2009/0023913 A1 | 1/2009 | Eckhardt et al. |
| 2009/0118201 A1 | 5/2009 | Chen et al. |

FOREIGN PATENT DOCUMENTS

| | | |
|---|---|---|
| EP | 1 803 721 A1 | 7/2007 |
| EP | 1 852 439 A1 | 11/2007 |
| WO | WO 98/31697 A1 | 7/1998 |
| WO | WO 01/27128 A1 | 4/2001 |
| WO | WO 01/74834 A1 | 10/2001 |
| WO | WO 01/74835 A1 | 10/2001 |
| WO | WO 02/083066 A2 | 10/2002 |
| WO | WO 02/083066 A3 | 10/2002 |
| WO | WO 03/020737 A1 | 3/2003 |
| WO | WO 03/099836 A1 | 12/2003 |
| WO | WO 2004/063209 A2 | 7/2004 |
| WO | WO 2004/063209 A3 | 7/2004 |
| WO | WO 2005/021566 A2 | 3/2005 |
| WO | WO 2005/021566 A3 | 3/2005 |
| WO | WO 2005/063785 A2 | 7/2005 |
| WO | WO 2005/063785 A3 | 7/2005 |
| WO | WO 2005/085237 A1 | 9/2005 |
| WO | WO 2005/092877 A1 | 10/2005 |
| WO | WO 2006/002912 A1 | 1/2006 |
| WO | WO 2006/008038 A1 | 1/2006 |
| WO | WO 2006/010557 A1 | 2/2006 |
| WO | WO 2006/011469 A1 | 2/2006 |
| WO | WO 2006/018150 A1 | 2/2006 |
| WO | WO 2006/034489 A2 | 3/2006 |
| WO | WO 2006/034489 A3 | 3/2006 |
| WO | WO 2006/037537 A2 | 4/2006 |
| WO | WO 2006/037537 A3 | 4/2006 |
| WO | WO 2006/064033 A2 | 6/2006 |
| WO | WO 2006/064033 A3 | 6/2006 |
| WO | WO 2006/073197 A1 | 7/2006 |
| WO | WO 2006/080421 A1 | 8/2006 |
| WO | WO 2006/108842 A1 | 10/2006 |
| WO | WO 2006/110654 A1 | 10/2006 |
| WO | WO 2006/117359 A1 | 11/2006 |
| WO | WO 2006/117360 A1 | 11/2006 |
| WO | WO 2006/120208 A1 | 11/2006 |
| WO | WO 2007/000445 A1 | 1/2007 |
| WO | WO 2007/014894 A2 | 2/2007 |
| WO | WO 2007/014894 A3 | 2/2007 |
| WO | WO 2007/025943 A2 | 3/2007 |
| WO | WO 2007/025943 A3 | 3/2007 |
| WO | WO 2007/028814 A1 | 3/2007 |
| WO | WO 2007/114475 A1 | 10/2007 |
| WO | WO 2007/136116 A2 | 11/2007 |
| WO | WO 2007/136116 A3 | 11/2007 |
| WO | WO 2008/002824 A1 | 1/2008 |
| WO | WO 2009/026537 A1 | 2/2009 | the preparation of Grignard reagent

BENZYLPHENYL CYCLOHEXANE DERIVATIVES AND METHODS OF USE

CROSS-REFERENCE TO RELATED APPLICATION

This application claims the benefit of U.S. Provisional Application Ser. No. 61/013,517 filed Dec. 13, 2007, the disclosure of which is incorporated herein by reference.

STATEMENT AS TO RIGHTS TO INVENTIONS MADE UNDER FEDERALLY SPONSORED RESEARCH AND DEVELOPMENT

NOT APPLICABLE

BACKGROUND OF THE INVENTION

According to the World Health Organization, approximately 150 million people worldwide have diabetes mellitus. The two principal forms of diabetes are type 1 diabetes, in which the pancreas fails to produce insulin, and type 2 diabetes, in which the body fails to respond properly to the insulin produced (insulin resistance). Accounting for about 90% of all diabetes cases, type 2 diabetes is by far the most common. In both types of diabetes, the absence of insulin action or proper response to insulin results in elevated levels of serum glucose (hyperglycemia). Serious complications associated with diabetes include retinopathy (leading to visual impairment or blindness), cardiovascular disease, nephropathy, neuropathy, ulcers and diabetic foot disease.

Individuals with type 1 diabetes currently require insulin therapy. While in many cases type 2 diabetes can be managed with diet and exercise, drug intervention also frequently is required. Besides insulin, which is needed by about one-third of patients with type 2 diabetes, current antidiabetic therapies include biguanides (which decrease glucose production in the liver and increase sensitivity to insulin), sulfonylureas and meglitinides (which stimulate insulin production), alpha-glucosidase inhibitors (which slow starch absorption and glucose production), and thiazolidinediones (which increase insulin sensitivity). These medicines are often used in combination, and even then may not provide adequate glycemic control or may produce undesired side effects. Such side effects include lactic acidosis (biguanides), hypoglycemia (sulfonylureas), and edema and weight gain (thiazolidinediones). Therefore, new antidiabetic agents providing improved glycemic control and lacking these adverse effects are highly desired.

One promising target for therapeutic intervention in diabetes and related disorders is the glucose transport system of the kidneys. Cellular glucose transport is conducted by either facilitative ("passive") glucose transporters (GLUTs) or sodium-dependent ("active") glucose cotransporters (SGLTs). SGLT1 is found predominantly in the intestinal brush border, while SGLT2 is localized in the renal proximal tubule and is reportedly responsible for the majority of glucose reuptake by the kidneys. Recent studies suggest that inhibition of renal SGLT may be a useful approach to treating hyperglycemia by increasing the amount of glucose excreted in the urine (Arakawa K, et al., Br J Pharmacol 132:578-86, 2001; Oku A, et al., Diabetes 48:1794-1800, 1999). The potential of this therapeutic approach is further supported by recent findings that mutations in the SGLT2 gene occur in cases of familial renal glucosuria, an apparently benign syndrome characterized by urinary glucose excretion in the presence of normal serum glucose levels and the absence of general renal dysfunction or other disease (Santer R, et al., J Am Soc Nephrol 14:2873-82, 2003). Therefore, compounds which inhibit SGLT, particularly SGLT2, are promising candidates for use as antidiabetic drugs. Compounds previously described as useful for inhibiting SGLT include cyclohexane derivatives (such as those described in WO2006011469), C-glycoside derivatives (such as those described in U.S. Pat. No. 6,414,126, US20040138439, US20050209166, US20050233988, WO2005085237, U.S. Pat. No. 7,094,763, US20060009400, US20060019948, US20060035841, US20060122126 and WO2006108842), O-glycoside derivatives (such as those described in U.S. Pat. No. 6,683,056, US20050187168, US20060166899, US20060234954, US20060247179 and US20070185197), spiroketal-glycoside derivatives (described in WO2006080421), and thioglucopyranoside derivatives (such as those described in US20050209309 and WO2006073197).

BRIEF SUMMARY OF THE INVENTION

The present invention provides compounds having an inhibitory effect on sodium-dependent glucose cotransporter SGLT. The invention also provides pharmaceutical compositions, methods of preparing the compounds, synthetic intermediates, and methods of using the compounds, independently or in combination with other therapeutic agents, for treating diseases and conditions which are affected by SGLT inhibition.

DETAILED DESCRIPTION OF THE INVENTION

Definitions

Figure 1:
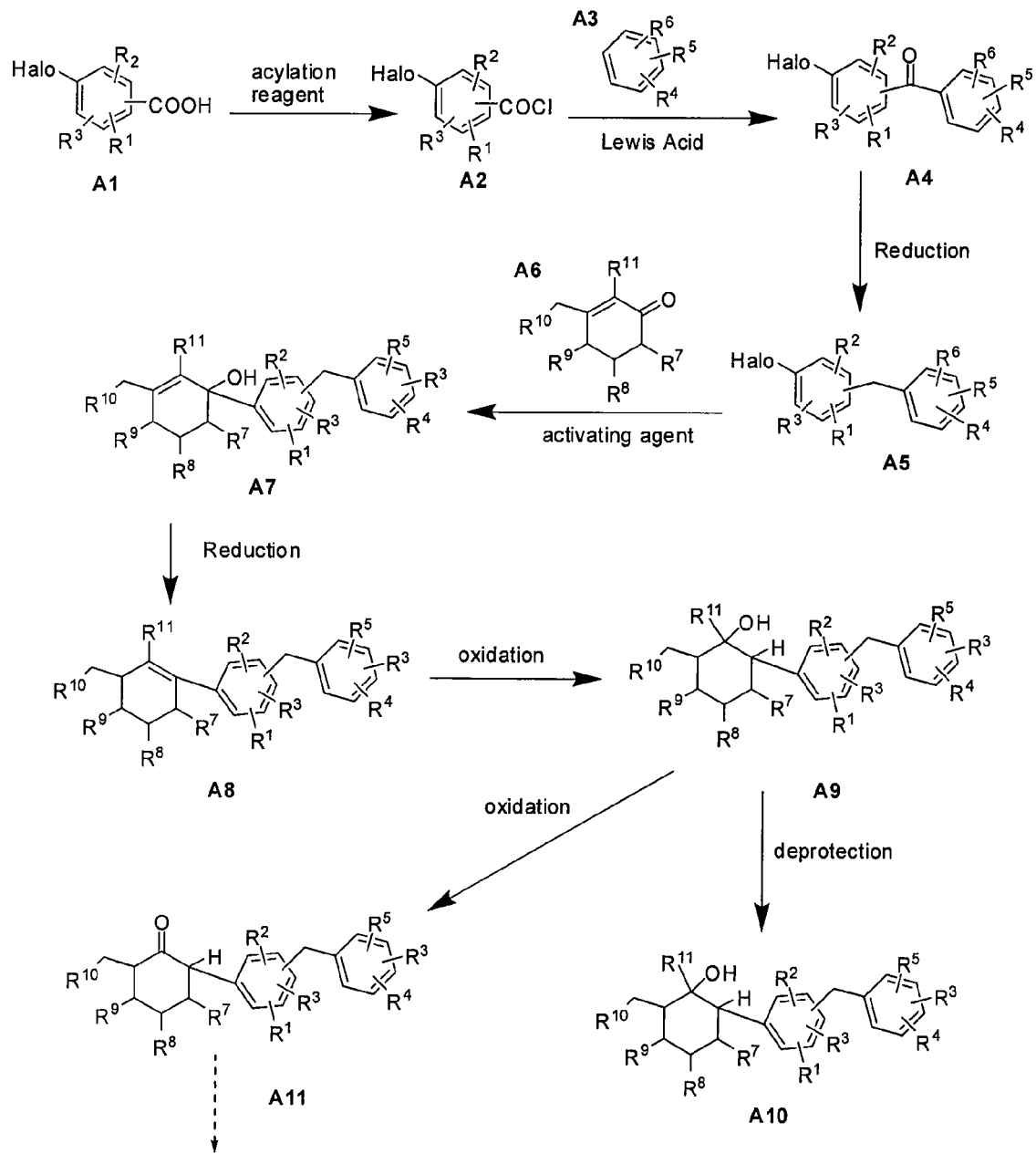
FIGS. 1-2 provide generic synthesis schemes for compounds of the invention.

As used herein, the term "halo" means a monovalent halogen radical or atom selected from fluoro, chloro, bromo and iodo. Preferred halo groups are fluoro, chloro and bromo.

As used herein, the term "suitable substituent" means a chemically and pharmaceutically acceptable group, i.e., a moiety that does not significantly interfere with the preparation of or negate the efficacy of the inventive compounds. Such suitable substituents may be routinely chosen by those skilled in the art. Suitable substituents may be selected from the group consisting of halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, $C_2$-$C_6$ alkynyl, $C_3$-$C_8$ cycloalkenyl, ($C_3$-$C_8$ cycloalkyl)$C_1$-$C_6$ alkyl, ($C_3$-$C_8$ cycloalkyl)$C_2$-$C_6$ alkenyl, ($C_3$-$C_8$ cycloalkyl)$C_1$-$C_6$ alkoxy, $C_3$-$C_7$ heterocycloalkyl, ($C_3$-$C_7$ heterocycloalkyl)$C_1$-$C_6$ alkyl, ($C_3$-$C_7$ heterocycloalkyl)$C_2$-$C_6$ alkenyl, ($C_3$-$C_7$ heterocycloalkyl)$C_1$-$C_6$ alkoxy, hydroxy, carboxy, oxo, sulfanyl, $C_1$-$C_6$ alkylsulfanyl, aryl, heteroaryl, aryloxy, heteroaryloxy, aralkyl, heteroaralkyl, aralkoxy, heteroaralkoxy, nitro, cyano, amino, $C_1$-$C_6$ alkylamino, di-($C_1$-$C_6$ alkyl)amino, carbamoyl, ($C_1$-$C_6$ alkyl)carbonyl, ($C_1$-$C_6$ alkoxy)carbonyl, ($C_1$-$C_6$ alkyl)aminocarbonyl, di-($C_1$-$C_6$ alkyl)aminocarbonyl, arylcarbonyl, aryloxycarbonyl, ($C_1$-$C_6$ alkyl)sulfonyl, and arylsulfonyl. The groups listed above as suitable substituents are as defined hereinafter except that a suitable substituent may not be further optionally substituted.

As used herein, unless otherwise indicated, the term "alkyl" alone or in combination refers to a monovalent saturated aliphatic hydrocarbon radical having the indicated number of carbon atoms. The radical may be a linear or branched chain and, where specified, optionally substituted with one to three suitable substituents as defined above. Illustrative examples of alkyl groups include, but are not limited to, methyl, ethyl, n-propyl, n-butyl, n-pentyl, n-hexyl, isopropyl, isobutyl, isopentyl, amyl, sec-butyl, tert-butyl, tert-pentyl, n-heptyl, n-octyl, n-nonyl, n-decyl, n-dodecyl, n-tetradecyl, n-hexadecyl, n-octadecyl, n-eicosyl and the like. Preferred alkyl groups include methyl, ethyl, n-propyl and isopropyl. Preferred optional suitable substituents include halo, methoxy, ethoxy, cyano, nitro and amino.

As used herein, unless otherwise indicated, the term "alkenyl" alone or in combination refers to a monovalent aliphatic hydrocarbon radical having the indicated number of carbon atoms and at least one carbon-carbon double bond. The radical may be a linear or branched chain, in the E or Z form, and where specified, optionally substituted with one to three suitable substituents as defined above. Illustrative examples of alkenyl groups include, but are not limited to, vinyl, 1-propenyl, 2-propenyl, isopropenyl, 1-butenyl, 2-butenyl, isobutenyl, 2-methyl-1-propenyl, 1-pentenyl, 2-pentenyl, 4-methyl-2-pentenyl, 1,3-pentadienyl, 2,4-pentadienyl, 1,3-butadienyl and the like. Preferred alkenyl groups include vinyl, 1-propenyl and 2-propenyl. Preferred optional suitable substituents include halo, methoxy, ethoxy, cyano, nitro and amino.

As used herein, unless otherwise indicated, the term "alkynyl" alone or in combination refers to a monovalent aliphatic hydrocarbon radical having the indicated number of carbon atoms and at least one carbon-carbon triple bond. The radical may be a linear or branched chain and, where specified, optionally substituted with one to three suitable substituents as defined above. Illustrative examples of alkynyl groups include, but are not limited to, ethynyl, 1-propynyl, 2-propynyl, 1-butynyl, 2-butynyl, 1-pentynyl, 2-pentynyl, 3-methyl-1-pentynyl, 3-pentynyl, 1-hexynyl, 2-hexynyl, 3-hexynyl and the like. Preferred alkynyl groups include ethynyl, 1-propynyl and 2-propynyl. Preferred optional suitable substituents include halo, methoxy, ethoxy, cyano, nitro and amino.

As used herein, unless otherwise indicated, the term "cycloalkyl" alone or in combination refers to a monovalent alicyclic saturated hydrocarbon radical having three or more carbons forming a carbocyclic ring and, where specified, optionally substituted with one to three suitable substituents as defined above. Illustrative examples of cycloalkyl groups include, but are not limited to, cyclopropyl, cyclobutyl, cyclopentyl, cyclohexyl, cycloheptyl, cyclooctyl, cyclononyl and the like. Preferred optional suitable substituents include halo, methyl, ethyl, methoxy, ethoxy, cyano, nitro and amino.

As used herein, unless otherwise indicated, the term "cycloalkenyl" alone or in combination refers to a monovalent alicyclic hydrocarbon radical having three or more carbons forming a carbocyclic ring and at least one carbon-carbon double bond and, where specified, optionally substituted with one to three suitable substituents as defined above. Illustrative examples of cycloalkenyl groups include, but are not limited to, cyclopentenyl, cyclohexenyl and the like. Preferred optional suitable substituents include halo, methyl, ethyl, methoxy, ethoxy, cyano, nitro and amino.

As used herein, unless otherwise indicated, the terms "alkylene", "alkenylene", "cycloalkylene" and "cycloalkenylene" refer to a divalent hydrocarbon radical that is formed by removal of a hydrogen atom from an alkyl, alkenyl, cycloalkyl or cycloalkenyl radical, respectively, as such terms are defined above.

As used herein, the term "($C_3$-$C_{10}$ cycloalkylene)($C_1$-$C_6$ alkylene)" refers to a divalent hydrocarbon radical that is formed by bonding a $C_3$-$C_{10}$ cycloalkylene radical with $C_1$-$C_6$ alkylene radical, as such terms are defined above.

As used herein, unless otherwise indicated, the term "aryl" alone or in combination refers to a monovalent aromatic hydrocarbon radical having six to ten carbon atoms forming a carbocyclic ring and, where specified, optionally substituted with one to three suitable substituents as defined above. Illustrative examples of aryl groups include, but are not limited to, phenyl, naphthyl, tetrahydronaphthyl, indanyl and the like. Preferred aryl groups are phenyl and naphthyl, optionally mono- or disubstituted by identical or different suitable substituents selected from halo, cyano, $C_1$-$C_3$ alkyl, $C_3$-$C_6$ cycloalkyl, difluoromethyl, trifluoromethyl, $C_1$-$C_3$ alkoxy, difluoromethoxy and trifluoromethoxy.

As used herein, unless otherwise indicated, the term "heterocycloalkyl" alone or in combination refers to a cycloalkyl group as defined above in which one or more carbons in the ring is replaced by a heteroatom selected from N, S and O. Illustrative examples of heterocycloalkyl groups include, but are not limited to, pyrrolidinyl, tetrahydrofuranyl, piperazinyl, tetrahydropyranyl, and the like.

As used herein, unless otherwise indicated, the term "heteroaryl" alone or in combination refers to a monovalent aromatic heterocyclic radical having two to nine carbons and one to four heteroatoms selected from N, S and O forming a five- to ten-membered monocyclic or fused bicyclic ring and, where specified, optionally substituted with one to three suitable substituents as defined above. Illustrative examples of heteroaryl groups include, but are not limited to, pyridyl, pyridazinyl, pyrazinyl, pyrimidinyl, triazinyl, quinolinyl, isoquinolinyl, quinoxalinyl, quinazolinyl, benzotriazinyl, benzimidazolyl, benzopyrazolyl, benzotriazolyl, benzisoxazolyl, isobenzofuryl, isoindolyl, indolizinyl, thienopyridinyl, thienopyrimidinyl, pyrazolopyrimidinyl, imidazopyridines, benzothiaxolyl, benzofuranyl, benzothienyl, indolyl, isothiazolyl, pyrazolyl, indazolyl, imidazolyl, triazolyl, tetrazolyl, oxazolyl, isoxazolyl, oxadiazolyl, thiadiazolyl, pyrrolyl, thiazolyl, furyl, thienyl and the like. Five- or six-membered monocyclic heteroaryl rings include: pyridyl, pyridazinyl, pyrazinyl, pyrimidinyl, triazinyl, isothiazolyl, pyrazolyl, imidazolyl, triazolyl, tetrazolyl, oxazolyl, isoxazolyl, oxadiazolyl, thiadiazolyl, pyrrolyl, thiazolyl, furyl, thienyl and the like. Eight- to ten-membered bicyclic heteroaryl rings having one to four heteroatoms include: quinolinyl, isoquinolinyl, quinoxalinyl, quinazolinyl, benzotriazinyl, benzimidazolyl, benzopyrazolyl, benzotriazolyl, benzisoxazolyl, isobenzofuryl, isoindolyl, indolizinyl, thienopyridinyl, thienopyrimidinyl, pyrazolopyrimidinyl, imidazopyridinyl, benzothiaxolyl, benzofuranyl, benzothienyl, indolyl, indazolyl, and the like. Preferred optional suitable substitutions include one or two identical or different substituents selected from halo, cyano, $C_1$-$C_3$ alkyl, $C_3$-$C_6$ cycloalkyl, difluoromethyl, trifluoromethyl, $C_1$-$C_3$ alkoxy, difluoromethoxy and trifluoromethoxy.

As used herein, unless otherwise indicated, the terms "alkoxy" and "alkyloxy" alone or in combination refer to an aliphatic radical of the form alkyl-O—, wherein alkyl is as defined above. Illustrative examples of alkoxy groups include, but are not limited to, methoxy, ethoxy, propoxy, isopropoxy, butoxy, isobutoxy, tertiary butoxy, pentoxy, isopentoxy, neopentoxy, tertiary pentoxy, hexoxy, isohexoxy, heptoxy, octoxy and the like. Preferred alkoxy groups include methoxy and ethoxy.

As used herein, unless otherwise indicated, the term "haloalkyl" refers to an alkyl radical as described above substituted with one or more halogens. Illustrative examples of haloalkyl groups include, but are not limited to, chloromethyl, dichloromethyl, fluoromethyl, difluoromethyl, trifluoromethyl, 2,2,2-trichloroethyl and the like.

As used herein, unless otherwise indicated, the term "haloalkoxy" refers to an alkoxy radical as described above substituted with one or more halogens. Illustrative examples of haloalkoxy groups include, but are not limited to, trifluoromethoxy, difluoromethoxy and the like.

As used herein, unless otherwise indicated, the term "aralkyl" refers to an alkyl radical of one to six carbons as described above substituted with an aryl group as described above.

As used herein, unless otherwise indicated, the term "heteroaralkyl" refers to an alkyl radical of one to six carbons as described above substituted with a heteroaryl group as described above.

As used herein, unless otherwise indicated, the term "aralkoxy" refers to an alkoxy radical of one to six carbons as described above substituted with an aryl group as described above.

As used herein, unless otherwise indicated, the term "heteroaralkoxy" refers to an alkoxy radical of one to six carbons as described above substituted with a heteroaryl group as described above.

As used herein, unless otherwise indicated, the term "carbamoyl" refers to a monovalent radical of the form —C(O)NH(R), wherein R is hydrogen, $C_1$-$C_6$ alkyl, $C_2$-$C_6$ alkenyl, $C_3$-$C_6$ cycloalkyl, or aryl as such terms are defined above.

As used herein, unless otherwise indicated, the terms "di-($C_1$-$C_3$ alkyl)amino" and "di-($C_1$-$C_6$ alkyl)amino" alone or in combination refer to an amino group that is substituted with two groups independently selected from $C_1$-$C_3$ alkyl or $C_1$-$C_6$ alkyl, respectively.

As used herein, the terms "treating" and "treatment" refer to delaying the onset of, retarding or reversing the progress of, or alleviating or preventing either the disease or condition to which the term applies, or one or more symptoms of such disease or condition.

As used herein, the term "administering" means oral administration, administration as a suppository, topical contact, intravenous, intraperitoneal, intramuscular, intralesional, intranasal or subcutaneous administration, or the implantation of a slow-release device, e.g., a mini-osmotic pump, to a subject. Administration is by any route including parenteral, and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, and the like.

As used herein, the term "prodrug" refers to a precursor compound that, following administration, releases the biologically active compound in vivo via some chemical or physiological process (e.g., a prodrug on reaching physiological pH or through enzyme action is converted to the biologically active compound). A prodrug itself may either lack or possess the desired biological activity.

As used herein, the term "compound" refers to a molecule produced by any means including, without limitation, synthesis in vitro or generation in situ or in vivo.

The terms "controlled release," "sustained release," "extended release," and "timed release" are intended to refer interchangeably to any drug-containing formulation in which release of the drug is not immediate, i.e., with a "controlled release" formulation, oral administration does not result in immediate release of the drug into an absorption pool. The terms are used interchangeably with "nonimmediate release" as defined in *Remington: The Science and Practice of Pharmacy*, 21$^{st}$ Ed., Gennaro, Ed., Lippencott Williams & Wilkins (2003). As discussed therein, immediate and nonimmediate release can be defined kinetically by reference to the following equation:

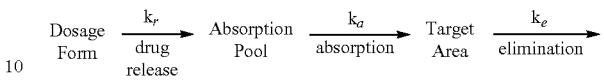

The "absorption pool" represents a solution of the drug administered at a particular absorption site, and $k_r$, $k_a$ and $k_e$ are first-order rate constants for (1) release of the drug from the formulation, (2) absorption, and (3) elimination, respectively. For immediate release dosage forms, the rate constant for drug release $k_r$ is far greater than the absorption rate constant $k_a$. For controlled release formulations, the opposite is true, i.e., $k_r \ll k_a$, such that the rate of release of drug from the dosage form is the rate-limiting step in the delivery of the drug to the target area.

The terms "sustained release" and "extended release" are used in their conventional sense to refer to a drug formulation that provides for gradual release of a drug over an extended period of time, for example, 12 hours or more, and that preferably, although not necessarily, results in substantially constant blood levels of a drug over an extended time period.

As used herein, the tern "delayed release" refers to a pharmaceutical preparation that passes through the stomach intact and dissolves in the small intestine.

General

The present invention provides compounds having an inhibitory effect on sodium-dependent glucose cotransporter SGLT, preferably SGLT2. Some compounds according to the present invention also have an inhibitory effect on sodium-dependent glucose cotransporter SGLT1. Owing to their ability to inhibit SGLT, the compounds of the present invention are suitable for the treatment and/or prevention of any and all conditions and diseases that are affected by inhibition of SGLT activity, particularly SGLT2 activity. Therefore, the compounds of the present invention are suitable for the prevention and treatment of diseases and conditions, particularly metabolic disorders, including but not limited to type 1 and type 2 diabetes mellitus, hyperglycemia, diabetic complications (such as retinopathy, nephropathy [e.g., progressive renal disease], neuropathy, ulcers, micro- and macroangiopathies, and diabetic foot disease), insulin resistance, metabolic syndrome (Syndrome X), hyperinsulinemia, hypertension, hyperuricemia, obesity, edema, dyslipidemia, chronic heart failure, atherosclerosis and related diseases.

The present invention also provides pharmaceutically acceptable salts and prodrugs of compounds according to the present invention.

The present invention further provides pharmaceutical compositions comprising an effective amount of a compound or mixture of compounds according to the present invention, or a pharmaceutically acceptable salt or prodrug thereof, in a pharmaceutically acceptable carrier.

The present invention further provides synthetic intermediates and processes for preparing the compounds of the present invention.

The present invention also provides methods of using the compounds according to the present invention, independently or in combination with other therapeutic agents, for treating diseases and conditions which may be affected by SGLT inhibition.

The present invention also provides methods of using the compounds according to the present invention for the preparation of a medicament for treating diseases and conditions which may be affected by SGLT inhibition.

Detailed Embodiments

Compounds and Preparative Methods

In one aspect, the present invention provides for compounds of Formula I:

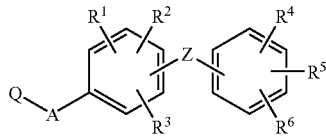

wherein
A represents oxygen; NH; methylene; or a single bond;
Q is selected from one of the following formulae $Q^1$ to $Q^4$;

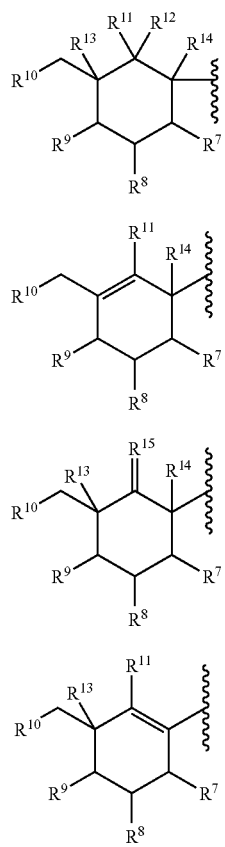

wherein the wavy line indicates the point of attachment to the remainder of the molecule;

Z represents oxygen; sulfur; SO; $SO_2$; 1,1-cyclopropylene; carbonyl; or methylene optionally substituted with one to two substituents independently selected from halo, hydroxy, $C_1$-$C_6$ alkyl, $C_1$-$C_6$ alkoxy, $C_3$-$C_6$ cycloalkyl and $C_3$-$C_6$ cycloalkyloxy;

$R^1$, $R^2$ and $R^3$ each independently represent hydrogen, halo, hydroxy, $C_1$-$C_6$ alkyl, $C_2$-$C_6$ alkenyl, $C_2$-$C_6$ alkynyl, $C_3$-$C_{10}$ cycloalkyl, $C_5$-$C_{10}$ cycloalkenyl, $C_1$-$C_6$ alkyloxy, $C_3$-$C_{10}$ cycloalkyloxy, cyano, amino or nitro, wherein alkyl, alkenyl, alkynyl, cycloalkyl and cycloalkenyl groups or portions optionally may be partly or completely fluorinated and may be mono- or disubstituted by identical or different substituents selected from chlorine, hydroxy, $C_1$-$C_3$ alkoxy and $C_1$-$C_3$ alkyl, and in cycloalkyl and cycloalkenyl groups or portions one or two methylene groups are optionally replaced independently of one another by $NR^a$, O, S, CO, SO or $SO_2$, and one or two methyne groups optionally may be replaced by N, or in the event that $R^1$ and $R^2$ are bound to two adjacent C atoms of the phenyl ring, $R^1$ and $R^2$ may be joined together such that $R^1$ and $R^2$ together form a $C_3$-$C_5$ alkylene, $C_3$-$C_5$ alkenylene or butadienylene bridge, which may be partly or completely fluorinated and may be mono- or disubstituted by identical or different substituents selected from chlorine, hydroxy, $C_1$-$C_3$ alkoxy and $C_1$-$C_3$ alkyl, and wherein one or two methylene groups are optionally replaced independently of one another by O, S, CO, SO, $SO_2$ or $NR^a$, and wherein one or two methyne groups optionally may be replaced by N;

$R^4$ independently represents hydrogen, halo, cyano, nitro, amino, hydroxy, $C_1$-$C_6$ alkyl, $C_2$-$C_6$ alkenyl, $C_2$-$C_6$ alkynyl, $C_3$-$C_{10}$ cycloalkyl, $C_5$-$C_{10}$ cycloalkenyl, $C_1$-$C_6$ alkyloxy, $C_3$-$C_{10}$ cycloalkyloxy, ($C_1$-$C_6$ alkyloxy)$C_1$-$C_6$ alkyloxy, $C_5$-$C_7$ cycloalkenyloxy, aryl, heteroaryl, aryloxy, heteroaryloxy, ($C_2$-$C_4$ alkenyl)$C_1$-$C_3$ alkyloxy, ($C_2$-$C_4$ alkynyl)$C_1$-$C_3$ alkyloxy, (aryl)$C_1$-$C_3$ alkyloxy, (heteroaryl)$C_1$-$C_3$ alkyloxy, ($C_3$-$C_{10}$ cycloalkyl)$C_1$-$C_3$ alkyl, ($C_3$-$C_{10}$ cycloalkyl)$C_1$-$C_3$ alkyloxy, ($C_5$-$C_{10}$ cycloalkenyl)$C_1$-$C_3$ alkyl, ($C_5$-$C_{10}$ cycloalkenyl)$C_1$-$C_3$ alkyloxy, ($C_1$-$C_4$ alkyloxy)$C_1$-$C_3$ alkyl, ($C_3$-$C_7$ cycloalkyloxy)$C_1$-$C_3$ alkyl, ($C_3$-$C_7$ cycloalkyloxy)$C_2$-$C_4$ alkenyl, ($C_3$-$C_7$ cycloalkyloxy)$C_2$-$C_4$ alkynyl, ($C_3$-$C_7$ cycloalkyloxy)$C_1$-$C_3$ alkyloxy, ($C_1$-$C_4$ alkylamino)$C_1$-$C_3$ alkyl, di-($C_1$-$C_3$ alkylamino)$C_1$-$C_3$ alkyl, tri-($C_1$-$C_4$ alkyl)silyl-$C_1$-$C_6$ alkyl, tri-($C_1$-$C_4$ alkyl)silyl-$C_2$-$C_6$ alkenyl, tri-($C_1$-$C_4$ alkyl)silyl-$C_2$-$C_6$ alkynyl, tri-($C_1$-$C_4$ alkyl)silyl-$C_1$-$C_6$ alkyloxy, ($C_3$-$C_7$ cycloalkyl)$C_2$-$C_5$ alkenyl, ($C_3$-$C_7$ cycloalkyl)$C_3$-$C_5$ alkenyloxy, ($C_3$-$C_7$ cycloalkyl)$C_3$-$C_5$ alkynyloxy, ($C_5$-$C_8$ cycloalkenyl)$C_3$-$C_5$ alkenyloxy, ($C_5$-$C_8$ cycloalkenyl)$C_3$-$C_5$ alkynyloxy, $C_3$-$C_6$ cycloalkylidenmethyl, ($C_1$-$C_4$ alkyl)carbonyl, arylcarbonyl, heteroarylcarbonyl, aminocarbonyl, ($C_1$-$C_4$ alkyl)aminocarbonyl, di-($C_1$-$C_3$ alkyl)aminocarbonyl, hydroxycarbonyl, ($C_1$-$C_4$ alkyloxy)carbonyl, $C_1$-$C_4$ alkylamino, di-($C_1$-$C_3$ alkyl)amino, ($C_1$-$C_4$ alkyl)carbonylamino, arylcarbonylamino, heteroarylcarbonylamino, $C_1$-$C_4$ alkylsulfonylamino, arylsulfonylamino, $C_1$-$C_4$ alkylsulfanyl, $C_1$-$C_4$ alkylsulfinyl, $C_1$-$C_4$ alkylsulfonyl, $C_3$-$C_{10}$ cycloalkylsulfanyl, $C_3$-$C_{10}$ cycloalkylsulfinyl, $C_3$-$C_{10}$ cycloalkylsulfonyl, $C_5$-$C_{10}$ cycloalkenylsulfanyl, $C_5$-$C_{10}$ cycloalkenylsulfinyl, $C_5$-$C_{10}$ cycloalkenylsulfonyl, arylsulfanyl, arylsulfinyl or arylsulfonyl, wherein alkyl, alkenyl, alkynyl, cycloalkyl and cycloalkenyl groups or portions optionally may be partly or completely fluorinated and may be mono- or disubstituted by identical or different substituents selected from chlorine, hydroxy, $C_1$-$C_3$ alkoxy and $C_1$-$C_3$ alkyl, and in cycloalkyl and cycloalkenyl groups or portions one or two methylene groups are optionally replaced independently of one another by $NR^a$, O, S, CO, SO or $SO_2$, and one or two methyne groups optionally may be replaced by N;

$R^5$ and $R^6$ each independently represent hydrogen, halo, cyano, nitro, hydroxy, $C_1$-$C_6$ alkyl, $C_2$-$C_6$ alkenyl, $C_2$-$C_6$ alkynyl, $C_3$-$C_{10}$ cycloalkyl, $C_1$-$C_3$ alkyloxy or $C_3$-$C_{10}$ cycloalkyloxy, wherein alkyl, alkenyl, alkynyl, cycloalkyl and cycloalkenyl groups or portions optionally may be partly or completely fluorinated and may be mono- or disubstituted by identical or different substituents selected from chlorine, hydroxy, $C_1$-$C_3$ alkoxy and $C_1$-$C_3$ alkyl, and in cycloalkyl and cycloalkenyl groups or portions one or two methylene groups are optionally replaced independently of one another by $NR^a$, O, S, CO, SO or $SO_2$, and one or two methyne groups optionally may be replaced by N, or if $R^5$ and $R^6$ are bound to two adjacent C atoms of the phenyl ring, $R^5$ and $R^6$ optionally may be joined together such that $R^5$ and $R^6$ together form a $C_3$-$C_5$ alkylene, $C_3$-$C_5$ alkenylene or butadienylene bridge, which may be partly or completely fluorinated and mono- or disubstituted by identical or different substituents selected from chlorine, hydroxy, $C_1$-$C_3$ alkoxy and $C_1$-$C_3$ alkyl, and wherein one or two methylene groups are optionally replaced independently of one another by O, S, CO, SO, $SO_2$ or $NR^a$, and wherein one or two methyne groups may be replaced by N;

$R^7$, $R^8$, $R^9$ and $R^{10}$ each independently represent hydroxy, ($C_1$-$C_{18}$ alkyl)carbonyloxy, ($C_1$-$C_{18}$ alkyl)oxycarbonyloxy, arylcarbonyloxy, aryl-($C_1$-$C_3$ alkyl)carbonyloxy, ($C_3$-$C_{10}$ cycloalkyl)carbonyloxy, hydrogen, halo, $C_1$-$C_6$ alkyl, $C_2$-$C_6$ alkenyl, $C_2$-$C_6$ alkynyl, ($C_3$-$C_{10}$ cycloalkyl)$C_1$-$C_3$ alkyl, ($C_5$-$C_7$ cycloalkenyl)$C_1$-$C_3$ alkyl, (aryl)$C_1$-$C_3$ alkyl, (heteroaryl)$C_1$-$C_3$ alkyl, $C_1$-$C_6$ alkyloxy, $C_2$-$C_6$ alkenyloxy, $C_2$-$C_6$ alkynyloxy, $C_3$-$C_7$ cycloalkyloxy, $C_5$-$C_7$ cycloalkenyloxy, aryloxy, heteroaryloxy, ($C_3$-$C_7$ cycloalkyl)$C_1$-$C_3$ alkyloxy, ($C_5$-$C_7$ cycloalkenyl)$C_1$-$C_3$ alkyloxy, (aryl)$C_1$-$C_3$ alkyloxy, (heteroaryl)$C_1$-$C_3$ alkyloxy, aminocarbonyl, hydroxycarbonyl, ($C_1$-$C_4$ alkyl)aminocarbonyl, di-($C_1$-$C_3$ alkyl)aminocarbonyl, ($C_1$-$C_4$ alkyloxy)carbonyl, (aminocarbonyl)$C_1$-$C_3$ alkyl, ($C_1$-$C_4$ alkyl)aminocarbonyl-($C_1$-$C_3$)alkyl, di-($C_1$-$C_3$ alkyl)aminocarbonyl-($C_1$-$C_3$)alkyl, (hydroxycarbonyl)$C_1$-$C_3$ alkyl, ($C_1$-$C_4$ alkyloxy)carbonyl-($C_1$-$C_3$)alkyl, ($C_3$-$C_7$ cycloalkyloxy)$C_1$-$C_3$ alkyl, ($C_5$-$C_7$ cycloalkenyloxy)$C_1$-$C_3$ alkyl, (aryloxy)$C_1$-$C_3$ alkyl, (heteroaryloxy)$C_1$-$C_3$ alkyl, $C_1$-$C_4$ alkylsulfonyloxy, arylsulfonyloxy, (aryl)$C_1$-$C_3$ alkylsulfonyloxy, trimethylsilyloxy, t-butyldimethylsilyloxy, or cyano; wherein alkyl, alkenyl, alkynyl, cycloalkyl and cycloalkenyl groups or portions optionally may be partly or completely fluorinated and may be mono- or disubstituted by identical or different substituents selected from chlorine, hydroxy, $C_1$-$C_3$ alkoxy and $C_1$-$C_3$ alkyl, and in cycloalkyl and cycloalkenyl groups or portions one or two methylene groups are optionally replaced independently of one another by $NR^a$, O, S, CO, SO or $SO_2$;

and optionally, $R^{10}$ and $R^{11}$ can be combined with the carbon atoms to which each is attached to form a five- to seven-membered fused cycloalkane or cycloalkene ring that is optionally partly or completely fluorinated and may be mono- or disubstituted by identical or different substituents selected from chlorine, hydroxy, $C_1$-$C_3$ alkoxy and $C_1$-$C_3$ alkyl, and wherein in the cycloalkyl and cycloalkenyl rings one or two methylene groups are optionally replaced independently of one another by $NR^a$, O, S, CO, SO or $SO_2$;

$R^{11}$ and $R^{12}$ each independently represents hydrogen, hydroxy, halo, $C_1$-$C_6$ alkyl, $C_2$-$C_6$ alkenyl, $C_2$-$C_6$ alkynyl, $C_3$-$C_{10}$ cycloalkyl, $C_1$-$C_6$ alkyloxy, $C_2$-$C_6$ alkenyloxy, $C_2$-$C_6$ alkynyloxy or $C_3$-$C_6$ cycloalkyloxy, wherein alkyl, alkenyl, alkynyl and cycloalkyl groups or portions optionally may be partly or completely fluorinated, or $R^{11}$ and $R^{12}$ optionally may be joined together such that $R^{11}$ and $R^{12}$ together with the carbon atom to which they are attached form a $C_3$-$C_7$ spirocycloalkane ring which optionally may be partly or completely fluorinated and may be mono- or disubstituted by identical or different substituents selected from chlorine, hydroxy, $C_1$-$C_3$ alkoxy and $C_1$-$C_3$ alkyl;

wherein when Q is $Q^1$ and both $R^{11}$ and $R^{12}$ are hydrogen, then at least one of $R^{10}$ or $R^{14}$ is halo or $R^{13}$ is other than hydrogen or $R^4$ is $C_2$-$C_6$ alkynyl, $C_3$-$C_{10}$ cycloalkyloxy, $C_5$-$C_7$ cycloalkenyloxy, ($C_3$-$C_{10}$ cycloalkyl)$C_1$-$C_3$ alkyloxy, ($C_3$-$C_7$ cycloalkyl)$C_3$-$C_5$ alkenyloxy, ($C_3$-$C_7$ cycloalkyl)$C_3$-$C_5$ alkynyloxy, ($C_5$-$C_{10}$ cycloalkenyl)$C_1$-$C_3$ alkyloxy, ($C_5$-$C_8$ cycloalkenyl)$C_3$-$C_5$ alkenyloxy or ($C_5$-$C_8$ cycloalkenyl)$C_3$-$C_5$ alkynyloxy, or when Q is $Q^2$ and $R^{11}$ is hydrogen, then at least $R^{10}$ is halo or $R^4$ is $C_2$-$C_6$ alkynyl, $C_3$-$C_{10}$ cycloalkyloxy, $C_5$-$C_7$ cycloalkenyloxy, ($C_3$-$C_{10}$ cycloalkyl)$C_1$-$C_3$ alkyloxy, ($C_3$-$C_7$ cycloalkyl)$C_3$-$C_5$ alkenyloxy, ($C_3$-$C_7$ cycloalkyl)$C_3$-$C_5$ alkynyloxy, ($C_5$-$C_{10}$ cycloalkenyl)$C_1$-$C_3$ alkyloxy, ($C_5$-$C_8$ cycloalkenyl)$C_3$-$C_5$ alkenyloxy or ($C_5$-$C_8$ cycloalkenyl)$C_3$-$C_5$ alkynyloxy, or when Q is $Q^4$ and $R^{11}$ is hydrogen, then at least $R^{10}$ is halo or $R^{13}$ is other than hydrogen or $R^4$ is $C_2$-$C_6$ alkynyl, $C_3$-$C_{10}$ cycloalkyloxy, $C_5$-$C_7$ cycloalkenyloxy, ($C_3$-$C_{10}$ cycloalkyl)$C_1$-$C_3$ alkyloxy, ($C_3$-$C_7$ cycloalkyl)$C_3$-$C_5$ alkenyloxy, ($C_3$-$C_7$ cycloalkyl)$C_3$-$C_5$ alkynyloxy, ($C_5$-$C_{10}$ cycloalkenyl)$C_1$-$C_3$ alkyloxy, ($C_5$-$C_8$ cycloalkenyl)$C_3$-$C_5$ alkenyloxy or ($C_5$-$C_8$ cycloalkenyl)$C_3$-$C_5$ alkynyloxy;

$R^{13}$ and $R^{14}$ each independently represent hydrogen, hydroxy, halo, $C_1$-$C_6$ alkyl, $C_2$-$C_6$ alkenyl, $C_2$-$C_6$ alkynyl, $C_3$-$C_{10}$ cycloalkyl, $C_1$-$C_6$ alkyloxy, $C_2$-$C_6$ alkenyloxy, $C_2$-$C_6$ alkynyloxy or $C_3$-$C_6$ cycloalkyloxy, wherein alkyl, alkenyl, alkynyl and cycloalkyl groups or portions optionally may be partly or completely fluorinated;

$R^{15}$ independently represents oxygen or $CR^bR^c$;

$R^a$ independently represents hydrogen, $C_1$-$C_4$ alkyl or ($C_1$-$C_4$ alkyl)carbonyl, wherein alkyl groups or portions optionally may be partly or completely fluorinated; and $R^b$ and $R^c$ each independently represent hydrogen, halo or $C_1$-$C_4$ alkyl, wherein alkyl groups optionally may be partly or completely fluorinated.

The style used above and hereinafter, in which a bond of a substituent on a phenyl group is shown ending near the center of the phenyl ring, denotes, unless otherwise stated, that this substituent may be bound to any free position of the phenyl group bearing a hydrogen atom.

The present invention includes all tautomers and stereoisomers of compounds of Formula I, either in admixture or in pure or substantially pure form. The compounds of the present invention can have asymmetric centers at the carbon atoms, and therefore the compounds of Formula I can exist in diastereomeric or enantiomeric forms or mixtures thereof. All conformational isomers (e.g., cis and trans isomers) and all optical isomers (e.g., enantiomers and diastereomers), racemic, diastereomeric and other mixtures of such isomers, as well as solvates, hydrates, isomorphs, polymorphs and tautomers are within the scope of the present invention. Compounds according to the present invention can be prepared using diastereomers, enantiomers or racemic mixtures as starting materials. Furthermore, diastereomer and enantiomer products can be separated by chromatography, fractional crystallization or other methods known to those of skill in the art.

The present invention also provides for the prodrugs of compounds of Formula I. Prodrugs of compounds of the invention include, but are not limited to, carboxylate esters, carbonate esters, hemi-esters, phosphorus esters, nitro esters, sulfate esters, sulfoxides, amides, carbamates, azo compounds, phosphamides, glycosides, ethers, acetals, and ketals. Prodrug esters and carbonates may be formed, for example, by reacting one or more hydroxyl groups of compounds of Formula I with alkyl, alkoxy or aryl substituted acylating reagents using methods known to those of skill in the art to produce methyl carbonates, acetates, benzoates, pivalates and the like. Illustrative examples of prodrug esters of the compounds of the present invention include, but are not limited to, compounds of Formula I having a carboxyl moiety wherein the free hydrogen is replaced by $C_1$-$C_4$ alkyl, $C_1$-$C_7$ alkanoyloxymethyl, 1-(($C_1$-$C_5$)alkanoyloxy)ethyl, 1-methyl-1-(($C_1$-$C_5$)alkanoyloxy)-ethyl, $C_1$-$C_5$ alkoxycarbonyloxymethyl, 1-(($C_1$-$C_5$)alkoxycarbonyloxy)ethyl, 1-methyl-1-(($C_1$-$C_5$)alkoxycarbonyloxy)ethyl, N-(($C_1$-$C_5$)alkoxycarbonyl)aminomethyl, 1-(N-(($C_1$-$C_5$)alkoxycarbonyl)amino)ethyl, 3-phthalidyl, 4-crotonolactonyl, gamma-butyrolacton-4-yl, di-N,N-($C_1$-$C_2$)alkylamino($C_2$-$C_3$)alkyl (e.g., beta-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl. Oligopeptide modifications and biodegradable polymer derivatives (as described, for example, in Int. J. Pharm. 115, 61-67, 1995) are within the scope of the invention. Methods for selecting and preparing suitable prodrugs are provided, for example, in the following: T. Higuchi and V. Stella, "Prodrugs as Novel Delivery Systems," Vol. 14, ACS Symposium Series, 1975; H. Bundgaard, "Design of Prodrugs," Elsevier, 1985; and "Bioreversible Carriers in Drug Design," ed. Edward Roche, American Pharmaceutical Association and Pergamon Press, 1987.

The present invention also provides for the pharmaceutically acceptable salts of compounds of Formula I and prodrugs thereof. The acids that can be used as reagents to prepare the pharmaceutically acceptable acid addition salts of the basic compounds of this invention are those which form non-toxic acid addition salts, i.e., salts containing pharmacologically acceptable anions (such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate (1,1'-methylene-bis-2-hydroxy-3-naphthoate) salts). The bases that can be used as reagents to prepare the pharmaceutically acceptable base salts of the acidic compounds of the present invention are those that form non-toxic base salts with such compounds, including, but not limited to, those derived from pharmacologically acceptable cations such as alkali metal cations (e.g., potassium, lithium and sodium) and alkaline earth metal cations (e.g., calcium and magnesium), ammonium or water-soluble amine addition salts such as N-methylglucamine (meglumine), and the lower alkanolammonium and other base salts of pharmaceutically acceptable organic amines (e.g., methylamine, ethylamine, propylamine, dimethylamine, triethanolamine, diethylamine, t-butylamine, t-octylamine, trimethylamine, triethylamine, ethylenediamine, hydroxyethylamine, morpholine, piperazine, dehydroabietylamine, lysine and guanidine).

The present invention also includes isotopically-labeled compounds of Formula I, wherein one or more atoms are replaced by one or more atoms having specific atomic mass or mass numbers. Examples of isotopes that can be incorporated into compounds of the invention include, but are not limited to, isotopes of hydrogen, carbon, nitrogen, oxygen, fluorine, sulfur, and chlorine (such as $^2H$, $^3H$, $^{13}C$, $^{14}C$, $^{15}N$, $^{18}O$, $^{17}O$, $^{18}F$, $^{35}S$ and $^{36}Cl$). Isotopically-labeled compounds of Formula I and prodrugs thereof, as well as isotopically-labeled, pharmaceutically acceptable salts of compounds of Formula I and prodrugs thereof, are within the scope of the present invention. Isotopically-labeled compounds of the present invention are useful in assays of the tissue distribution of the compounds and their prodrugs and metabolites; preferred isotopes for such assays include $^3H$ and $^{14}C$. In addition, in certain circumstances substitution with heavier isotopes, such as deuterium ($^2H$), can provide increased metabolic stability, which offers therapeutic advantages such as increased in vivo half-life or reduced dosage requirements. Isotopically-labeled compounds of this invention and prodrugs thereof can generally be prepared according to the methods described herein by substituting an isotopically-labeled reagent for a non-isotopically labeled reagent.

In preferred embodiments, A represents oxygen or a single bond. In particularly preferred embodiments, A represents a single bond.

In preferred embodiments, Z represents oxygen, sulfur, or methylene optionally substituted with one to two substituents independently selected from halo, hydroxy, $C_1$-$C_6$ alkyl, $C_1$-$C_6$ alkoxy, $C_3$-$C_6$ cycloalkyl and $C_3$-$C_6$ cycloalkyloxy. In particularly preferred embodiments, Z represents methylene.

In preferred embodiments, $R^1$, $R^2$ and $R^3$ each independently represent hydrogen, halo, hydroxy, $C_1$-$C_6$ alkyl, $C_2$-$C_6$ alkenyl, $C_2$-$C_6$ alkynyl, $C_3$-$C_{10}$ cycloalkyl, $C_1$-$C_6$ alkyloxy, or cyano. In particularly preferred embodiments, $R^1$, $R^2$ and $R^3$ each independently represent hydrogen, halo or $C_1$-$C_6$ alkyl. In more particularly preferred embodiments, $R^1$ represents hydrogen, halo or $C_1$-$C_6$ alkyl and $R^2$ and $R^3$ both represent hydrogen.

In preferred embodiments, $R^4$ represents $C_1$-$C_6$ alkyl, $C_2$-$C_6$ alkenyl, $C_2$-$C_6$ alkynyl, $C_3$-$C_{10}$ cycloalkyl, $C_1$-$C_6$ alkyloxy, $C_3$-$C_{10}$ cycloalkyloxy, ($C_3$-$C_{10}$ cycloalkyl)$C_1$-$C_3$ alkyloxy, ($C_3$-$C_7$ cycloalkyl)$C_3$-$C_5$ alkenyloxy, or ($C_3$-$C_7$ cycloalkyl)$C_3$-$C_5$ alkynyloxy.

In preferred embodiments, $R^5$ and $R^6$ each independently represent hydrogen, halo, hydroxy, $C_1$-$C_6$ alkyl, $C_2$-$C_6$ alkenyl, $C_2$-$C_6$ alkynyl, $C_3$-$C_{10}$ cycloalkyl, $C_1$-$C_6$ alkyloxy, or cyano. In particularly preferred embodiments, $R^5$ and $R^6$ each independently represent hydrogen, halo or $C_1$-$C_6$ alkyl. In more particularly preferred embodiments, $R^5$ and $R^6$ both represent hydrogen.

In preferred embodiments, $R^7$, $R^8$, $R^9$ and $R^{10}$ each independently represent hydroxy, halo, $C_1$-$C_6$ alkyl, $C_1$-$C_6$ alkyloxy, ($C_3$-$C_7$)cycloalkyloxy, aryloxy or ($C_3$-$C_7$)cycloalkyl-($C_1$-$C_3$)alkyloxy, wherein alkyl and cycloalkyl groups or portions may be partly or completely fluorinated. In particularly preferred embodiments, $R^7$, $R^8$, $R^9$ and $R^{10}$ each represent hydroxy.

In preferred embodiments, $R^{11}$ represents hydrogen or hydroxy.

In preferred embodiments, $R^{12}$, $R^{13}$ and $R^{14}$ represent hydrogen.

In preferred embodiments, $R^{15}$ represents oxygen or $CR^bR^c$, wherein $R^b$ and $R^c$ each independently represent hydrogen or halo.

As noted above, Formula IA represents still other preferred embodiments:

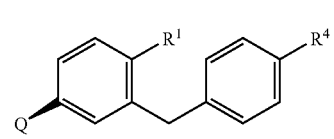

IA wherein $R^1$ represents hydrogen, halo or $C_1$-$C_6$ alkyl; $R^4$ represents $C_1$-$C_6$ alkyl, $C_2$-$C_6$ alkenyl, $C_2$-$C_6$ alkynyl, $C_3$-$C_{10}$ cycloalkyl, $C_1$-$C_6$ alkyloxy, $C_3$-$C_{10}$ cycloalkyloxy, ($C_3$-$C_{10}$ cycloalkyl)$C_1$-$C_3$ alkyloxy, ($C_3$-$C_7$ cycloalkyl)$C_3$-$C_5$ alkenyloxy, or ($C_3$-$C_7$ cycloalkyl)$C_3$-$C_5$ alkynyloxy; and Q is selected from the following formulae $Q^{1A}$ to $Q^{4A}$:

| | |
|---|---|
| 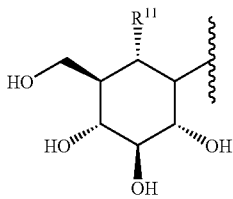 $Q^{1A}$ | 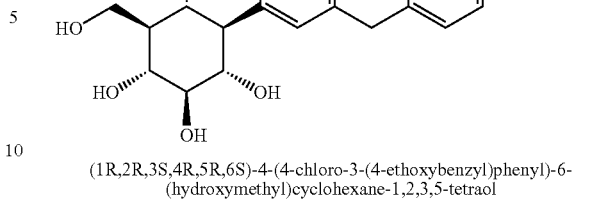<br>(1R,2R,3S,4R,5R,6S)-4-(4-chloro-3-(4-ethoxybenzyl)phenyl)-6-(hydroxymethyl)cyclohexane-1,2,3,5-tetraol |
| 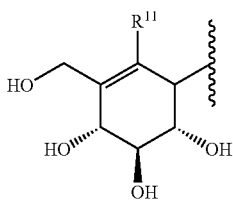 $Q^{2A}$ | 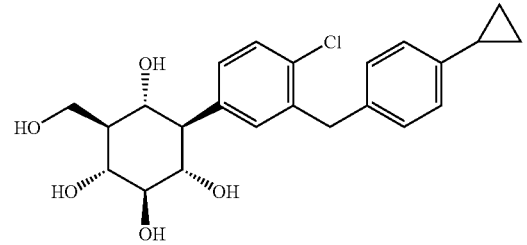<br>(1R,2R,3S,4R,5R,6S)-4-(4-chloro-3-(4-cyclopropylbenzyl)phenyl)-6-(hydroxymethyl)cyclohexane-1,2,3,5-tetraol |
| 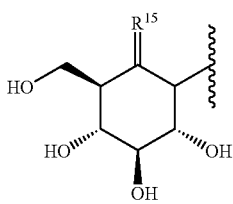 $Q^{3A}$ | 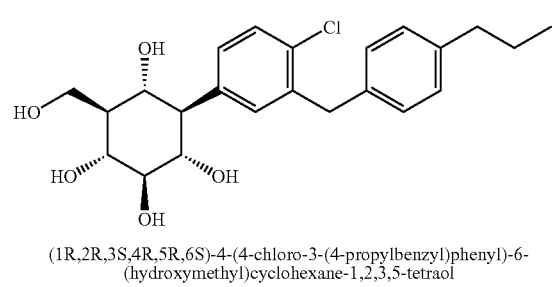<br>(1R,2R,3S,4R,5R,6S)-4-(4-chloro-3-(4-propylbenzyl)phenyl)-6-(hydroxymethyl)cyclohexane-1,2,3,5-tetraol |
| 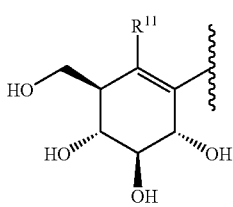 $Q^{4A}$ | 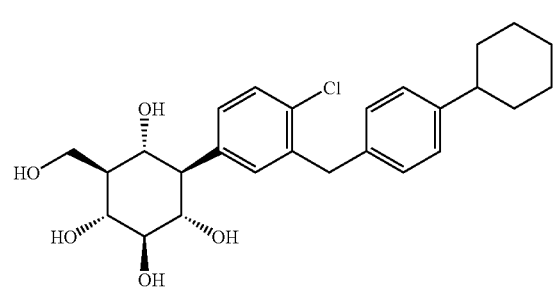<br>(1R,2R,3S,4R,5R,6S)-4-(4-chloro-3-(4-cyclohexylbenzyl)phenyl)-6-(hydroxymethyl)cyclohexane-1,2,3,5-tetraol | wherein $R^{11}$ represents hydrogen or hydroxy, and $R^{15}$ represents oxygen or $CR^b R^c$, wherein $R^b$ and $R^c$ each independently represent hydrogen or halo; wherein when $R^{11}$ is hydrogen, then $R^4$ is $C_2$-$C_6$ alkynyl, $C_3$-$C_{10}$ cycloalkyloxy, $(C_3$-$C_{10}$ cycloalkyl)$C_1$-$C_3$ alkyloxy, $(C_3$-$C_7$ cycloalkyl)$C_3$-$C_5$ alkenyloxy, or $(C_3$-$C_7$ cycloalkyl)$C_3$-$C_5$ alkynyloxy. In some embodiments, Q is selected from the group consisting of formulae $Q^{1A}$ to $Q^{3A}$.

In particularly preferred embodiments, compounds of the present invention are selected from:

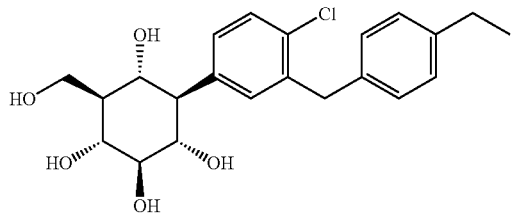
(1R,2R,3S,4R,5R,6S)-4-(4-chloro-3-(4-ethylbenzyl)phenyl)-6-(hydroxymethyl)cyclohexane-1,2,3,5-tetraol

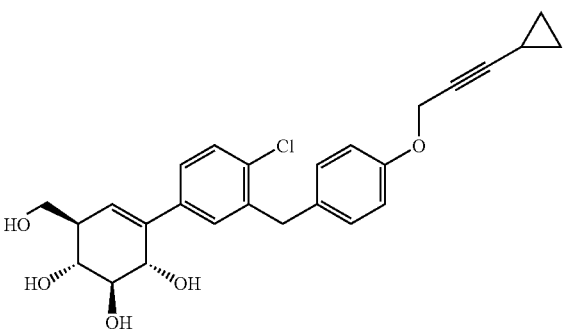
(1R,2S,3S,6R)-4-(4-chloro-3-(4-cyclopropylprop-2-ynyloxy)benzyl)phenyl)-6-(hydroxymethyl)cyclohex-4-ene-1,2,3-triol -continued

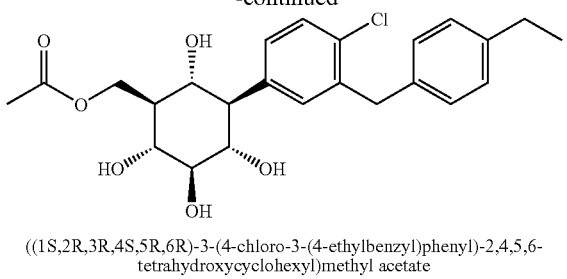

((1S,2R,3R,4S,5R,6R)-3-(4-chloro-3-(4-ethylbenzyl)phenyl)-2,4,5,6-tetrahydroxycyclohexyl)methyl acetate

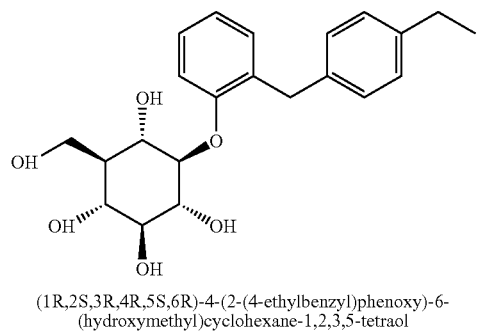

(1R,2S,3R,4R,5S,6R)-4-(2-(4-ethylbenzyl)phenoxy)-6-(hydroxymethyl)cyclohexane-1,2,3,5-tetraol

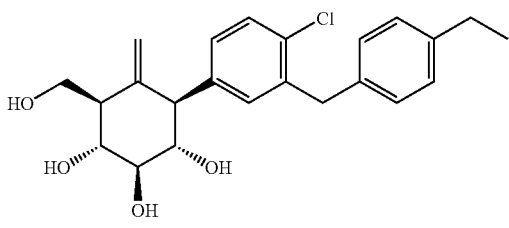

(1R,2R,3S,4S,6R)-4-(4-chloro-3-(4-ethylbenzyl)phenyl)-6-(hydroxymethyl)-5-methylenecyclohexane-1,2,3-triol

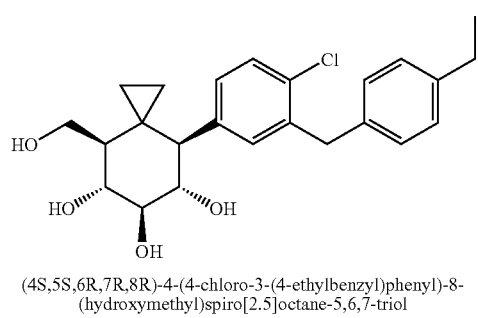

(4S,5S,6R,7R,8R)-4-(4-chloro-3-(4-ethylbenzyl)phenyl)-8-(hydroxymethyl)spiro[2.5]octane-5,6,7-triol

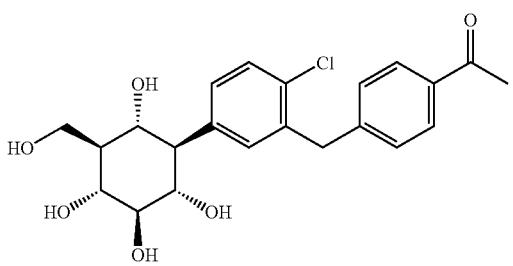

1-(4-(2-chloro-5-((1R,2S,3R,4R,5S,6R)-2,3,4,6-tetrahydroxy-5-(hydroxymethyl)cyclohexyl)benzyl)phenyl)ethanone and -continued

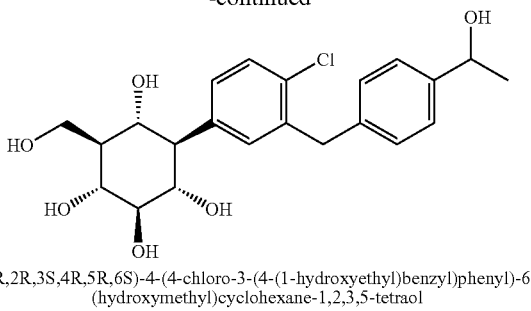

(1R,2R,3S,4R,5R,6S)-4-(4-chloro-3-(4-(1-hydroxyethyl)benzyl)phenyl)-6-(hydroxymethyl)cyclohexane-1,2,3,5-tetraol In another aspect, the present invention includes the compounds of Formula I and pharmaceutically acceptable salts, prodrugs and/or isotopically labeled compounds thereof, wherein alkyl, alkenyl, alkynyl, cycloalkyl, cycloalkenyl, aryl and heteroaryl groups or portions are optionally substituted with one to three suitable substituents as defined above.

In other aspects, the present invention provides intermediates and processes useful for preparing the intermediates below as well as the compounds of Formula I, and pharmaceutically acceptable salts and prodrugs thereof.

Such processes are outlined in the following general preparative methods depicted in the schemes of FIGS. 1 and 2, with more detailed particular examples being presented below in the experimental section describing the working examples (FIGS. 3-8). By following the general preparative methods discussed below, or employing variations or alternative methods, the compounds of the invention can be readily prepared by the use of chemical reactions and procedures known to those of skill in the art. Unless otherwise specified, the variables (e.g., R groups) denoting groups in the general methods described below have the meanings as hereinbefore defined.

Those of skill in the art will recognize that compounds of the invention with each described functional group are generally prepared using slight variations of the below-listed general methods. Within the scope of each method, functional groups which are suitable to the reaction conditions are used. Functional groups which might interfere with certain reactions are presented in protected forms where necessary, and the removal of such protective groups is completed at appropriate stages by methods well known to those skilled in the art.

In certain cases compounds of the invention can be prepared from other compounds of the invention by elaboration, transformation, exchange and the like of the functional groups present. Such elaboration includes, but is not limited to, hydrolysis, reduction, oxidation, alkylation, acylation, esterification, amidation and dehydration. Such transformations can in some instances require the use of protecting groups by the methods disclosed in T. W. Greene and P. G. M. Wuts, *Protective Groups in Organic Synthesis*, 4$^{th}$ Edition; Wiley: New York, (2007) and P. J. Kocienski, *Protecting Groups*, 3$^{rd}$ Edition; Georg Thieme Verlag: Stuttgart, (2005), both of which are incorporated herein by reference. Such methods would be initiated after synthesis of the desired compound or at another place in the synthetic route that would be readily apparent to one skilled in the art.

In another aspect, the present invention provides for synthetic intermediates useful for preparing the compounds of Formula I, and pharmaceutically acceptable salts and prodrugs thereof, according to the general preparative methods discussed below and other processes known to those of skill in the art.

When the following abbreviations and acronyms are used throughout the disclosure, they have the following meanings: $Ac_2O$, acetic anhydride; AcOEt, ethyl acetate; AcOH, acetic acid; $AlBr_3$, aluminum bromide; $AlCl_3$, aluminum chloride; $BBr_3$, boron tribromide; $BF_3.Et_2O$, boron trifluoride etherate; n-BuLi, n-butyllithium; s-BuLi, s-butyllithium; t-BuLi, t-butyllithium; t-BuOK, potassium tert-butoxide; $CaCl_2$, calcium chloride; calc., calculated; $CD_3OD$, methanol-$d_4$; $CDCl_3$, chloroform-d; $CF_3SO_3H$, trifluoromethanesulfonic acid; $CH_2Cl_2$, methylene chloride; $CH_2I_2$, methylene iodide; $CH_3CN$, acetonitrile; $(COCl)_2$, oxalyl chloride; DAST, (diethylamino)sulfur trifluoride; DCM, dichloromethane; DIAD, diisopropyl azodicarboxylate; DMAP, 4-dimethylaminopyridine; DMEM, Dulbecco's Modified Eagle Medium; DMF, N,N-dimethylformamide; DMP, Dess-Martin periodinane; DMSO, dimethylsulfoxide; EA, ethyl acetate; eq, equivalents; ESI, electrospray ionization; Et, ethyl; $Et_3SiH$, triethylsilane; EtOAc, ethyl acetate; EtOH, ethanol; FBS, fetal bovine serum; h, hour; $H_2$, hydrogen gas; $H_2SO_4$, sulfuric acid; Hepes, 4-(2-hydroxyethyl)-1-piperazineethanesulfonic acid; $^1$H NMR, proton nuclear magnetic resonance; HPLC, high performance liquid chromatography; $K_2CO_3$, potassium carbonate; $K_2CrO_7$, potassium dichromate; KOH, potassium hydroxide; LC-ESI-MS, liquid chromatography electrospray ionization mass spectrometry; LC-MS, liquid chromatography-mass spectroscopy; Me, methyl; MeOH, methanol; $MeSO_3H$, methanesulfonic acid; Mg, magnesium; $MgCl_2$, magnesium chloride; min, minute; MS, mass spectroscopy; MsOH, methanesulfonic acid; NaH, sodium hydride; $NaHCO_3$, sodium bicarbonate; NaOAc, sodium acetate; NaOH, sodium hydroxide; $Na_2SO_4$, sodium sulfate; $NH_4Cl$, ammonium chloride; Pd/C, palladium on carbon; PE, petroleum ether; Ph, phenyl; $POCl_3$, phosphorus oxychloride; $PPh_3$, triphenylphosphine; $R_f$, retention factor; rt, room temperature; $SOCl_2$, thionyl chloride; TBAI, tetrabutylammonium iodide; TFA, trifluoroacetic acid; THF, tetrahydrofuran; TLC, thin layer chromatography; TMS, trimethylsilyl; Tris, trishydroxymethylaminomethane (or 2-amino-2-(hydroxymethyl)propane-1,3-diol).

General Synthesis Method of Scheme I

Inventive compounds of Formula I can be conveniently prepared according to the reaction sequences as shown in Scheme I (FIG. 1).

As shown in Scheme I, acid A1, either commercially available or prepared according to standard literature methods, is converted to acid chloride A2 by an acylation agent such as oxalyl chloride, $SOCl_2$ or $POCl_3$, etc. Acid chloride A2 is reacted with substituted benzene A3 in the presence of a Lewis acid, such as $AlCl_3$ or $AlBr_3$, to provide ketone A4. The ketone group of intermediate A4 is selectively reduced to methylene with a reducing agent such as $Et_3SiH$ in the presence of a Lewis acid such as $BF_3.Et_2O$ or TFA. Treatment of A5 with an activating agent such as n-BuLi, s-BuLi or t-BuLi, or Mg at appropriate temperature in a solvent such as THF, followed by addition to intermediate A6, provides intermediate A7. Intermediate A8 is obtained by treatment of A7 with a reducing agent such as $Et_3SiH$ in the presence of a Lewis acid such as $BF_3.Et_2O$ or TFA. Then A8 is oxidized to form intermediate A9, which is deprotected to provide inventive compound A10. Alternatively, A11 can also be prepared by oxidation of intermediate A9.

General Synthesis Method of Scheme II

Figure 2:
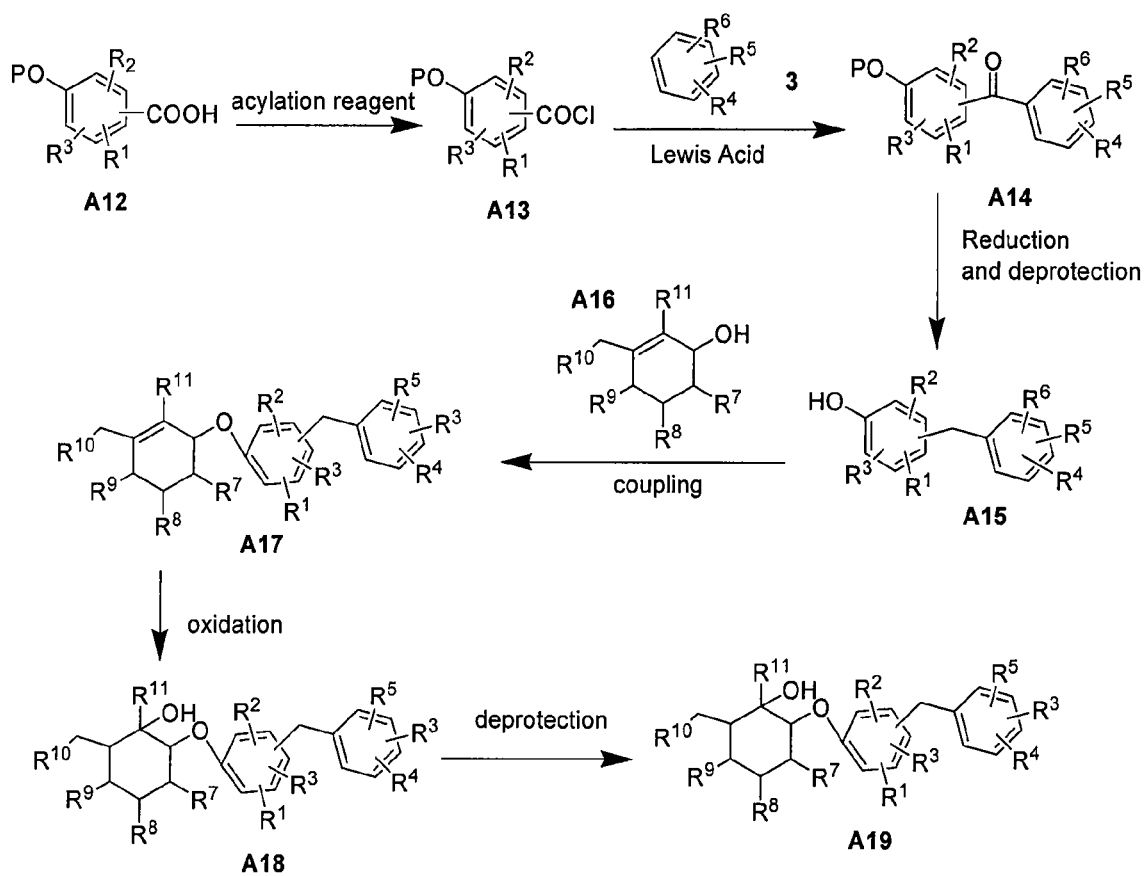

Inventive compounds of Formula I can also be conveniently prepared according to a reaction sequence as shown in Scheme II (FIG. 2).

As shown in Scheme II, acid A12, either commercially available or prepared according to standard literature methods, is converted to acid chloride A13 by an acylation agent such as oxalyl chloride, $SOCl_2$ or $POCl_3$, etc. Acid chloride A13 is reacted with substituted benzene A3 in the presence of Lewis acid, such as $AlCl_3$ or $AlBr_3$, to provide ketone A14. The ketone group of intermediate A14 is selectively reduced to methylene with a reducing agent such as $Et_3SiH$ in the presence of a Lewis acid such as $BF_3.Et_2O$ or TFA, and then deprotection gives the intermediate A15. Coupling of A15 with A16 provides intermediate A17. Oxidation of A17 produces intermediate A18, which then is deprotected to provide inventive compound A19.

Pharmaceutical Compositions and Methods of Use

The present invention further provides a pharmaceutical composition comprising an effective amount of a compound or mixture of compounds of Formula I, or a pharmaceutically acceptable salt or prodrug thereof, in a pharmaceutically acceptable carrier.

A compound of this invention can be incorporated into a variety of formulations for therapeutic administration. More particularly, a compound of the present invention can be formulated into pharmaceutical compositions, together or separately, by formulation with appropriate pharmaceutically acceptable carriers or diluents, and can be formulated into preparations in solid, semi-solid, liquid or gaseous forms, such as tablets, capsules, pills, powders, granules, dragees, gels, slurries, ointments, solutions, suppositories, injections, inhalants and aerosols. As such, administration of a compound of the present invention can be achieved in various ways, including oral, buccal, parenteral, intravenous, intradermal (e.g., subcutaneous, intramuscular), transdermal, etc., administration. Moreover, the compound can be administered in a local rather than systemic manner, for example, in a depot or sustained release formulation.

Suitable formulations for use in the present invention are found in Remington: The Science and Practice of Pharmacy, 21$^{st}$ Ed., Gennaro, Ed., Lippencott Williams & Wilkins (2003), which is hereby incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

In one preferred embodiment, a compound of the present invention is prepared for delivery in a sustained-release, controlled release, extended-release, timed-release or delayed-release formulation, for example, in semipermeable matrices of solid hydrophobic polymers containing the therapeutic agent. Various types of sustained-release materials have been established and are well known by those skilled in the art. Current extended-release formulations include film-coated tablets, multiparticulate or pellet systems, matrix technologies using hydrophilic or lipophilic materials and wax-based tablets with pore-forming excipients (see, for example, Huang, et al. Drug Dev. Ind. Pharm. 29:79 (2003); Pearnchob, et al. Drug Dev. Ind. Pharm. 29:925 (2003); Maggi, et al. Eur. J. Pharm. Biopharm. 55:99 (2003); Khanvilkar, et al., Drug Dev. Ind. Pharm. 228:601 (2002); and Schmidt, et al., Int. J. Pharm. 216:9 (2001)). Sustained-release delivery systems can, depending on their design, release the compounds over the course of hours or days, for instance, over 4, 6, 8, 10, 12, 16, 20, 24 hours or more. Usually, sustained release formulations can be prepared using naturally-occurring or synthetic polymers, for instance, polymeric vinyl pyrrolidones, such as polyvinyl pyrrolidone (PVP); carboxyvinyl hydrophilic polymers; hydrophobic and/or hydrophilic hydrocolloids, such as methylcellulose, ethylcellulose, hydroxypropylcellulose, and hydroxypropylmethylcellulose; and carboxypolymethylene.

The sustained or extended-release formulations can also be prepared using natural ingredients, such as minerals, including titanium dioxide, silicon dioxide, zinc oxide, and clay (see, U.S. Pat. No. 6,638,521, herein incorporated by reference). Exemplified extended release formulations that can be used in delivering a compound of the present invention include those described in U.S. Pat. Nos. 6,635,680; 6,624,200; 6,613,361; 6,613,358, 6,596,308; 6,589,563; 6,562,375; 6,548,084; 6,541,020; 6,537,579; 6,528,080 and 6,524,621, each of which is hereby incorporated herein by reference. Controlled release formulations of particular interest include those described in U.S. Pat. Nos. 6,607,751; 6,599,529; 6,569,463; 6,565,883; 6,482,440; 6,403,597; 6,319,919; 6,150,354; 6,080,736; 5,672,356; 5,472,704; 5,445,829; 5,312,817 and 5,296,483, each of which is hereby incorporated herein by reference. Those skilled in the art will readily recognize other applicable sustained release formulations.

For oral administration, a compound of the present invention can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as a cross-linked polyvinyl pyrrolidone, agar, or alginic acid or a salt thereof such as sodium alginate.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

The compounds can be formulated for parenteral administration by injection, e.g., by bolus injection or continuous infusion. For injection, the compound can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, a compound of the invention can be formulated in aqueous solutions, preferably in physiologically compatible buffers such as Hanks's solution, Ringer's solution, or physiological saline buffer. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

Systemic administration can also be by transmucosal or transdermal means. For transmucosal or transdermal administration, penetrants appropriate to the barrier to be permeated are used in the formulation. For topical administration, the agents are fonnulated into ointments, creams, salves, powders and gels. In one embodiment, the transdermal delivery agent can be DMSO. Transdermal delivery systems can include, e.g., patches. For transmucosal administration, penetrants appropriate to the barrier to be permeated are used in the formulation. Such penetrants are generally known in the art. Exemplified transdermal delivery formulations that can find use in the present invention include those described in U.S. Pat. Nos. 6,589,549; 6,544,548; 6,517,864; 6,512,010; 6,465,006; 6,379,696; 6,312,717 and 6,310,177, each of which are hereby incorporated herein by reference.

For buccal administration, the compositions can take the form of tablets or lozenges fonnulated in conventional manner.

In addition to the formulations described previously, a compound of the present invention can also be formulated as a depot preparation. Such long acting formulations can be administered by implantation (for example subcutaneously or intramuscularly) or by intramuscular injection. Thus, for example, the compounds can be fonnulated with suitable polymeric or hydrophobic materials (for example as an emulsion in an acceptable oil) or ion exchange resins, or as sparingly soluble derivatives, for example, as a sparingly soluble salt.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in a therapeutically effective amount. The present invention also contemplates pharmaceutical compositions comprising the compounds of Formula I in admixture with an effective amount of other therapeutic agents as combination partners, particularly those used for treating diseases and conditions which can be affected by SGLT inhibition, such as antidiabetic agents, lipid-lowering/lipid-modulating agents, agents for treating diabetic complications, anti-obesity agents, antihypertensive agents, antihyperuricemic agents, and agents for treating chronic heart failure, atherosclerosis or related disorders. An effective amount of the compound and/or combination partner will, of course, be dependent on the subject being treated, the severity of the affliction and the manner of administration. Determination of an effective amount is well within the capability of those skilled in the art, especially in light of the detailed disclosure provided herein. Generally, an efficacious or effective amount of a compound is determined by first administering a low dose or small amount, and then incrementally increasing the administered dose or dosages until a desired therapeutic effect is observed in the treated subject, with minimal or no toxic side effects. Applicable methods for determining an appropriate dose and dosing schedule for administration of the present invention are described, for example, in *Goodman and Gilman's The Pharmacological Basis of Therapeutics*, 11$^{th}$ Ed., Brunton, Lazo and Parker, Eds., McGraw-Hill (2006), and in *Remington: The Science and Practice of Pharmacy*, 21$^{st}$ Ed., Gennaro, Ed., Lippencott Williams & Wilkins (2003), both of which are hereby incorporated herein by reference.

The present invention further provides methods of using the compounds of Formula I for the prevention and treatment of disease. In one embodiment the invention provides a method of treating type 1 and type 2 diabetes mellitus, hyperglycemia, diabetic complications (such as retinopathy, nephropathy, neuropathy, ulcers, micro- and macroangiopathies, gout and diabetic foot disease), insulin resistance, metabolic syndrome (Syndrome X), hyperinsulinemia, hypertension, hyperuricemia, obesity, edema, dyslipidemia, chronic heart failure, atherosclerosis and related diseases, which comprises administering an effective amount of a compound or mixture of compounds of Formula I, or a pharmaceutically acceptable salt or prodrug thereof, to a subject in need thereof. In another embodiment the invention provides a method of using a compound or mixture of compounds of Formula I, or a pharmaceutically acceptable salt or prodrug thereof, for the preparation of a medicament for treating type 1 and type 2 diabetes mellitus, hyperglycemia, diabetic complications, insulin resistance, metabolic syndrome, hyperinsulinemia, hypertension, hyperuricemia, obesity, edema, dyslipidemia, chronic heart failure, atherosclerosis and related diseases.

The present invention also contemplates the use of the compounds of Formula I, or pharmaceutically acceptable salts or prodrugs thereof, in combination with other therapeutic agents, particularly those used for treating the above-mentioned diseases and conditions, such as antidiabetic agents, lipid-lowering/lipid-modulating agents, agents for treating diabetic complications, anti-obesity agents, antihypertensive agents, antihyperuricemic agents, and agents for treating chronic heart failure, atherosclerosis or related disorders. Those skilled in the art will appreciate that other therapeutic agents discussed below can have multiple therapeutic uses and the listing of an agent in one particular category should not be construed to limit in any way its usefulness in combination therapy with compounds of the present invention.

Examples of antidiabetic agents suitable for use in combination with compounds of the present invention include insulin and insulin mimetics, sulfonylureas (such as acetohexamide, carbutamide, chlorpropamide, glibenclamide, glibornuride, gliclazide, glimepiride, glipizide, gliquidone, glisoxepide, glyburide, glyclopyramide, tolazamide, tolcyclamide, tolbutamide and the like), insulin secretion enhancers (such as JTT-608, glybuzole and the like), biguanides (such as metformin, buformin, phenformin and the like), sulfonylurea/biguanide combinations (such as glyburide/metformin and the like), meglitinides (such as repaglinide, nateglinide, mitiglinide and the like), thiazolidinediones (such as rosiglitazone, pioglitazone, isaglitazone, netoglitazone, rivoglitazone, balaglitazone, darglitazone, CLX-0921 and the like), thiazolidinedione/biguanide combinations (such as pioglitazone/metformin and the like), oxadiazolidinediones (such as YM440 and the like), peroxisome proliferator-activated receptor (PPAR)-gamma agonists (such as farglitazar, metaglidasen, MBX-2044, GI 262570, GW1929, GW7845 and the like), PPAR-alpha/gamma dual agonists (such as muraglitazar, naveglitazar, tesaglitazar, peliglitazar, JTT-501, GW-409544, GW-501516 and the like), PPAR-alpha/gamma/delta pan agonists (such as PLX204, GlaxoSmithKline 625019, GlaxoSmithKline 677954 and the like), retinoid X receptor agonists (such as ALRT-268, AGN-4204, MX-6054, AGN-194204, LG-100754, bexarotene and the like), alpha-glucosidase inhibitors (such as acarbose, miglitol and the like), stimulants of insulin receptor tyrosine kinase (such as TER-17411, L-783281, KRX-613 and the like), tripeptidyl peptidase II inhibitors (such as UCL-1397 and the like), dipeptidyl peptidase IV inhibitors (such as sitagliptin, vildagliptin, denagliptin, saxagliptin, NVP-DPP728, P93/01, P32/98, FE 99901, TS-021, TSL-225, GRC8200, compounds described in U.S. Pat. Nos. 6,869,947; 6,727,261; 6,710,040; 6,432,969; 6,172,081; 6,011,155 and the like), protein tyrosine phosphatase-1B inhibitors (such as KR61639, IDD-3, PTP-3848, PTP-112, OC-86839, PNU-177496, compounds described in Vats, R. K., et al., *Current Science*, Vol. 88, No. 2, 25 Jan. 2005, pp. 241-249, and the like), glycogen phosphorylase inhibitors (such as NN-4201, CP-368296 and the like), glucose-6-phosphatase inhibitors, fructose 1,6-bis-phosphatase inhibitors (such as CS-917, MB05032 and the like), pyruvate dehydrogenase inhibitors (such as AZD-7545 and the like), imidazoline derivatives (such as BL11282 and the like), hepatic gluconeogenesis inhibitors (such as FR-225659 and the like), D-chiroinositol, glycogen synthase kinase-3 inhibitors (such as compounds described in Vats, R. K., et al., *Current Science*, Vol. 88, No. 2, 25 Jan. 2005, pp. 241-249, and the like), incretin mimetics (such as exenatide and the like), glucagon receptor antagonists (such as BAY-27-9955, NN-2501, NNC-92-1687 and the like), glucagon-like peptide-1 (GLP-1), GLP-1 analogs (such as liraglutide, CJC-1131, AVE-0100 and the like), GLP-1 receptor agonists (such as AZM-134, LY-315902, GlaxoSmithKline 716155 and the like), amylin, amylin analogs and agonists (such as pramlintide and the like), fatty acid binding protein (aP2) inhibitors (such as compounds described in U.S. Pat. Nos. 6,984,645; 6,919,323; 6,670,380; 6,649,622; 6,548,529 and the like), beta-3 adrenergic receptor agonists (such as solabegron, CL-316243, L-771047, FR-149175 and the like), and other insulin sensitivity enhancers (such as reglixane, ONO-5816, MBX-102, CRE-1625, FK-614, CLX-0901, CRE-1633, NN-2344, BM-13125, BM-501050, HQL-975, CLX-0900, MBX-668, MBX-675, S-15261, GW-544, AZ-242, LY-510929, AR-H049020, GW-501516 and the like).

Examples of agents for treating diabetic complications suitable for use in combination with compounds of the present invention include aldose reductase inhibitors (such as epalrestat, imirestat, tolrestat, minalrestat, ponalrestat, zopolrestat, fidarestat, ascorbyl gamolenate, ADN-138, BAL-ARI8, ZD-5522, ADN-311, GP-1447, IDD-598, risarestat, zenarestat, methosorbinil, AL-1567, M-16209, TAT, AD-5467, AS-3201, NZ-314, SG-210, JTT-811, lindolrestat, sorbinil and the like), inhibitors of advanced glycation end-products (AGE) formation (such as pyridoxamine, OPB-9195, ALT-946, ALT-711, pimagedine and the like), AGE breakers (such as ALT-711 and the like), sulodexide, 5-hydroxy-1-methylhydantoin, insulin-like growth factor-I, platelet-derived growth factor, platelet-derived growth factor analogs, epidermal growth factor, nerve growth factor, uridine, protein kinase C inhibitors (such as ruboxistaurin, midostaurin and the like), sodium channel antagonists (such as mexiletine, oxcarbazepine and the like), nuclear factor-kappaB (NF-kappaB) inhibitors (such as dexlipotam and the like), lipid peroxidase inhibitors (such as tirilazad mesylate and the like), N-acetylated-alpha-linked-acid-dipeptidase inhibitors (such as GPI-5232, GPI-5693 and the like), and carnitine derivatives (such as carnitine, levacecamine, levocarnitine, ST-261 and the like).

Examples of antihyperuricemic agents suitable for use in combination with compounds of the present invention include uric acid synthesis inhibitors (such as allopurinol, oxypurinol and the like), uricosuric agents (such as probenecid, sulfinpyrazone, benzbromarone and the like) and urinary alkalinizers (such as sodium hydrogen carbonate, potassium citrate, sodium citrate and the like).

Examples of lipid-lowering/lipid-modulating agents suitable for use in combination with compounds of the present invention include hydroxymethylglutaryl coenzyme A reductase inhibitors (such as acitemate, atorvastatin, bervastatin, carvastatin, cerivastatin, colestolone, crilvastatin, dalvastatin, fluvastatin, glenvastatin, lovastatin, mevastatin, nisvastatin, pitavastatin, pravastatin, ritonavir, rosuvastatin, saquinavir, simvastatin, visastatin, SC-45355, SQ-33600, CP-83101, BB-476, L-669262, S-2468, DMP-565, U-20685, BMS-180431, BMY-21950, compounds described in U.S. Pat. Nos. 5,753,675; 5,691,322; 5,506,219; 4,686,237; 4,647,576; 4,613,610; 4,499,289 and the like), fibric acid derivatives (such as gemfibrozil, fenofibrate, bezafibrate, beclobrate, binifibrate, ciprofibrate, clinofibrate, clofibrate, etofibrate, nicofibrate, pirifibrate, ronifibrate, simfibrate, theofibrate, AHL-157 and the like), PPAR-alpha agonists (such as GlaxoSmithKline 590735 and the like), PPAR-delta agonists (such as GlaxoSmithKline 501516 and the like), acyl-coenzyme A:cholesterol acyltransferase inhibitors (such as avasimibe, eflucimibe, eldacimibe, lecimibide, NTE-122, MCC-147, PD-132301-2, C1-1011, DUP-129, U-73482, U-76807, TS-962, RP-70676, P-06139, CP-113818, RP-73163, FR-129169, FY-038, EAB-309, KY-455, LS-3115, FR-145237, T-2591, J-104127, R-755, FCE-27677, FCE-28654, YIC-C8-434, CI-976, RP-64477, F-1394, CS-505, CL-283546, YM-17E, 447C88, YM-750, E-5324, KW-3033, HL-004 and the like), probucol, thyroid hormone receptor agonists (such as liothyronine, levothyroxine, KB-2611, GC-1 and the like), cholesterol absorption inhibitors (such as ezetimibe, SCH48461 and the like), lipoprotein-associated phospholipase A2 inhibitors (such as rilapladib, darapladib and the like), microsomal triglyceride transfer protein inhibitors (such as CP-346086, BMS-201038, compounds described in U.S. Pat. Nos. 5,595,872; 5,739,135; 5,712,279; 5,760,246; 5,827,875; 5,885,983; 5,962,440; 6,197,798; 6,617,325; 6,821,967; 6,878,707 and the like), low density lipoprotein receptor activators (such as LY295427, MD-700 and the like), lipoxygenase inhibitors (such as compounds described in WO 97/12615, WO 97/12613, WO 96/38144 and the like), carnitine palmitoyl-transferase inhibitors (such as etomoxir and the like), squalene synthase inhibitors (such as YM-53601, TAK-475, SDZ-268-198, BMS-188494, A-87049, RPR-101821, ZD-9720, RPR-107393, ER-27856, compounds described in U.S. Pat. Nos. 5,712,396; 4,924,024; 4,871,721 and the like), nicotinic acid derivatives (such as acipimox, nicotinic acid, ricotinamide, nicomol, niceritrol, nicorandil and the like), bile acid sequestrants (such as colestipol, cholestyramine, colestilan, colesevelam, GT-102-279 and the like), sodium/bile acid cotransporter inhibitors (such as 264W94, S-8921, SD-5613 and the like), and cholesterol ester transfer protein inhibitors (such as torcetrapib, JTT-705, PNU-107368E, SC-795, CP-529414 and the like).

Examples of anti-obesity agents suitable for use in combination with compounds of the present invention include serotonin-norepinephrine reuptake inhibitors (such as sibutramine, milnacipran, mirtazapine, venlafaxine, duloxetine, desvenlafaxine and the like), norepinephrine-dopamine reuptake inhibitors (such as radafaxine, bupropion, amineptine and the like), serotonin-norepinephrine-dopamine reuptake inhibitors (such as tesofensine and the like), selective serotonin reuptake inhibitors (such as citalopram, escitalopram, fluoxetine, fluvoxamine, paroxetine, sertraline and the like), selective norepinephrine reuptake inhibitors (such as reboxetine, atomoxetine and the like), norepinephrine releasing stimulants (such as rolipram, YM-992 and the like), anorexiants (such as amphetamine, methamphetamine, dextroamphetamine, phentermine, benzphetamine, phendimetrazine, phenmetrazine, diethylpropion, mazindol, fenfluramine, dexfenfluramine, phenylpropanolamine and the like), dopamine agonists (such as ER-230, doprexin, bromocriptine mesylate and the like), $H_3$-histamine antagonists (such as impentamine, thioperamide, ciproxifan, clobenpropit, GT-2331, GT-2394, A-331440, and the like), 5-HT2c receptor agonists (such as, 1-(m-chlorophenyl)piperazine (m-CPP), mirtazapine, APD-356 (lorcaserin), SCA-136 (vabicaserin), ORG-12962, ORG-37684, ORG-36262, ORG-8484, Ro-60-175, Ro-60-0332, VER-3323, VER-5593, VER-5384, VER-8775, LY-448100, WAY-161503, WAY-470, WAY-163909, MK-212, BVT.933, YM-348, IL-639, IK-264, ATH-88651, ATHX-105 and the like (see, e.g., Nilsson B M, *J. Med. Chem.* 2006, 49:4023-4034)), beta-3 adrenergic receptor agonists (such as L-796568, CGP 12177, BRL-28410, SR-58611A, ICI-198157, ZD-2079, BMS-194449, BRL-37344, CP-331679, CP-331648, CP-114271, L-750355, BMS-187413, SR-59062A, BMS-210285, LY-377604, SWR-0342SA, AZ-40140, SB-226552, D-7114, BRL-35135, FR-149175, BRL-26830A, CL-316243, AJ-9677, GW-427353, N-5984, GW-2696 and the like), cholecystokinin agonists (such as SR-146131, SSR-125180, BP-3.200, A-71623, A-71378, FPL-15849, GI-248573, GW-7178, GI-181771, GW-7854, GW-5823, and the like), antidepressant/acetylcholinesterase inhibitor combinations (such as venlafaxine/rivastigmine, sertraline/galanthamine and the like), lipase inhibitors (such as orlistat, ATL-962 and the like), anti-epileptic agents (such as topiramate, zonisamide and the like), leptin, leptin analogs and leptin receptor agonists (such as LY-355101 and the like), neuropeptide Y (NPY) receptor antagonists and modulators (such as SR-120819-A, PD-160170, NGD-95-1, BIBP-3226, 1229-U-91, CGP-71683, BIBO-3304, CP-671906-01, J-115814 and the like), ciliary neurotrophic factor (such as Axokine and the like), thyroid hormone receptor-beta agonists (such as KB-141, GC-1, GC-24, GB98/284425 and the like), cannabinoid CB1 receptor antagonists (such as rimonabant, SR147778, SLV 319 and the like (see, e.g., Antel J et al., *J. Med. Chem.* 2006, 49:4008-4016)), melanin-concentrating hormone receptor antagonists (such as GlaxoSmithKline 803430X, GlaxoSmithKline 856464, SNAP-7941, T-226296 and the like (see, e.g., Handlon A L and Zhou H, *J. Med. Chem.* 2006, 49:4017-4022)), melanocortin-4 receptor agonists (including PT-15, Ro27-3225, THIQ, NBI 55886, NBI 56297, NBI 56453, NBI 58702, NBI 58704, MB243 and the like (see, e.g., Nargund R P et al., *J. Med. Chem.* 2006, 49:4035-4043)), selective muscarinic receptor $M_1$ antagonists (such as telenzepine, pirenzepine and the like), opioid receptor antagonists (such as naltrexone, methylnaltrexone, nalmefene, naloxone, alvimopan, norbinaltorphimine, nalorphine and the like), and combinations thereof.

Examples of antihypertensive agents and agents for treating chronic heart failure, atherosclerosis or related diseases suitable for use in combination with compounds of the present invention include bimoclomol, angiotensin-converting enzyme inhibitors (such as captopril, enalapril, fosinopril, lisinopril, perindopril, quinapril, ramipril and the like), neutral endopeptidase inhibitors (such as thiorphan, omapatrilat, MDL-100240, fasidotril, sampatrilat, GW-660511, mixanpril, SA-7060, E-4030, SLV-306, ecadotril and the like), angiotensin II receptor antagonists (such as candesartan cilexetil, eprosartan, irbesartan, losartan, olmesartan medoxomil, telmisartan, valsartan, tasosartan, enoltasosartan and the like), endothelin-converting enzyme inhibitors (such as CGS 35066, CGS 26303, CGS-31447, SM-19712 and the like), endothelin receptor antagonists (such as tracleer, sitaxsentan, ambrisentan, L-749805, TBC-3214, BMS-182874, BQ-610, TA-0201, SB-215355, PD-180988, BMS-193884, darusentan, TBC-3711, bosentan, tezosentan, J-104132, YM-598, S-0139, SB-234551, RPR-118031A, ATZ-1993, RO-61-1790, ABT-546, enlasentan, BMS-207940 and the like), diuretic agents (such as hydrochlorothiazide, bendroflumethiazide, trichlormethiazide, indapamide, metolazone, furosemide, bumetanide, torsemide, chlorthalidone, metolazone, cyclopenthiazide, hydroflumethiazide, tripamide, mefruside, benzylhydrochlorothiazide, penflutizide, methyclothiazide, azosemide, etacrynic acid, torasemide, piretanide, meticrane, potassium canrenoate, spironolactone, triamterene, aminophylline, cicletanine, LLU-alpha, PNU-80873A, isosorbide, D-mannitol, D-sorbitol, fructose, glycerin, acetazolamide, methazolamide, FR-179544, OPC-31260, lixivaptan, conivaptan and the like), calcium channel antagonists (such as amlodipine, bepridil, diltiazem, felodipine, isradipine, nicardipen, nimodipine, verapamil, S-verapamil, aranidipine, efonidipine, barnidipine, benidipine, manidipine, cilnidipine, nisoldipine, nitrendipine, nifedipine, nilvadipine, felodipine, pranidipine, lercanidipine, isradipine, elgodipine, azelnidipine, lacidipine, vatanidipine, lemildipine, diltiazem, clentiazem, fasudil, bepridil, gallopamil and the like), vasodilating antihypertensive agents (such as indapamide, todralazine, hydralazine, cadralazine, budralazine and the like), beta blockers (such as acebutolol, bisoprolol, esmolol, propanolol, atenolol, labetalol, carvedilol, metoprolol and the like), sympathetic blocking agents (such as amosulalol, terazosin, bunazosin, prazosin, doxazosin, propranolol, atenolol, metoprolol, carvedilol, nipradilol, celiprolol, nebivolol, betaxolol, pindolol, tertatolol, bevantolol, timolol, carteolol, bisoprolol, bopindolol, nipradilol, penbutolol, acebutolol, tilisolol, nadolol, urapidil, indoramin and the like), alpha-2-adrenoceptor agonists (such as clonidine, methyldopa, CHF-1035, guanabenz acetate, guanfacine, moxonidine, lofexidine, talipexole and the like), centrally acting antihypertensive agents (such as reserpine and the like), thrombocyte aggregation inhibitors (such as warfarin, dicumarol, phenprocoumon, acenocoumarol, anisindione, phenindione, ximelagatran and the like), and anti-platelets agents (such as aspirin, clopidogrel, ticlopidine, dipyridamole, cilostazol, ethyl icosapentate, sarpogrelate, dilazep, trapidil, beraprost and the like).

Furthermore, in another aspect, the invention provides for a pharmaceutical composition comprising effective amounts of a compound or mixture of compounds of Formula I, or a pharmaceutically acceptable salt or prodrug thereof, and at least one member selected from the group of therapeutic agents listed above as combination partners, in a pharmaceutically acceptable carrier.

The treatment of the present invention can be administered prophylactically to prevent or delay the onset or progression of a disease or condition (such as hyperglycemia), or therapeutically to achieve a desired effect (such as a desired level of serum glucose) for a sustained period of time.

The compounds of the present invention can be administered to a subject, e.g., a human patient, a domestic animal such as a cat or a dog, independently or together with a combination partner, in the form of their pharmaceutically acceptable salts or prodrugs, or in the form of a pharmaceutical composition where the compounds and/or combination partners are mixed with suitable carriers or excipient(s) in a therapeutically effective amount. Consequently, a compound or mixture of compounds of Formula I, or a pharmaceutically acceptable salt or prodrug thereof, and an additional active agent to be combined therewith, can be present in a single formulation, for example a capsule or tablet, or in two separate formulations, which can be the same or different, for example, in the form of a kit comprising selected numbers of doses of each agent.

The appropriate dosage of compound will vary according to the chosen route of administration and formulation of the composition, among other factors, such as patient response. The dosage can be increased or decreased over time, as required by an individual patient. A patient initially may be given a low dose, which is then increased to an efficacious dosage tolerable to the patient. Typically, a useful dosage for adults may be from 1 to 2000 mg, preferably 1 to 200 mg, when administered by oral route, and from 0.1 to 100 mg, preferably 1 to 30 mg, when administered by intravenous route, in each case administered from 1 to 4 times per day. When a compound of the invention is administered in combination with another therapeutic agent, a useful dosage of the combination partner may be from 20% to 100% of the nonnally recommended dose.

Dosage amount and interval can be adjusted individually to provide plasma levels of the active compounds which are sufficient to maintain therapeutic effect. Preferably, therapeutically effective serum levels will be achieved by administering single daily doses, but efficacious multiple daily dose schedules are included in the invention. In cases of local administration or selective uptake, the effective local concentration of the drug may not be related to plasma concentration. One having skill in the art will be able to optimize therapeutically effective local dosages without undue experimentation.

All publications and patent applications cited in this specification are herein incorporated by reference as if each individual publication or patent application were specifically and individually indicated to be incorporated by reference. Any conflict between any reference cited herein and the teaching of this specification is to be resolved in favor of the latter. Similarly, any conflict between an art-recognized definition of a word or phrase and a definition of the word or phrase as provided in this specification is to be resolved in favor of the latter. Although the foregoing invention has been described in some detail by way of illustration and example for purposes of clarity of understanding, it will be readily apparent to those of ordinary skill in the art in light of the teachings of this invention that certain changes and modifications can be made thereto without departing from the spirit or scope of the appended claims. The invention will be described in greater detail by way of specific examples.

EXAMPLES

The following examples are offered for illustrative purposes, and are not intended to limit the invention in any manner. Those of skill in the art will readily recognize a variety of noncritical parameters which can be changed or modified to yield essentially the same results.

The names of compounds shown in the following examples were derived from the structures shown using the CambridgeSoft Struct=Name algorithm as implemented in ChemDraw Ultra version 10.0. Unless otherwise indicated, the structures of compounds synthesized in the examples below were confirmed using the following procedures:

(1) Gas chromatography-mass spectra with electrospray ionization (MS ESI) were obtained with an Agilent 5973N mass spectrometer equipped with an Agilent 6890 gas chromatograph with an HP-5 MS column (0.25 μm coating; 30 m×0.25 mm). The ion source was maintained at 230° C. and spectra were scanned from 25-500 amu at 3.09 sec per scan.

(2) High pressure liquid chromatography mass spectra (LC-MS) were obtained using Finnigan Surveyor HPLC equipped with a quaternary pump, a variable wavelength detector set at 254 nm, an XB-C18 column (4.6×50 mm, 5 μm), and a Finnigan LCQ ion trap mass spectrometer with electrospray ionization. Spectra were scanned from 80-2000 amu using a variable ion time according to the number of ions in the source. The eluents were B: acetonitrile and D: water. Gradient elution from 10% to 90% B in 8 min at a flow rate of 1.0 mL/min is used with a final hold at 90% B of 7 min. Total run time is 15 min.

(3) Routine one-dimensional NMR spectroscopy was performed on 400 MHz or 300 MHz Varian Mercury-Plus spectrometers. The samples were dissolved in deuterated solvents obtained from Qingdao Tenglong Weibo Technology Co., Ltd., and transferred to 5 mm ID NMR tubes. The spectra were acquired at 293 K. The chemical shifts were recorded on the ppm scale and were referenced to the appropriate solvent signals, such as 2.49 ppm for DMSO-d6, 1.93 ppm for $CD_3CN$, 3.30 ppm for $CD_3OD$, 5.32 ppm for $CD_2Cl_2$ and 7.26 ppm for $CDCl_3$ for $^1H$ spectra.

Example 1

Figure 3:
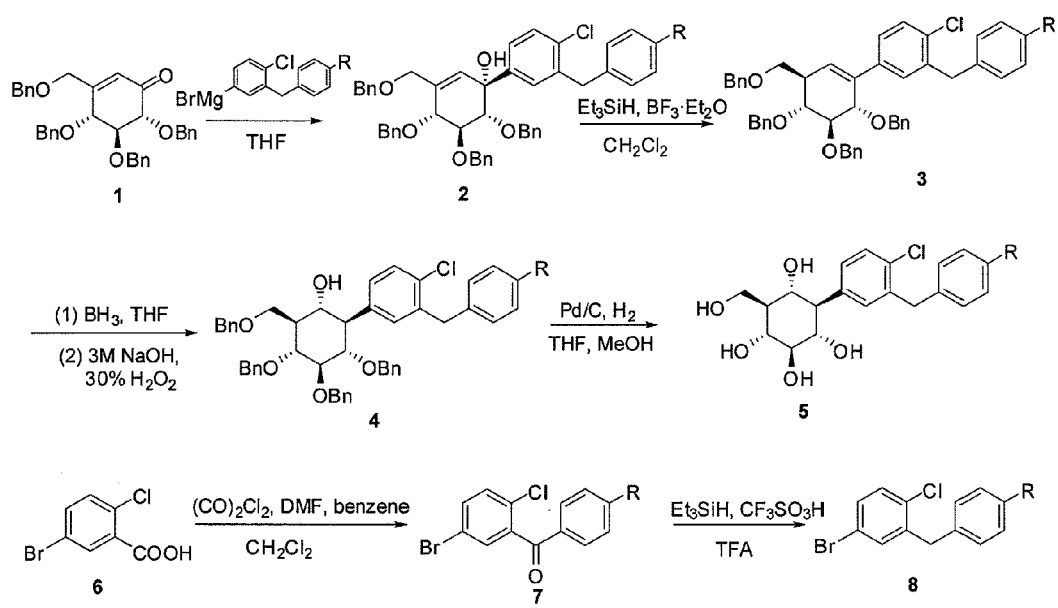
FIGS. 3-8 provide more specific synthesis schemes for compounds in the Examples below.
Figure 3:
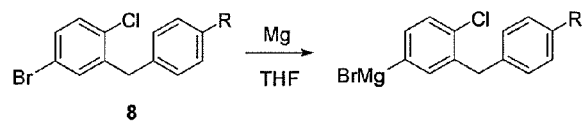

This example illustrates the preparation of compound 5 (R=Et) according to the approach provided in FIG. 3. Compound numbers correspond to those provided in the Figures. The general method is applicable to other compounds of the present invention.

Preparation of (1R,2R,3S,4R,5R,6S)-4-(4-chloro-3-(4-ethylbenzyl)phenyl)-6-(hydroxymethyl)cyclohexane-1,2,3,5-tetraol

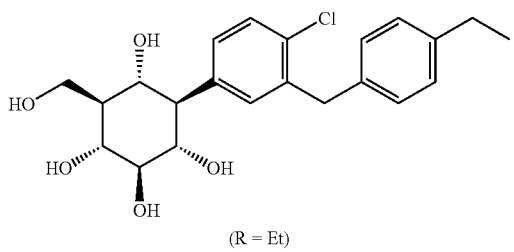

(R = Et)

(1) The Preparation of Grignard Reagent

Under argon, Mg powder (0.216 g, 8.98 mmol, 1.2 eq) was charged into a three-necked flask, followed by addition of a portion of the solution of the 4-bromo-1-chloro-2-(4-ethylbenzyl)benzene 8 (0.769 g, 2.49 mmol) in dry THF (6 mL), and 1,2-dibromoethane (10 mol %). The mixture was heated to reflux. After the reaction was initiated (exothermic and consuming of Mg), the remaining solution of 2-(4-ethylbenzyl)-4-bromo-1-chlorobenzene 8 (1.539 g, 4.99 mmol) in dry THF (14 mL) was added dropwise. The mixture was then allowed to react for another one hour under gently refluxing until most of the Mg was consumed.

(2) The Preparation of 2

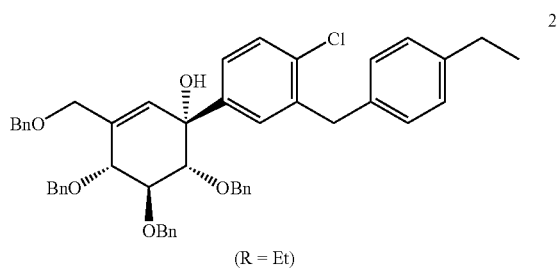

(R = Et)

The above Grignard reagent was added dropwise into the solution of (4R,5S,6R)-4,5,6-tris(benzyloxy)-3-(benzyloxymethyl)cyclohex-2-enone 1 (2 g, 3.74 mmol, 1 eq) in dry THF (20 mL) under argon at room temperature (about 25° C.), then allowed to react for over 3 hours. $NH_4Cl$ (aq. sat) was added into the mixture to quench the reaction. The mixture was extracted with ethyl acetate (20 mL×3), the organic layer was washed with brine, dried over $Na_2SO_4$, filtrated, the filtrate was evaporated to dryness. The residue was purified on silica gel chromatography (eluent, petroleum ether:ethyl acetate=20:1) to give a yellow oil of the target compound 2 (2.428 g, 3.17 mmol, yield of 84.8%). $^1H$-NMR (400 MHz, $CDCl_3$): δ 7.42 (1H, s), 7.28-7.41 (17H, m), 7.04-7.254 (8H, m), 5.83 (1H, s), 4.74 (1H, d, J=11.2 Hz), 4.39-4.64 (7H, m), 4.33 (1H, d, J=12.4 Hz), 4.23 (1H, s), 4.08 (2H, s), 4.03 (1H, d, J=12.8 Hz), 3.70-3.73 (2H, m), 2.93 (1H, s), 2.58 (2H, q, J=7.6 Hz), 1.19 (3H, t, J=7.6 Hz); MS (ESI$^+$): 765 [M+H]$^+$, 782 [M+$H_2O$]$^+$, 787 [M+Na]$^+$.

(3) The Preparation of 3 (R=Et)

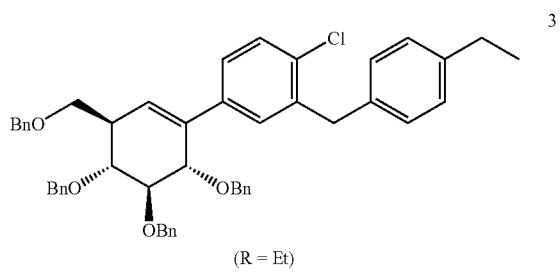

(R = Et)

Triethylsilane (1 mL, 7.44 mmol, 3 eq) and boron-trifluoride etherate (0.44 mL, 4.96 mmol, 2 eq) were added in that order into a solution of 2 (1.9 g, 2.48 mmol, 1 eq) in $CH_2Cl_2$ under argon at −20° C., then allowed to react for over 4 hours maintaining a temperature of −20° C. NaCl (aq. sat) was added to the quench the reaction. The mixture was extracted with $CH_2Cl_2$ (20 mL×3), and the organic layer was washed with brine, dried over $Na_2SO_4$, filtrated, the filtrate was evaporated to dryness. The residue was purified on silica gel chromatography (eluent, petroleum ether:ethyl acetate=20:1) to give a yellow oil of target compound (1.67 g, 2.23 mmol, 89.9%). $^1$H-NMR (400 MHz, $CDCl_3$): δ 7.26-7.40 (16H, m), 7.15-7.25 (7H, m), 7.04-7.06 (4H, m), 6.85-6.87 (2H, m), 5.89 (1H, s), 4.85-4.98 (3H, m), 4.75-4.77 (1H, m), 4.45-4.56 (4H, m), 4.32 (1H, d, J=10.8 Hz), 3.97-4.09 (4H, m), 3.74 (1H, t, J=10.4 Hz), 3.62-3.65(1H, m), 3.54-3.57 (1H, m), 2.63-2.71 (1H, m), 2.59 (2H, q, J=7.6 Hz), 1.21 (3H, t, J=7.6 Hz); MS ($ESI^+$) 749 $[M+H]^+$, 766 $[M+H_2O]^+$.

(4) The preparation of 4 (R=Et)

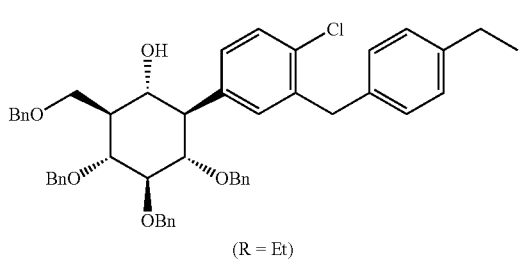

(R = Et)

Borane-dimethyl sulfide complex (2M in THF) (1.678 mL, 3.34 mmol, 10 eq) was added into the solution of 3 (250 mg, 0.334 mmol, 1 eq) in dry THF (10 mL) under argon at 0° C., then warmed to reflux for 1 h. The mixture was treated with NaOH (3M in $H_2O$, 1 mL, 3.34 mmol, 10 eq) at 0° C., then 30% $H_2O_2$ (0.11 mL, 3.34 mmol, 10 eq) at room temperature (above 30° C.), and allowed to react overnight at room temperature (~25° C.). $NH_4Cl$ (aq. sat) was added into the mixture to quench the reaction. The mixture was extracted with ethyl acetate (10 mL×3), the organic layer was washed with brine, dried over $Na_2SO_4$, filtered, and the filtrate was evaporated to dryness. The residue was purified by preparative TLC to give a white solid of target compound 4 (108.8 mg, 0.142 mmol, 42.5%). $^1$H-NMR (400 MHz, $CDCl_3$) δ 7.29-7.40 (15H, m), 7.12-7.24 (7H, m), 7.03-7.07 (4H, m), 6.74 (2H, d, J=6.8 Hz), 4.94 (1H, d, J=10.8 Hz), 4.91 (2H, s), 4.46-4.58 (4H, m), 4.01-4.13 (2H, m), 3.83-3.93 (3H, m), 3.68-3.73 (2H, m), 3.52-3.62 (2H, m), 2.74 (1H, t, J=10.8 Hz), 2.59 (2H, q, J=7.6 Hz), 1.89-1.96 (1H, m), 1.19 (3H, t, J=7.6 Hz); MS ($ESI^+$) 767 $[M+H]^+$, 784 $[M+H_2O]^+$, 789 $[M+Na]^+$.

(5) The Preparation of 5 (R=Et)

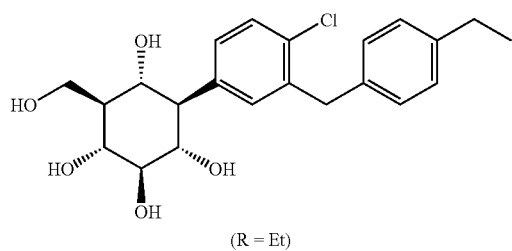

(R = Et)

The solution of 4 (12 mg, 1.57×10$^{-2}$ mmol, 1 eq) in THF:$CH_3OH$=2:1 (9 mL) was treated with 1,2-dichlorobenzene (1 mol) and Pd/C (10% quality containing, 12 mg, 100% quality ratio) and stirred over 2 h under a $H_2$ atmosphere at room temperature (above 30° C.). The reaction was monitored by LC-MS to confirm completion. The mixture was filtered, and the filtrate was evaporated to dryness. The residue was purified by preparative HPLC to give target compound 5 (2.82 mg, 0.69×10$^{-2}$ mmol, yield of 43.9%) as a white solid. $^1$H-NMR (400 MHz, $CD_3OD$) δ 7.33 (1H, d, J=8.0 Hz), 7.07-7.17 (6H, m), 4.05 (2H, s), 3.91 (2H, d, J=3.2 Hz), 3.65 (1H, t, J=10.4 Hz), 3.39-3.49 (2H, m), 3.31 (1H, t, J=8.8 Hz), 2.51-2.62 (3H, m), 2.53 (1H, m), 1.19 (3H, t, J=8.0 Hz); MS ($ESI^+$): 407 $[M+H]^+$, 424 $[M+NH_4]^+$, 448 $[M+H+CH_3CN]^+$, 813 $[2M+H]^+$, ($ESI^-$): 405 $[M-H]^-$, 451 $[M+HCOO]^-$.

The following process was adapted from the procedure disclosed in US 2006/0063722 A1.

(6) The Preparation of (5-bromo-2-chlorophenyl)(4-ethylphenyl)methanone 7

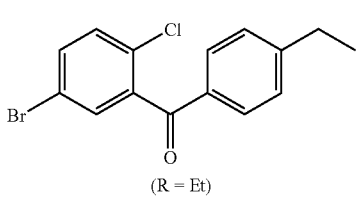

(R = Et)

To a 2 L round bottom flask containing a magnetic stirred suspension of commercial 5-bromo-2-chlorobenzoic acid (410 g, 1.74 mol) in 700 mL of $CH_2Cl_2$ was added oxalyl chloride (235 g, 1.85 mol) followed by 1.5 mL of DMF. To trap the resultant HCl, the flask was fitted with tubing so that the gas was discharged above the surface of a stirred aq KOH solution. When the vigorous evolution of gas ceased after two hours, the homogeneous reaction was stirred overnight prior to removal of the volatiles under vacuum using a rotary evaporator. The resultant oil solidified during subsequent evacuation. After dissolving the crude 5-bromo-2-chlorobenzoyl chloride in 530 mL of the ethylbenzene, the yellow solution was cooled to −3° C., prior to adding $AlCl_3$ (257 g, 1.93 mol) in ~30 g portions over 60 min to insure that the temperature did not exceed 10° C. The copious amounts of HCl gas which began to evolve after 60% of the $AlCl_3$ had been added were trapped by passing the gas over a stirred conc. NaOH solution. If the reaction were more concentrated, a magnetic stirred could not have maintained stirring upon completion of the addition of $AlCl_3$. After stirring for 1 h as the bath warmed to ~15° C., the bath was removed. After 4 h at 20° C., the thick syrup was poured over ice (1.5 kg). Subsequently, once the stirred suspension had cooled, $H_2O$ (1 L) was added prior to being extracted four times with 1N HCl, three times with 1M KOH, and twice with brine prior to drying over $Na_2SO_4$. The volatiles were removed using first a rotary evaporator and then by heating at 60° C. at 1 Torr. $^1$H-NMR analysis of the resultant dark oil revealed the residue to be a 1:14 mixture of ortho/para isomers. Dissolution in hexane and followed by filtration through a silica gel pad removed most of the color. Concentration of the eluent yielded 560 g (99% of the 14:1 mixture of the (5-bromo-2-chlorophenyl)(4-ethylphenyl)methanone/(5-bromo-2-chlorophenyl)(2-ethylphenyl)methanone).

(7) The Preparation of 4-bromo-1-chloro-2-(4-ethylbenzyl)benzene 8

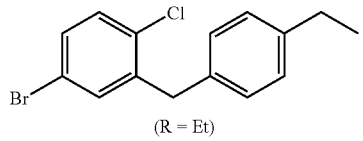

(R = Et)

To a stirred solution of Et$_3$SiH (400 g, 3.45 mol) and (5-bromo-2-chlorophenyl)(4-ethylphenyl)methanone (534 g, 1.65 mol) containing ~7% of the isomeric ketone in 300 mL of the TFA at 30° C. was added CF$_3$SO$_3$H (1.5 g, 0.01 mol). Within minutes the temperature increased causing the solution to reflux violently. Caution: this moderate exotherm requires cooling with an external ice bath. After 1 hr, HPLC revealed the reaction to be 90% complete. After addition of an additional Et$_3$SiH (20 g) and heating overnight at 70° C., the reaction was >95% complete by HPLC analysis. Upon cooling, the volatiles were removed by bulb to bulb distillation at reduced pressure. The resultant ~1 L of the light gray oil was poured into 1 L of H$_2$O. The mixture was extracted three times with hexane, the combined organic layers were washed three times with H$_2$O, twice with aq Na$_2$CO$_3$ and twice with brine before drying over Na$_2$SO$_4$. After concentration using a rotary evaporator, ~1 L of clear light amber oil remained. This material was further concentrated, the (Et$_3$Si)$_2$O (450 mL) was removed by distillation until the distillation head temperature reached 75° C., and the residue was allowed to cool. $^1$HNMR analysis of the residue revealed it to contain an ~8:1 mixture of diarylmethane to (Et$_3$Si)$_2$O. Crystallization of this mixture was achieved by pouring the product into vigorously stirred cold (10° C.) mixture of 85% EtOH:H$_2$O (1.2 L). After stirring for several hours, the crystals were collected by filtration, washed with cold 1:1 EtOH/H$_2$O and dried under vacuum. The 4-bromo-1-chloro-2-(4-ethylbenzyl)benzene (500 g), was obtained as a low melting solid containing ~1% (Et$_3$Si)$_2$O, and was used without further purification.

Example 2

This Example Illustrates the Preparation of (1R,2R,3S,4R,5R,6S)-4-(4-chloro-3-(4-ethoxybenzyl)phenyl)-6-(hydroxymethyl)cyclohexane-1,2,3,5-tetraol (9)

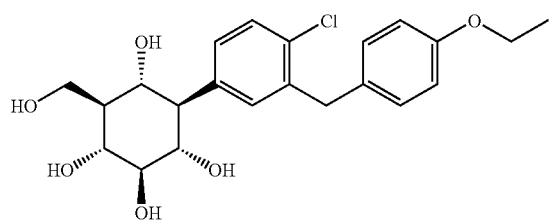

Compound 9 was prepared by a method analogous to that described in Example 1: H$^1$-NMR (400 MHz, CD$_3$OD): δ 7.32 (1H, d, J=8.0), 7.11-7.16 (4H, m), 6.79 (2H, d, J=6.8 Hz), 3.96-4.02 (4H, m), 3.91 (1H, d, J=3.2 Hz), 3.63 (1H, t, J=10.4 Hz), 3.39-3.47 (2H, m), 3.32 (1H, t, J=8.8 Hz), 2.54 (1H, t, J=10.4 Hz), 1.53 (1H, tt, J=3.2, 10.4 Hz), 1.36 (3H, t, J=7.2 Hz); MS (ESI$^+$): 423 [M+H]$^+$, 440 [M+NH$_4$]$^+$, 845 [2M+H]$^+$, 862 [2M+NH$_4$]$^+$, (ESI$^-$): 467 [M+HCOO]$^-$.

Example 3

This Example Illustrates the Preparation of (1R,2R,3S,4R,5R,6S)-4-(4-chloro-3-(4-cyclopropylbenzyl)phenyl)-6-(hydroxymethyl)cyclohexane-1,2,3,5-tetraol (10)

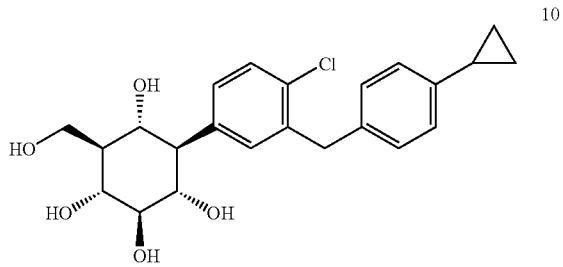

Compound 10 was prepared by a method analogous to that described in Example 1: $^1$H NMR (400 MHz, CDCl$_3$): δ 7.33 (1H, d, J=8.0 Hz), 7.16-7.12 (2H, m), 7.09 (2H, d, J=8.0 Hz), 6.96 (2H, d, J=8.0 Hz), 4.04 (2H, s), 3.91 (2H, d, J=3.2 Hz), 3.65 (1H, t, J=10.6 Hz), 3.48 (1H, t, J=10.0 Hz), 3.42 (1H, t, J=10.0 Hz), 3.32 (1H, t, J=9.0 Hz), 2.54 (1H, t, J=10.8 Hz), 1.87-1.82 (1H, m), 1.57-1.51 (1H, m,), 0.94-0.89 (2H, m), 0.64-0.60 (2H, m); MS (ESI$^+$): 419 [M+H]$^+$, 436 [M+NH$_4$]$^+$.

Example 4

This Example Illustrates the Preparation of (1R,2R,3S,4R,5R,6S)-4-(4-chloro-3-(4-propylbenzyl)phenyl)-6-(hydroxymethyl)cyclohexane-1,2,3,5-tetraol (11)

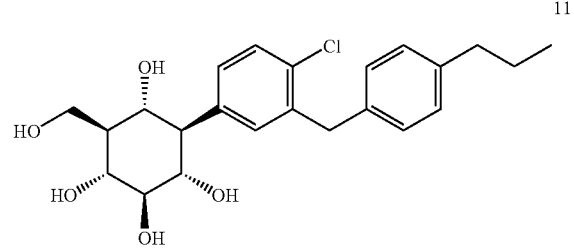

Compound 11 was prepared by a method analogous to that described in Example 1: $^1$H NMR (400 MHz, CDCl$_3$): δ 7.35 (1H, d, J=8.4 Hz), 7.20 (1H, d, J=1.6 Hz), 7.16-7.13 (3H, m), 7.08 (2H, d, J=8.0 Hz), 4.07 (2H, s), 3.93 (2H, d, J=3.2 Hz), 3.67 (1H, t, J=10.4 Hz), 3.49 (1H, t, J=10.4 Hz), 3.43 (1H, t, J=10.4 Hz), 3.33 (1H, t, J=9.0 Hz), 2.58-2.53 (3H, m), 1.67-1.58 (2H, m), 1.58-1.52 (1H, m), 0.94 (3H, t, J=7.2 Hz); MS (ESI$^+$): 438 [M+NH$_4$]$^+$.

Example 5

This Example Illustrates the Preparation of (1R,2R, 3S,4R,5R,6S)-4-(4-chloro-3-(4-cyclohexylbenzyl) phenyl)-6-(hydroxymethyl)cyclohexane-1,2,3,5-tetraol (12)

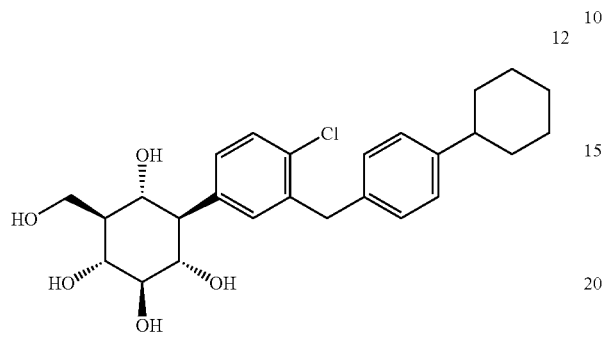

Compound 12 was prepared by a method analogous to that described in Example 1: $^1$H NMR (400 MHz, CDCl$_3$): δ 7.34 (1H, d, J=8.0 Hz), 7.19 (1H, d, J=2.0 Hz), 7.15-7.12 (3H, m), 7.09 (2H, d, J=8.4 Hz), 4.05 (2H, s), 3.92 (2H, d, J=3.2 Hz), 3.66 (1H, t, J=10.6 Hz), 3.48 (1H, t, J=10.0 Hz), 3.43 (1H, t, J=10.2 Hz), 3.32 (1H, t, J=9.0 Hz), 2.55 (1H, t, J=10.6 Hz), 2.48-2.42 (1H, m), 1.84-1.81 (4H, m), 1.76-1.73 (1H, m), 1.57-1.50 (1H, m), 1.47-1.36 (4H, m), 1.34-1.22 (1H, m); MS (ESI$^+$): 478 [M+NH$_4$]$^+$.

Example 6

This Example Illustrates the Preparation of (1R,2S, 3S,6R)-4-(4-chloro-3-(4-(3-cyclopropylprop-2-yny-loxy)benzyl)phenyl)-6-(hydroxymethyl)cyclohex-4-ene-1,2,3-triol (13)

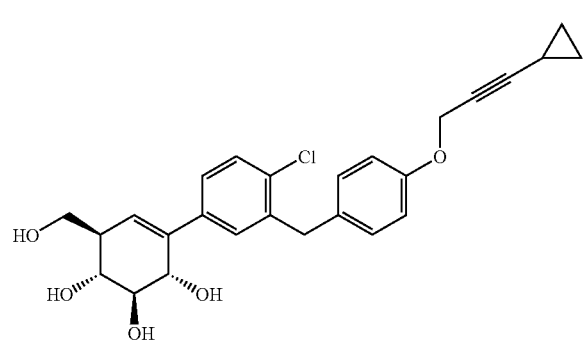

$^1$H-NMR (400 MHz, CD$_3$OD): δ 7.27-7.31 (2H, m), 7.20-7.23 (1H, m), 7.09 (2H, d, J=8.8 Hz), 6.82-6.84 (2H, m), 5.83-5.84 (1H, m), 4.02 (2H, dd, J=14.8 Hz), 3.83-3.86 (1H, m), 3.48-3.65 (3H, m), 2.36 (1H, b), 0.72-0.77 (2H, m), 0.57-0.60 (2H, m); MS (ESI$^+$): 472 [M+NH$_4$]$^+$, 479 [M+Na]$^+$, (ESI$^-$): 499 [M+HCOO]$^-$.

Example 7

Figure 4:
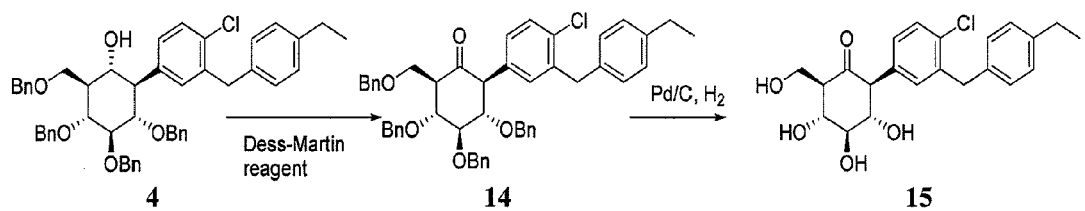

This Example Illustrates the Preparation of (2S,3S, 4R,5R,6R)-2-(4-chloro-3-(4-ethylbenzyl)phenyl)-3, 4,5-trihydroxy-6-(hydroxymethyl)cyclohexanone (15) using the Synthetic Approach Outlined in FIG. 4

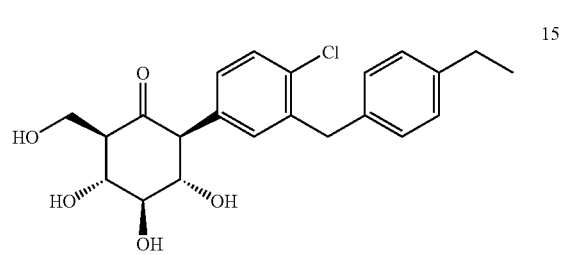

Dess-Martin reagent (MW 424.5, white powder, 1.5 eq) was added to a solution of (1R,2S,3R,4R,5S,6R)-3,4,5-tris (benzyloxy)-2-(benzyloxymethyl)-6-(4-chloro-3-(4-ethyl-benzyl)phenyl)cyclohexanol (4, R=Et) (1.0 g, 1.3 mmol) in anhydrous CH$_2$Cl$_2$ (20 mL) at 0° C., then the mixture was stirred overnight at room temperature. The reaction mixture was quenched with 1N NaOH, separated, and the aqueous layer was extracted with CH$_2$Cl$_2$. The organic layers were combined, dried over Na$_2$SO$_4$, and filtered. The filtrate was evaporated to dryness, and the residue was purified by preparative TLC to give compound 14 (0.92 g, white solid, purity of 95%, yield of 92.3%). $^1$H-NMR (400 MHz, CDCl$_3$): δ 7.29-7.37 (14H, m), 7.13-7.23 (5H, m), 7.03-7.08 (4H, dd, J=8.4 Hz), 6.97-6.99 (2H, m), 6.76 (2H, d, J=7.6 Hz), 4.91-4.95 (3H, m), 4.64 (1H, d, J=10.8 Hz), 4.50-4.57 (3H, m), 3.91-4.14 (6H, m), 3.74-3.76 (3H, m), 2.80 (1H, d, J=8.4 Hz), 2.58 (2H, dd, J=7.6 Hz), 1.20 (3H, t, J=7.6); MS (ESI$^+$): 765 [M+H]$^+$, 782 [M+H$_2$O]$^+$, 787 [M+Na]$^+$.

The solution of 14 (0.92 g, purity of 95%, 1.20 mmol, 1 eq) in THF:CH$_3$OH (2:1) (12 mL) was treated with 1,2-dichlo-robenzene (0.354 g, 0.3 mL, 2.41 mmol, 2 eq) and Pd/C (10%, 74 mg, 8 weight %) and stirred over 4 h under H$_2$ atmosphere at room temperature (about 25° C.). The reaction was monitored by LC-MS until completion. The mixture was filtered, and the filtrate was evaporated to dryness. The residue (yellow oil) was purified by preparative HPLC to obtain compound 15 (450 mg, white solid, purity of 98%, yield of 92.6%). $^1$H-NMR (400 HMz, CD$_3$OD): δ 7.34 (1H, d, J=8.0 Hz), 6.99-7.12 (6H, m), 4.05 (2H, s), 3.98 (1H, dd, J=2.8, 10.8 Hz), 3.88 (1H, dd, J=5.6, 11 Hz), 3.77-3.81 (2H, m), 3.57-3.67 (2H, m), 2.65-2.79 (1H, m), 2.59 (2H, d, J=7.6, 15.2 Hz), 1.20 (3H, t, J=7.6 Hz); MS (ESI$^+$): 405 [M+H]$^+$, 422 [M+NH$_4$]$^+$, (ESI$^-$): 403 [M-H]$^-$, 449 [M+HCOO]$^-$.

Example 8

Preparation of (1R,2R,3S,4S,5R,6R)-4-(4-chloro-3-(4-ethylbenzyl)phenyl)-6-(hydroxymethyl)-5-methoxycyclohexane-1,2,3-triol (16)

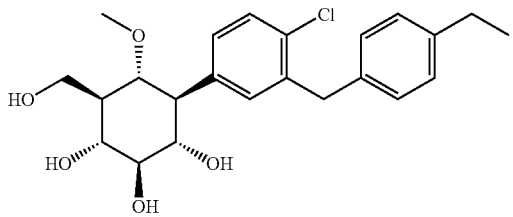

(1) The Preparation of 4-((1R,2S,3R,4R,5S,6R)-2,3,4-tris(benzyloxy)-5-(benzyloxy methyl)-6-methoxy-cyclohexyl)-2-(4-ethylbenzyl)-1-chlorobenzene NaH (157 g, 1.5 eq, 60% containing in oil) was added into the solution of (1R,2S,3R,4R,5S,6R)-3,4,5-tris(benzyloxy)-2-(benzyloxymethyl)-6-(4-chloro-3-(4-ethylbenzyl)phenyl)cyclohexanol (4, R=Et, 2 g, 2.61 mmol) in anhydrous THF (10 mL) at 0° C. TBAI (0.1 eq) and CH₃I (760 mg, 2 eq) were added into the reaction mixture after stirring for 1 h at the same temperature and the reaction mixture was stirred overnight at rt. Sat aq. NH₄Cl was added to quench the reaction and the resulting mixture was extracted with EtOAc. The combined organic layers were dried over Na₂SO₄, filtered, and the filtrate was evaporated to dryness. The residue (yellow oil, 2.05 g) was dissolved in THF:CH₃OH=2:1, treated with 1,2-dichlorobenzene (1% mol ratio) and Pd/C (10%, 1/1 weight ratio), and stirred over 2 h under H₂ atmosphere at room temperature. The reaction was monitored by LC-MS until completion. The mixture was filtered, and the filtrate was evaporated to dryness and purified by preparative HPLC to give target compound 16 (987 mg, (white solid, yield of 90.0%). $^1$H-NMR (400 MHz, CD₃COCD₃): δ 7.32-7.34 (2H, m), 7.22 (1H, dd, J=2.4, 8.0 Hz), 7.12 (4H, dd, J=8.4 Hz), 4.15 (2H, s), 3.93-3.98 (1H, m), 3.70-.3.75 (1H,m), 3.65-3.67 (1H, m), 3.54-3.60 (2H, m), 3.37 (1H, t, J=10.4 Hz), 3.30 (1H, t, J=8.8 Hz), 2.84 (3H, s), 2.52-2.65 (3H, m), 1.51-1.58 (1H, m), 1.17 (3H, t, J=7.2 Hz); MS (ESI⁺): 421 [M+H]⁺, 438 [M+NH₄]⁺, 841 [2M+H]⁺, 858 [2M+NH₄]⁺, (ESI⁺): 465 [M+HCOO]⁻.

Example 9

Preparation of ((1S,2R,3R,4S,5R,6R)-3-(4-chloro-3-(4-ethylbenzyl)phenyl)-2,4,5,6-tetrahydroxycyclohexyl)methyl acetate (17)

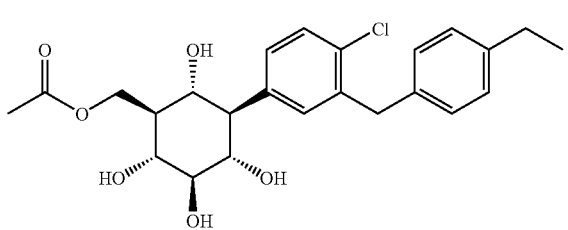

Ac₂O (377 mg, 1.5 eq) was added dropwised into the solution of (1R,2R,3S,4R,5R,6S)-4-(4-chloro-3-(4-ethylbenzyl)phenyl)-6-(hydroxymethyl)cyclohexane-1,2,3,5-tetraol (5, R=Et, 1 g, 2.46 mmol) and DMAP (cat.) in CH₂Cl₂ (10 mL) at 0° C. followed by pyridine (292 mg, 1.5 eq), and the mixture was stirred overnight at rt. The reaction mixture was washed with 3N HCl, and the organic layer was combined, dried over Na₂SO₄, filtered, and the filtrate was evaporated to dryness. The residue was purified by preperative HPLC to give target compound (566 mg, white solid, yield of 50.4%). $^1$H-NMR (400 MHz, CD₃OD): δ 7.32 (1H, d, J=8.4 Hz), 7.06-7.14 (6H, m), 4.37 (2H, ddd, J=2.0, 10.8, 16.8 Hz), 4.04 (2H, s), 3.57 (1H, t, J=10.8 Hz), 3.40-3.47 (1H, m), 2.49-2.60 (3H, m), 2.04 (3H, s), 1.60-1.66 (1H, m), 1.18 (3H, t, J=8.0 Hz); MS (ESI⁺): 449 [M+H]⁺, 466 [M+NH₄]⁺, 897 [2M+H]⁺, (ESI⁻): 492 [M+HCOO]⁻, 941 [2M+HCOO]⁻.

Example 10

Preparation of (4aR,5R,6R,7S,8S,8aR)-8-(4-chloro-3-(4-ethylbenzyl)phenyl)-2,2-dimethylhexahydro-4H-benzo[d][1,3]dioxine-5,6,7-triol (18)

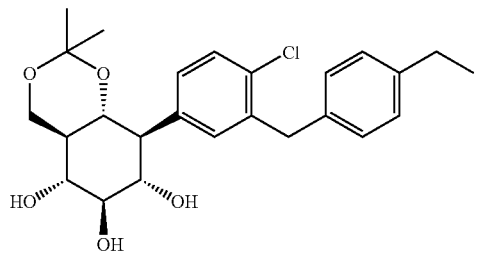

1N HCl (5 mL) was added dropwised into the solution of (1R,2R,3S,4R,5R,6S)-4-(4-chloro-3-(4-ethylbenzyl)phenyl)-6-(hydroxymethyl)cyclohexane-1,2,3,5-tetraol (5, R=Et, 1 g, 2.46 mmol) in MeOH (80 mL) and acetone (20 mL), and stirred overnight, then the mixture was evaporated to dryness. The residue was purified by preparative HPLC to give the target compound (864 mg, white solid, yield of 75.3%). $^1$H-NMR (400 MHz, CD₃COCD₃): δ 7.26-7.29 (2H, m), 7.10-7.16 (5H, m), 3.74-4.21 (6H, m), 3.46-3.51 (1H, m), 3.35-3.37 (1H, m), 2.56-2.66 (3H, m), 1.72-1.75 (1H, m), 1.28 (3H, s), 1.18 (3H, t, J=7.6 Hz), 1.13 (3H, s); MS (ESI⁺): 447 [M+H]⁺, 488 [M+H+CH₃CN]⁺, 910 [2M+NH₄]⁺, 491 [M+HCOO]⁻, 937 [2M+HCOO]⁻.

Example 11

Preparation of (1S,2R,3R,4S,5R,6R)-4-(acetoxymethyl)-6-(4-chloro-3-(4-ethylbenzyl)phenyl)cyclohexane-1,2,3,5-tetrayl tetraacetate (19)

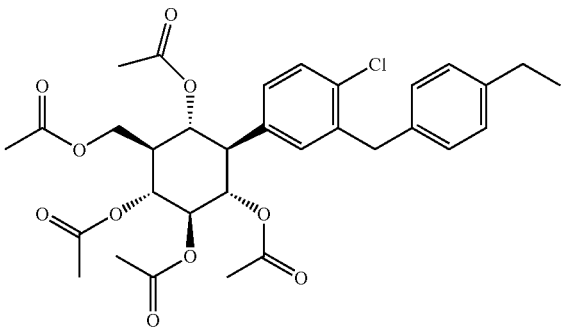

Compound 19 was prepared from compound 5 (R=Et) as described in Example 20. ¹H-NMR (400 MHz, CDCl₃): δ 7.29 (1H, d, J=8.4 Hz), 7.30-7.12 (6H, m), 5.27-5.38 (3H, m), 5.20 (1H, t, J=9.6 Hz), 4.03-4.06 (3H, m), 3.93-3.96 (1H, m), 2.98 (1H, t, J=11.6), 2.61 (2H, q, J=7.6 Hz), 2.14-2.20 (1H, m), 2.08 (3H, s), 2.06 (3H, s), 2.00 (3H, s), 1.66 (6H, s), 1.21 (3H, t, J=7.6 Hz); MS (ESI⁺): 617 (M+H)⁺, 934 [M_NH₄]⁺, (ESI⁻): 661 [M+HCOO]⁻.

Example 12

Figure 5:
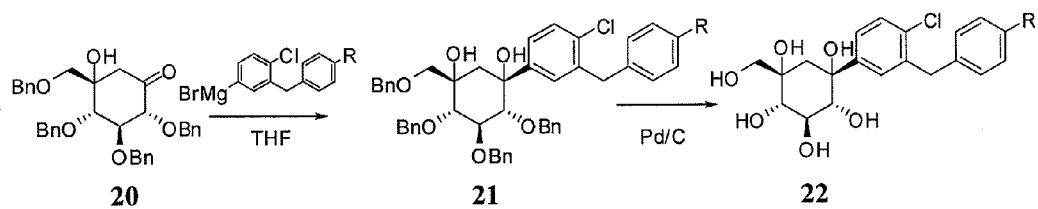

This Example Provides the Preparation of (1R,2R,3R,4S,5S)-1-(4-chloro-3-(4-ethylbenzyl)phenyl)-5-(hydroxymethyl)cyclohexane-1,2,3,4,5-pentaol (22, R=Et) using the Synthetic Methods Outlined in FIG. 5

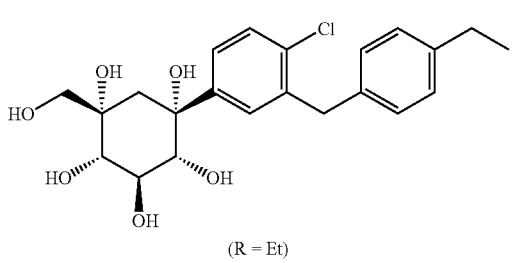

(R = Et)

Compound 22 was prepared by a method analogous to that described in Example 1. ¹H-NMR (400 MHz, CD₃OD): δ 7.45 (1H, s), 7.32-7.33 (2H, m), 7.05-7.10 (4H, m), 4.05 (2H, s), 3.86 (1H, t, J=9.6 Hz), 3.67 (1H, d, J=9.2 Hz), 3.54-3.57 (2H, m), 3.31-3.35 (2H, m), 2.57 (2H, q, J=8.0 Hz), 2.00 (1H, d, J=15.2 Hz), 1.81 (1H, d, J=15.2 Hz), 1.18 (3H, t, J=8.0 Hz).

Example 13

Preparation of (1R,2R,3R,4S,5S)-1-(3-(4-ethylbenzyl)phenyl)-5-(hydroxymethyl)cyclohexane-1,2,3,4,5-pentaol (23)

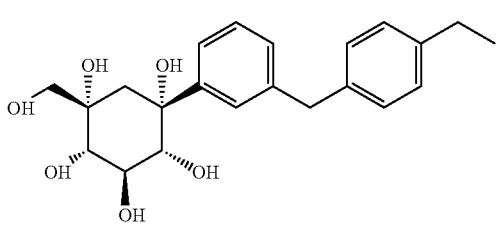

Compound 23 was prepared by a method analogous to that described in Example 12. ¹H-NMR (400 MHz, CD₃OD): δ 7.39 (1H, s), 7.29-7.31 (1H, m), 7.21-7.25 (1H, m), 7.03-7.11 (5H, m), 3.92 (2H, s), 3.88 (1H, t, J=9.2 Hz), 3.72 (1H, d, J=9.6 Hz), 3.56 (1H, d, J=10.4 Hz), 3.32-3.35 (1H, m), 2.58 (2H, q, J=7.6 Hz), 2.02 (1H, d, J=15.2 Hz), 1.82 (1H, d, J=15.2 Hz), 1.18 (3H, t, J=7.6 Hz).

Example 14

Figure 6:
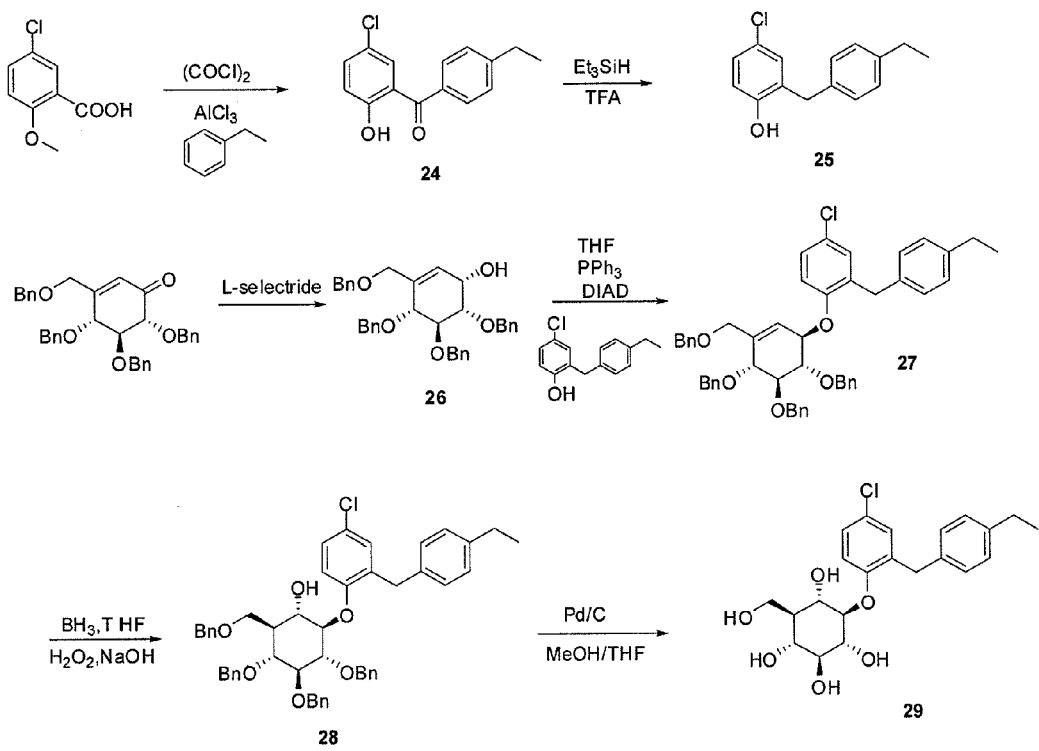

This Example Illustrates the Preparation of (1R,2S,3R,4R,5S,6R)-4-(4-chloro-2-(4-ethylbenzyl)phenoxy)-6-(hydroxymethyl)cyclohexane-1,2,3,5-tetraol (29) as Outlined in FIG. 6

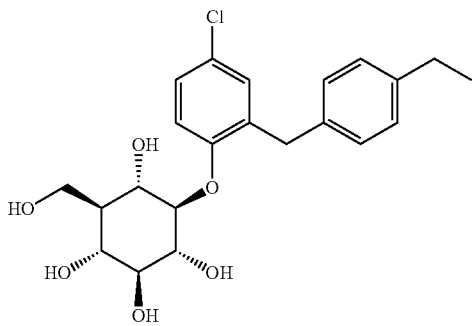

(5-chloro-2-hydroxyphenyl)(4-ethylphenyl)methanone

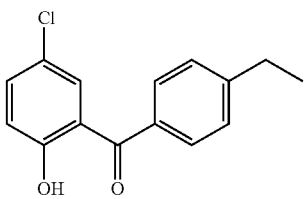

A solution of 2-methoxy-5-chlorobenzoic acid (2.0 g, 10.5 mmol) in dry CH₂Cl₂ (10 mL) was stirred at room temperature under agron. Oxalyl chloride (2.0 g, 15.8 mmol) was added dropwise to the reaction mixture followed by DMF (0.04 mL). After stirring overnight, the volatiles were evaporated using a rotary evaporator and the residue was dissolved in dry CH₂Cl₂ (10 mL) at room temperature under agron. After cooling to −5° C., ethylbenzene (2.57 mL, 21 mmol) was added, followed by portionwise addition of AlCl₃ (2.80 g, 21 mmol) while maintaining the reaction temperature between −5° C. and 0° C. The reaction mixture was stirred for 4 h at room temperature, and then poured into ice water and extracted with CH₂Cl₂ (50 mL×2). The organic layer was then washed with 1N HCl (50 mL), 1N NaOH (50 mL), water (50 mL) and brine (50 mL) and dried over anhydrous Na₂SO₄. The filtrate was concentrated and the crude product was purified by column chromatography (PE:EA=10:1) to give the target compound (1.944 g).

4-chloro-2-(4-ethylbenzyl)phenol

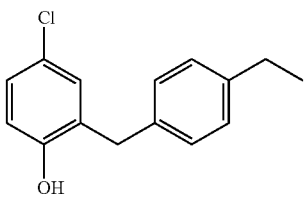

To a stirred 0° C. solution of Et₃SiH (2.26 ml, 14.2 mmol) and (5-chloro-2-hydroxyphenyl)(4-ethylphenyl)methanone (1.944 g, 7.08 mmol) in 10 mL of TFA was added CF₃SO₃H (30 μL) at a rate to keep the temperature at about 0° C. After complete addition, the mixture was warmed to room temperature and stirred overnight at room temperature. After the volatiles were evaporated under reduced pressure, the residue was partitioned in ethyl acetate and water. The organic layer was separated and washed with water, aq $Na_2CO_3$, brine then dried over $Na_2SO_4$ and concentrated. The crude product was purified by column chromatography (PE:EA=10:1) to give the target compound (1.659 g).

((1S,2S,3R,6R)-4-(benzyloxymethyl)-6-(4-chloro-2-(4-ethylbenzyl)phenoxy)cyclohex-4-ene-1,2,3-triyl)tris(oxy)tris(methylene)tribenzene (27)

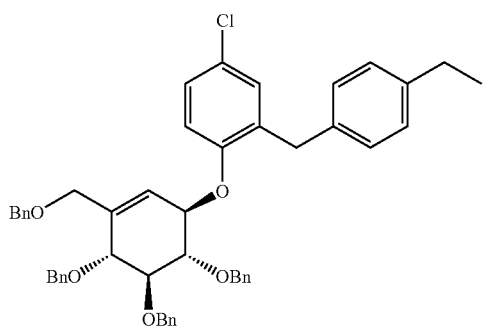

27

In a argon stream, (1S,4R,5S,6S)-4,5,6-tris(benzyloxy)-3-(benzyloxymethyl)cyclohex-2-enol (0.5 g, 0.933 mmol) and triphenylphosphine (367 mg, 1.400 mmol) were added to a THF (6 mL) solution of 4-chloro-2-(4-ethylbenzyl)phenol (345 mg, 1.400 mmol) at room temperature. DIAD (0.276 mL, 1.400 mmol) was added thereto at the same temperature. The reaction mixture was stirred for 48 h. The reaction mixture was concentrated under reduce pressure, and the obtained residue was purified by prepared LC-MS to obtain 157 mg of ((1S,2S,3R,6R)-4-(benzyloxymethyl)-6-(4-chloro-2-(4-ethylbenzyl)phenoxy)cyclohex-4-ene-1,2,3-triyl)tris(oxy)tris(methylene)tribenzene (27).

(1S,2S,3R,4S,5R,6R)-3,4,5-tris(benzyloxy)-2-(benzyloxymethyl)-6-(4-chloro-2-(4-ethylbenzyl)phenoxy)cyclohexanol (28)

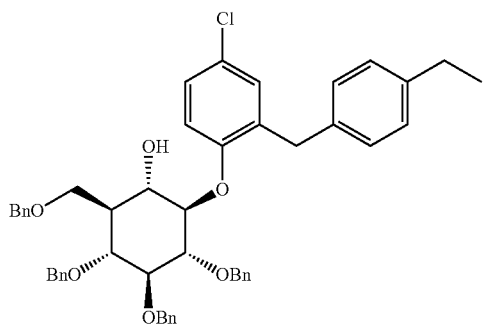

28

To a stirred 0° C. THF solution of ((1S,2S,3R,6R)-4-(benzyloxymethyl)-6-(4-chloro-2-(4-ethylbenzyl)phenoxy)cyclohex-4-ene-1,2,3-triyl)tris(oxy)tris(methylene)tribenzene (27, 150 mg, 0.196 mmol) was added dropwise $BH_3OEt_2$ (2M, 0.98 mL, 1.962 mmol). After stirring for 2 h at 0° C., the mixture was warmed to 25° C. and stirred overnight. $H_2O_2$ (30%, 4.2 mL) was added, followed by added aqueous NaOH solution (1M, 3.93 mL, 3.93 mmol) to the reaction mixture at 0° C. After complete addition, the reaction mixture was warmed to 25° C. and stirred for 3 h. The reaction was quenched by addition of dilute HCl (1N, 10 mL) and extracted with ethyl acetate (3×30 mL). The organic layers were washed with water and brine prior to drying over anhydrous $Na_2SO_4$. The residue was purified by preparative TLC (EA:PE=1:8 v/v) to obtain 59 mg of (1S,2S,3R,4S,5R,6R)-3,4,5-tris(benzyloxy)-2-(benzyloxymethyl)-6-(4-chloro-2-(4-ethylbenzyl)phenoxy)cyclohexanol (28).

(1R,2S,3R,4R,5S,6R)-4-(4-chloro-2-(4-ethylbenzyl)phenoxy)-6-(hydroxymethyl)cyclohexane-1,2,3,5-tetraol (29)

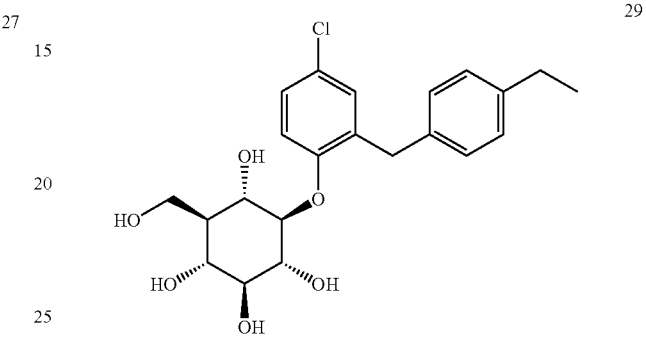

29

14 mL of THF and methanol (1:1) was added to the flask containing the (1S,2S,3R,4S,5R,6R)-3,4,5-tris(benzyloxy)-2-(benzyloxymethyl)-6-(4-chloro-2-(4-ethylbenzyl)phenoxy)cyclohexanol (28, 55 mg, 0.070 mmol). 55 mg of Pd/C (10%) was added in one portion to the reaction mixture. The mixture was degassed five times with $H_2$ and the resulting suspension was stirred under an atmosphere of $H_2$ for 3 h at ambient temperature. The reaction mixture was filtered and concentrated, and the residue was purified by preparative LC-MS to obtain 25 mg of (1R,2S,3R,4R,5S,6R)-4-(4-chloro-2-(4-ethylbenzyl)phenoxy)-6-(hydroxymethyl)cyclohexane-1,2,3,5-tetraol (29). $^1$H-NMR ($D_2O$): δ 7.22~7.2 (1H, d, J=9.2 Hz), 7.17~7.11 (4H, q), 7.08~7.06 (1H, dd), 6.92~6.91 (1H, d, J=3.2 Hz), 4.11~4.08 (1H, t J=9.2 Hz), 4.01 (2H, s), 3.92~3.91 (2H, m), 3.69~3.665 (1H, dd, J=10.8, 8.8 Hz), 3.46~3.39 (2H, m), 3.35~3.30 (1H, m), 2.66~2.58 (2H, q), 1.52~1.46 (1H, tt), 1.24~1.19 (3H, t).

Example 15

Preparation of (1R,2S,3R,4R,5S,6R)-4-(2-(4-ethylbenzyl)phenoxy)-6-(hydroxymethyl)cyclohexane-1,2,3,5-tetraol (30)

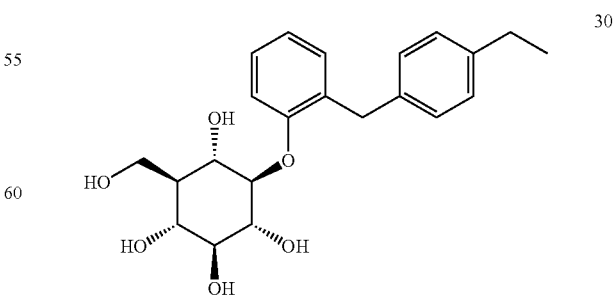

30

Compound 30 was prepared by a method analogous to that described in Example 14. $^1$H-NMR ($D_2O$): δ 7.24~7.22 (1H, d, J=8 Hz), 7.17~7.08 (5H, m), 7.02~6.99 (1H, d, J=7.2 Hz), 6.83~6.79 (1H, t, J=7.2 Hz), 4.14~4.09 (1H, t, J=9.2 Hz), 4.03 (2H, s), 3.94~3.87 (2H, m), 3.68~3.63 (1H, dd, J=10.8, 9.2 Hz), 3.46~3.38 (2H, m), 3.34~3.30 (1H, m), 2.62~2.56 (2H, q), 1.53~1.46 (1H, tt), 1.22~1.18 (3H, t).

Example 16

Preparation of (1R,2S,3R,4R,6R)-4-(3-(4-ethylbenzyl)phenyl)-4-fluoro-6-(hydroxymethyl)cyclohexane-1,2,3-triol (31)

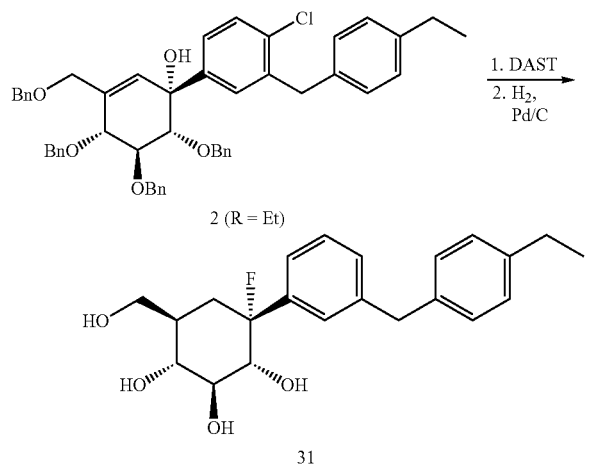

DAST (7 μL) was added into solution of 2 (30 mg) in CH₂Cl₂ (1 mL) at −78° C. under an Ar atmosphere. After 2 h, MeOH (0.5 mL) was added to the mixture, which was then warmed to room temperature. Sat. aq. NaCl (5 mL) was added into the residue, and the mixture was extracted with ethyl acetate (3×10 mL). The combined organic extracts were evaporated, and the residue was dissolved in MeOH/THF (1:1, 5 mL), then treated with Pd/C 10% (10 mg) under a H₂ atmosphere. After 4 h, compound 31 (1.4 mg) was isolated by preparative HPLC. ¹H-NMR (300 MHz): δ 7.18-7.01 (8H, m), 3.90-3.86 (3H, m), 3.77-3.72 (1H, m), 3.61-3.31 (3H, m), 2.62-2.54 (2H, q, J=7.5 Hz), 2.45-2.60 (2H, m), 1.53 (1H, m), 1.20-1.17 (3H, t, J=7.6 Hz); MS (ESI⁺): 375 [M+H]⁺, 392 [M+H₂O]⁺, 416 [M+CH₃CN+H]⁺.

Example 17

Preparation of (1R,2S,3R,6S)-4-(4-chloro-3-(4-ethylbenzyl)phenyl)-6-(fluoromethyl)cyclohex-4-ene-1,2,3-triol (33)

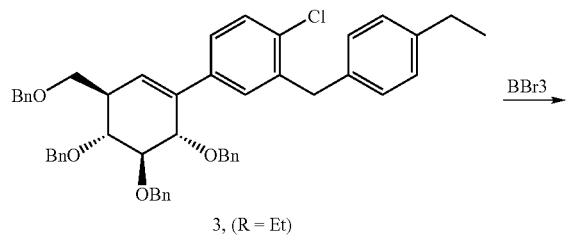

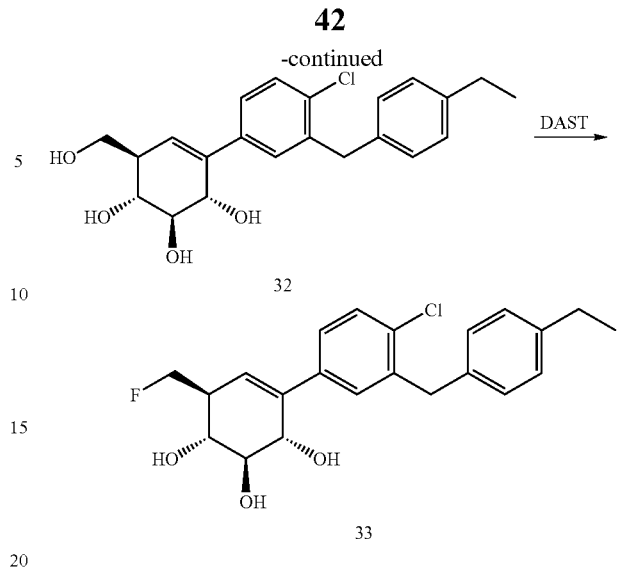

At −78° C., under Ar, BBr₃ (0.33 mL) was added dropwised into solution of 3 (R=Et) (122 mg) in CH₂Cl₂ (5 mL). After stirring for 2 h, sat. aq. NaHCO₃ (1 mL) was added to the mixture, which was then warmed to rt and extracted with ethyl acetate (3×10 mL). The combined organic extracts were dried over Na₂SO₄, concentrated and purified by preparative HPLC, to provide 18 mg of compound 32. ¹H-NMR (400 MHz): δ 7.33-7.30 (2H, m), 7.25-7.23 (1H, m), 7.10 (4H, s), 5.85 (1H, d), 4.58 (2H, s), 4.51-4.49 (1H, m), 4.12-4.01 (2H, q, J=15.2 Hz), 3.89-3.85 (1H, dd, J=4, 10.4 Hz), 3.68-3.53 (3H, m), 2.63-2.57 (2H, q, J=7.6 Hz), 1.23-1.19 (3H, t, J=7.6 Hz); MS (ESI⁺): 406 [M+H₂O]⁺.

The solution of 32 (11 mg) in CH₂Cl₂ (2 mL) was treated with DAST (3 eq, 0.02 mL) at −78° C., under Ar. After 2 h, MeOH (0.5 mL) was added to the mixture, which was then warmed to rt. Sat.aq .NaCl (5 mL) was added to the residue, and the aqueous portion was extracted with ethyl acetate (3×10 mL). The combined organic extracts were evaporated and the residue was purified by preparative HPLC to provide 1.8 mg of compound 33. 1H-NMR (400 MHz) δ 7.30-7.08 (7H, m), 5.85 (1H, m), 4.59-4.57 (1H, m), 4.54 (2H, s), 4.13-4.03 (2H, q, J=15.2 Hz), 3.90-3.86 (1H, dd, J=4, 10.4 Hz), 3.70-3.58 (3H, m), 2.60-2.55 (2H, q, J=7.6 Hz), 1.22-1.18 (3H, t, J=7.6 Hz); MS (ESI⁺): 391 [M+H]⁺; 408 [M+H₂O]⁺.

Example 18

Figure 7:
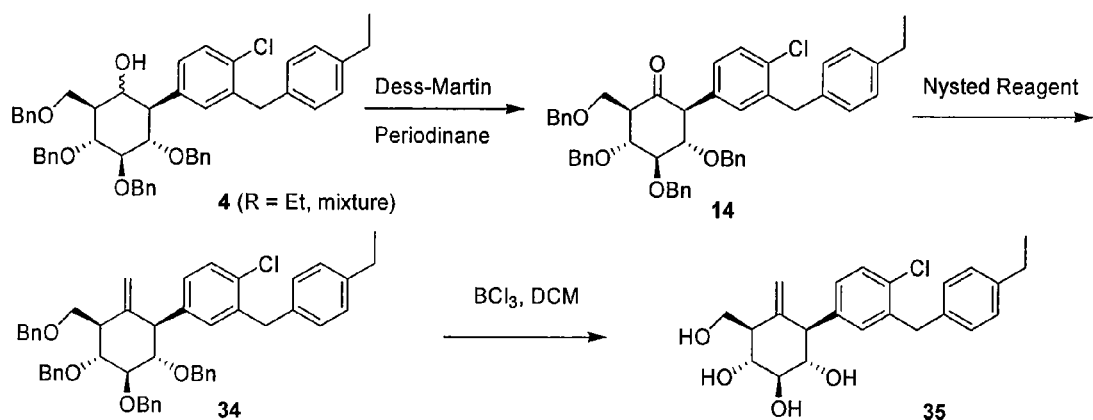

This Example Illustrates the Preparation of (1R,2R,3S,4S,6R)-4-(4-chloro-3-(4-ethylbenzyl)phenyl)-6-(hydroxymethyl)-5-methylenecyclohexane-1,2,3-triol (35), as Outlined in FIG. 7

In Examples 18 and 19, the structures of compounds synthesized were confirmed using the following procedures: ¹H NMR data were acquired on a Varian Mercury 300 spectrometer at 300 MHz, with chemical shifts referenced to internal TMS. Liquid chromatography electrospray ionization mass spectrometry (LC-ESI-MS) analysis was performed on instrumentation consisting of Shimadzu LC-10AD vp series HPLC pumps and dual wavelength UV detector, a Gilson 215 autosampler, a Sedex 75c evaporative light scattering (ELS) detector, and a PE/Sciex API 150EX mass spectrometer. The ELS detector was set to a temperature of 40° C., a gain setting of 7, and a N₂ pressure of 3.3 atm. The Turbo IonSpray source was employed on the API 150 with an ion spray voltage of 5 kV, a temperature of 300° C., and orifice and ring voltages of 5 V and 175 V respectively. Positive ions were scanned in Q1 from 160 to 650 m/z. 5.0 µL injections were performed for each sample, on a Phenomenex Gemini 5 µm C18 column. Mobile phases consisted of 0.05% formic acid in both HPLC grade water (A) and HPLC grade acetonitrile (B) using the following gradients with a flow rate of 2 mL/min: 0.00 min, 95% A, 5% B; 4.00 min, 0% A, 100% B; 5.80 min, 0% A, 100% B; 6.00 min, 95% A, 5% B; 7.00 min, 95% A, 5% B.

Preparation of (2R,3R,4R,5S,6S)-3,4,5-tris(benzyloxy)-2-(benzyloxymethyl)-6-(4-chloro-3-(4-ethylbenzyl)phenyl)cyclohexanone (14)

To a solution of tert-butanol (28.2 µL, 296 µMol) in dichloromethane (4 mL) was added Dess-Martin Periodinane [1,1,1-tris(acetyloxy)-1,1-dihydro-1,2-benziodoxol-3-(1H)-one] (116 mg, 274 µMol), and the resulting mixture was stirred under argon at room temperature for 10 minutes. A solution of alcohol 4 (R=Et, mixture of isomers) in dichloromethane (2 mL) was added to the mixture and stirred at room temperature for 3 hours. The mixture was diluted with 4 mL ethyl acetate and stirred vigorously with aqueous 1.5:1:1 saturated sodium sulfite:saturated sodium bicarbonate:brine (3.5 mL) for a period of 1 hour. The phases were separated and the aqueous phase was re-extracted with ethyl acetate (3 mL). The combined organics were washed with brine (2 mL), dried (anhydrous $Na_2SO_4$), filtered, and evaporated. Preparative TLC using dichloromethane as the developing solvent afforded 91 mg (52%) of compound 14 as a white solid. $^1$H NMR (300 MHz, $CDCl_3$) δ 7.35-6.90 (m, 25H), 6.80 (m, 2H), 4.96 (m, 3H), 4.55 (m, 4H), 4.11 (m, 3H), 3.94 (m, 2H), 3.79 (m, 3H), 3.47 (s, 1H), 2.83 (m, 1H), 2.62 (q, J=7.8 Hz, 2H), 1.16 (t, J=7.5 Hz, 3H). LC-ESI-MS m/z 766 (M+H), 788 (M+Na).

((1S,2R,3R,4R,6S)-4-(benzyloxymethyl)-6-(4-chloro-3-(4-ethylbenzyl)phenyl)-5-methylenecyclohexane-1,2,3-triyl)tris(oxy)tris(methylene)tribenzene (34)

To 0.5 ml anhydrous THF in a vial under a nitrogen blanket was added cyclo-dibromodi-µ-methylene[µ-(tetrahydrofuran)]trizinc [Nysted reagent] (179 mg, 151 µL, 78 µmol, 20% by weight suspension in THF), and the resulting mixture was cooled to −78° C. To this mixture was added (2R,3R,4R,5S,6S)-3,4,5-tris(benzyloxy)-2-(benzyloxymethyl)-6-(4-chloro-3-(4-ethylbenzyl)phenyl)cyclohexanone (14, 40 mg, 52 µmol) in 0.5 mL anhydrous THF followed by $TiCl_4$ (78 µL, 78 µmol, 1 M in DCM) in a drop-wise manner. The mixture was stirred at −78° C. for 20 minutes, and then cooling bath was removed and the mixture was allowed to stir at room temperature for 3 h. Saturated aqueous sodium bicarbonate (2 mL) was added and the resulting mixture was stirred for 30 min. The mixture was extracted into ethyl acetate (2×4 mL), and the organic layer was washed with brine (2 mL), dried over $Na_2SO_4$, filtered, and evaporated. Preparative TLC (8:1 H/EtOAc) afforded 25 mg (63%) of the compound 34. $^1$H NMR (300 MHz, $CDCl_3$) δ 7.34-6.99 (m, 25H), 6.63 (m, 2H), 5.14 (s, 1H), 4.90 (m, 1H), 4.53 (m, 5H), 4.2(m, 3H), 3.78 (m, 3H), 3.60 (m, 2H), 3.47 (s, 1H), 3.35 (m, 1H), 2.56 (q, J=7.8 Hz, 2H), 2.42 (m, 1H), 1.16 (t, J=7.5 Hz, 3H). LC-ESI-MS m/z 764 (M+H), 786 (M+Na).

(1R,2R,3S,4S,6R)-4-(4-chloro-3-(4-ethylbenzyl)phenyl)-6-(hydroxymethyl)-5-methylenecyclohexane-1,2,3-triol (35)

To a solution of ((1S,2R,3R,4R,6S)-4-(benzyloxymethyl)-6-(4-chloro-3-(4-ethylbenzyl)phenyl)-5-methylenecyclohexane-1,2,3-triyl)tris(oxy)tris(methylene)tribenzene (34, 24 mg, 31.4 mmol) in anhydrous DCM (0.8 mL) in a vial at −78° C. under a nitrogen blanket was added $BCl_3$ (1 M in DCM, 0.25 mL) drop-wise over 15 minutes. The resulting mixture was stirred at −78° C. for 30 minutes and gradually warmed to −20° C. The resulting mixture was stirred at −20° C. for another 30 minutes. At this time, LC-MS indicated that the reaction was complete. The solution was cooled to −78° C. and methanol (1 mL) was slowly added. The resulting solution was warmed to room temperature and concentrated under reduced pressure. The residue was dissolved in 0.5 mL of 1:1 DCM:MeOH and loaded on a preparative TLC plate, which was developed in 15:1 (DCM:MeOH) to obtain 9 mg (71%) of compound 35 as a white solid. $^1$H NMR (300 MHz, $CDCl_3$) δ 7.29-6.89 (m, 7H), 4.80 (s, 1H), 4.28 (s, 1H), 3.95 (m, 4H), 3.64 (m, 2H), 3.51(m, 3H), 3.22 (m, 1H), 2.58 (q, J=7.2 Hz, 2H), 2.25 (m, 1H), 1.18 (t, J=7.5 Hz, 3H). LC-ESI-MS m/z 425 (M+Na).

Example 19

Figure 8:
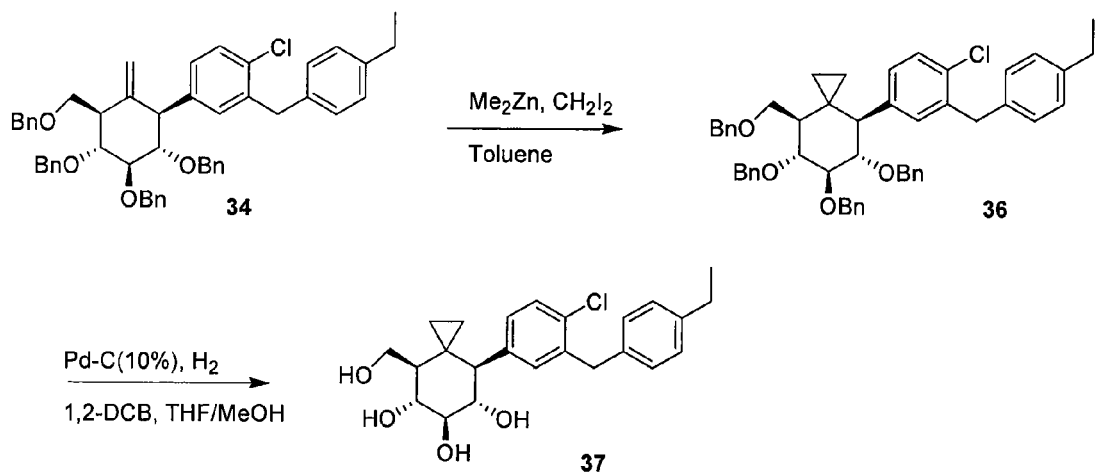

This Example Illustrates the Preparation of (4S,5S,6R,7R,8R)-4-(4-chloro-3-(4-ethylbenzyl)phenyl)-8-(hydroxymethyl)spiro[2.5]octane-5,6,7-triol (37) as Outlined in FIG. 8

(4R,5R,6R,7S,8 S)-5,6,7-tris(benzyloxy)-4-(benzyloxymethyl)-8-(4-chloro-3-(4-ethylbenzyl)phenyl)spiro[2.5]octane (36)

To a vigorously stirred solution of ((1S,2R,3R,4R,6S)-4-(benzyloxymethyl)-6-(4-chloro-3-(4-ethylbenzyl)phenyl)-5-methylenecyclohexane-1,2,3-triyl)tris(oxy)tris(methylene)-tribenzene (34, 25 mg, 32.7 µmol) in anhydrous toluene (2 mL) under nitrogen at −10° C. was added 2M solution of dimethyl zinc (146 µL, 291 µmol) dropwise and stirred for 15 minutes. Diiodomethane (47 µL, 583 µmol) was added drop-wise and the resulting mixture was stirred over night. 40% product formation was observed. More dimethyl zinc (18 more equivalent in two batches over 48 hour period) and diiodomethane (35 equivalent in two batches over 48 hour period) were added and the reaction was 80% complete after 96 hours of reaction. Saturated solution of $NH_4Cl$ (1 mL) was added and the mixture was stirred for 30 minutes. The mixture was diluted with water (1 mL) and extracted into ethyl acetate (3×1 mL). The combined organic extracts were washed with 10% sulfuric acid (1.5 mL), saturated $NaHCO_3$ (1.5 mL) and brine (1.5 mL), dried ($Na_2SO_4$), filtered and evaporated. Preparative TLC (9:1 hexane:ethyl acetate) afforded 85% compound 36 which was used directly in the next reaction.

(4S,5 S,6R,7R,8R)-4-(4-chloro-3-(4-ethylbenzyl)phenyl)-8-(hydroxymethyl)spiro[2.5]octane-5,6,7-triol (37)

To a solution of (4R,5R,6R,7S,8S)-5,6,7-tris(benzyloxy)-4-(benzyloxymethyl)-8-(4-chloro-3-(4-ethylbenzyl)phenyl)spiro[2.5]octane (36, 20 mg, 25.7 µmol) in a mixture of THF (0.2 mL) and methanol (0.8 mL) was added 1,2-dichlorobenzene (58 µL, 515 µmol) followed by 14 mg of palladium on charcoal (10%). The mixture was stirred under 1 atmosphere of hydrogen for 40 minutes. The mixture was filtered through a small pad of Celite in a 6 mL syringe and the Celite pad was washed with methanol (1 mL). Solvent was evaporated under reduced pressure and the residue was purified on preparative TLC plate (8:1 DCM:EtOH) to get 4 mg (37%) of compound 37 as a white solid. $^1$H NMR (300 MHz, $CDCl_3$) δ 7.27-6.85

(m, 7H), 4.01 (s, 2H), 3.80 (m, 2H), 3.63 (m, H), 3.35 (d, J=5.1 Hz, 2H), 3.02 (d, J=11.1 hz, 1H), 2.62 (q, J=7.5 Hz, 2H), 2.06 (m, 1H), 1.21 (t, J=7.5 Hz, 3H), 0.40 (m, 1H), 0.29 (m, 1H), 0.076 (m, 1H), −0.326 (m, 1H). LC-ESI-MS m/z 418 (M+H), 440 (M+Na).

Example 20

This example illustrates the large-scale preparation of compound 5 (R=Et).

Preparation of (1R,2R,3S,4R,5R,6S)-4-(4-chloro-3-(4-ethylbenzyl)phenyl)-6-(hydroxymethyl)cyclohexane-1,2,3,5-tetraol

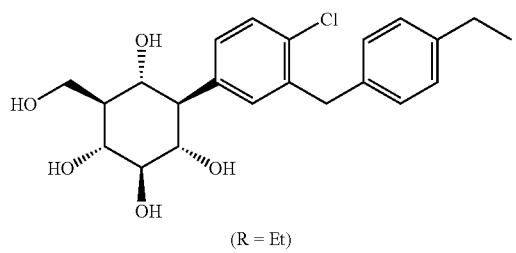

(R = Et)

(1) Preparation of (4R,5S,6R)-4,5,6-tris(benzyloxy)-3-(benzyloxymethyl)cyclohex-2-enone

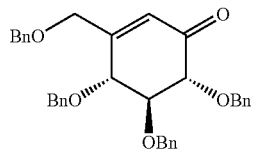

To a solution of (3S,4S,5S,2R)-5-hydroxy-5-[(phenylmethoxy)methyl]-2,3,4-tris(phenyl methoxy)cyclohexan-1-one (580.0 g, 1.051 mol) in anhydrous methylene chloride (3.6 L) was added trifluoroacetic anhydride (331.1 g, 222 mL, 1.577 mol) followed by addition of pyridine (149.7 g, 153 mL, 1.892 mol) at room temperature under argon. The mixture was stirred at room temperature for 24 h and quenched by addition of ice water (1.0 L). The organic layer was separated and the aqueous layer was extracted with methylene chloride (3×2 L). The combined organic layers were washed with sodium bicarbonate (sat. aq. 3×0.5 L), brine (sat. aq. 3×1.0 L), dried over sodium sulfate, filtered and concentrated to give a yellow oil (476.7 g, purity of 90%, yield 85%). $^1$H NMR (CDCl$_3$, 400 MHz): δ 7.26-7.48 (m, 20H), 6.26 (s, 1H), 5.15 (d, J=11.2 Hz, 1H), 5.05 (d, J=10.8 Hz, 1H), 4.95 (d, J=10.8 Hz, 1H), 4.77-4.81 (m, 2H), 4.72 (d, J=11.2 Hz), 4.55 (S, 2H), 4.40-4.42 (m, 1H), 4.31 (d, J=16 Hz, 1H), 4.03-4.13 (m, 3H).

(2) Preparation of (4-chloro-3-(4-ethylbenzyl)phenyl)magnesium bromide

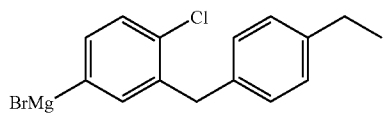

Magnesium powder (34.7 g, 1.446 mol) was charged under argon into a three-necked flask followed by the addition of a portion of a solution of 2-(4-ethylbenzyl)-4-bromo-1-chlorobenzene (122.5 g, 0.398 mol) in anhydrous tetrahydrofuran (0.4 L) and 1,2-dibromoethane (2.89 g, 1.34 mL, 0.015 mol). The mixture was heated to reflux and after reaction initiation (exothermic and consuming magnesium), the rest of the solution of 2-(4-ethylbenzyl)-4-bromo-1-chlorobenzene (245.0 g, 0.796 mol) in anhydrous tetrahydrofuran (0.81 L) was added dropwise. The mixture was then allowed to react for another 1 h under gentle reflux until most of the magnesium was consumed.

(3) Preparation of (1R,4R,5S,6R)-4,5,6-tris(benzyloxy)-3-(benzyloxymethyl)-1-(4-chloro-3-(4-ethylbenzyl)phenyl)cyclohex-2-enol

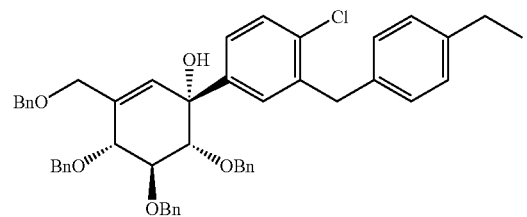

The Grignard reagent from the previous step was added dropwise into a solution of (4R,5S,6R)-4,5,6-tris(benzyloxy)-3-(benzyloxymethyl)cyclohex-2-enone (476.7 g, 90% purity, 0.893 mol) in anhydrous tetrahydrofuran (1.0 L) under argon at room temperature (about 25° C.) and the mixture was stirred for 3 h. Ammonium chloride (aq. sat, 100 mL) was added and the mixture was extracted with ethyl acetate (3×1 L). The organic layer was washed with brine (3×0.5 L), dried over sodium sulfate, filtered and concentrated to give a yellow oil (614 g, yield 90%). The crude (1R,4R,5S,6R)-4,5,6-tris(benzyloxy)-3-(benzyloxymethyl)-1-(4-chloro-3-(4-ethylbenzyl)phenyl)cyclohex-2-enol was used directly in the next step. MS (ESI$^+$) (m/z): 782 (M+18)$^+$, 787 (M+23)$^+$.

(4) Preparation of ((1R,2S,3S,6R)-6-benzyloxymethyl)-4-(4-chloro-3-(4-ethylbenzyl)phenyl)cyclohex-4-ene-1,2,3-triyl)tris(oxy)tris(methylene)tribenzene

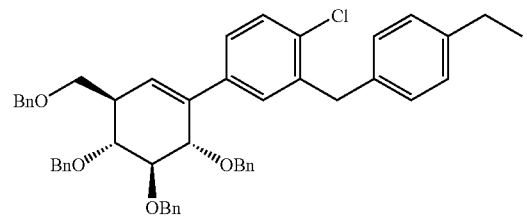

Triethylsilane (167.9 g, 229.7 mL, 1.446 mol, 2 eq) and boron-trifluoride etherate (205.2 g, 204.1 mL, 1.446 mol, 2 eq) were successively added into a solution of (1R,4R,5S, 6R)-4,5,6-tris(benzyloxy)-3-(benzyloxymethyl)-1-(4-chloro-3-(4-ethylbenzyl)phenyl)cyclohex-2-enol (614.0 g, crude, ~0.723 mol, 1 eq) in methylene chloride (2.6 L) under argon at −20° C. and the mixture stirred over 1 h at −20° C. Ammonium chloride (aq. sat., 100 mL) was added and the mixture was extracted with methylene chloride (3×1 L), the organic layer was washed with brine (3×0.5 L), dried over sodium sulfate, filtered and concentrated. The residue was purified by recrystallization in refluxing anhydrous ethanol/isopropyl ether to give a white solid (513 g, purity of 95%, yield 95%).

(5) Preparation of (1R,2S,3R,4R,5S,6R)-3,4,5-tris(benzyloxy)-2-(benzyloxymethyl)-6-(4-chloro-3-(4-ethylbenzyl)phenyl)cyclohexanol

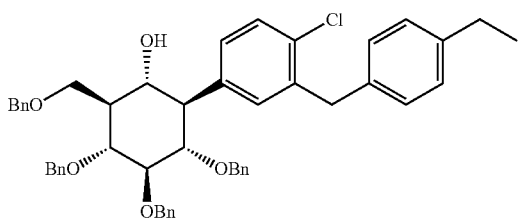

Borane-tetrahydrofuran complex (1M in tetrahydrofuran) (1.31 L, 1.302 mol, 2 eq.) was added into the solution of ((1R,2S,3S,6R)-6-Benzyloxymethyl)-4-(4-chloro-3-(4-ethylbenzyl)phenyl)cyclohex-4-ene-1,2,3-triyl)tris(oxy)tris(methylene)tribenzene (513 g, purity of 95%, 0.651 mol, 1 eq) and lithium borohydride (7.1 g, 2 M in tetrahydrofuran, 0.326 mol, 0.5 eq) in anhydrous tetrahydrofuran (5 L) under argon at 0° C. into a high-pressure reaction stainless steel vessel, and the mixture was heated to about 70~80° C. whereupon the pressure in the reactor reached about 2~2.5 atm. The mixture was stirred for 40 min at this temperature. The reaction vessel was cooled to room temperature and the contents were transferred to a three-necked flask and cooled to −20° C. A cold (0° C.) solution of sodium hydroxide (78.1 g, 3 M in water, 1.953 mol, 3 eq) was added, followed by 30% hydrogen peroxide (442.8 g, 438.4 mL, 1.953 mol, 20 eq), and the mixture was allowed to warm to room temperature overnight. The reaction mixture was acidified with 1 N hydrochloric acid to pH 6 and the solvent was removed under reduced pressure. Water (5 L) was added into the residue and extracted with ethyl acetate (3×2 L). The organic layers were washed with brine (3×1 L), dried over sodium sulfate, filtered and concentrated. The residue was purified by recrystallization in ethyl ether/n-hexane (v/v=1:10, 10 mL/g (crude)) to give a white solid (314.7 g, purity of 95%, yield 60%).

(6) Preparation of Crude (1R,2R,3S,4R,5R,6S)-4-(4-chloro-3-(4-ethylbenzyl)phenyl)-6-(hydroxymethyl)cyclohexane-1,2,3,5-tetraol

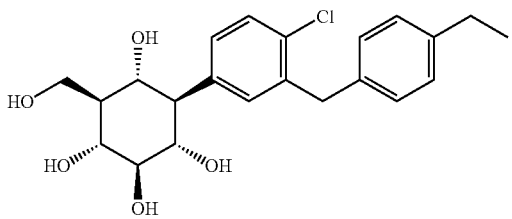

To a solution of (1R,2S,3R,4R,5S,6R)-3,4,5-tris(benzyloxy)-2-(benzyloxymethyl)-6-(4-chloro-3-(4-ethylbenzyl)phenyl)cyclohexanol (60 g, purity of 98%, 0.077 mol, 1 eq) in tetrahydrofuran:methanol (v/v=2:1) (600 mL) was added 1,2-dichlorobenzene (21.5 g, 16.54 mL, 0.82 mol, 2 eq), palladium on carbon (10%, 4.8 g) and was stirred for 4 h under an atmospheric pressure of hydrogen at room temperature (about 25° C.). The mixture was filtered and the filtrate was evaporated to dryness to give a yellow oil (80% pure).

(7) Preparation of (1S,2R,3R,4S,5R,6R)-4-(acetoxymethyl)-6-(4-chloro-3-(4-ethylbenzyl)phenyl)cyclohexane-1,2,3,5-tetrayl tetraacetate (19)

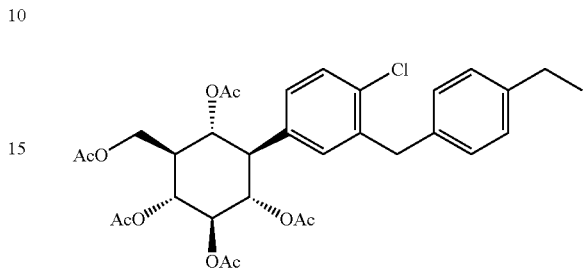

Acetic anhydride (78.8 g, 72.9 mL, 0.77 mol, 10 eq), N,N-diisoproylethylamine (99.5 g, 134.1 mL, 0.77 mol, 10 eq), and 4-dimethylaminopyridine (DMAP, 0.47 g, 3.85 mmol, 0.05 eq) were added slowly to a solution of the above crude oil (1R,2R,3S,4R,5R,6S)-4-(3-(4-ethylbenzyl)-4-chlorophenyl)-6-(hydroxymethyl)cyclohexane-1,2,3,5-tetraol (0.077 mol, purity of 80%) in methylene chloride (300 mL) at 0° C. and the mixture was stirred overnight at room temperature. The mixture was acidified with 1N hydrochloric acid to pH 6 and the organic layer was washed with 1N hydrochloric acid (3×200 mL), dried over sodium sulfate, filtered and concentrated. The residue was recrystallized in boiling ethanol/ethyl acetate (v/v=3:1, 15 mL/g (crude)). The first solids appeared at ~58° C. and the mixture was stirred for 2 h at 58° C. The mixture was allowed to cool to room temperature over 2 h to give a white solid (42.2 g, purity of 99.4%, yield 88.7% in two steps).

(8) Preparation of (1R,2R,3S,4R,5R,6S)-4-(4-chloro-3-(4-ethylbenzyl)phenyl)-6-(hydroxymethyl)cyclohexane-1,2,3,5-tetraol

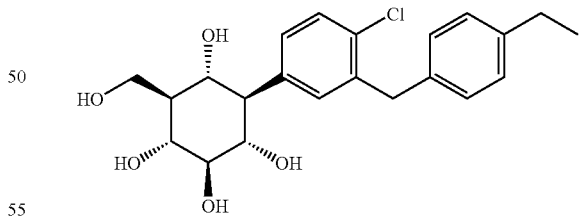

To a stirred solution of (1S,2R,3R,4S,5R,6R)-4-(acetoxymethyl)-6-(4-chloro-3-(4-ethylbenzyl)phenyl)cyclohexane-1,2,3,5-tetrayl tetraacetate (98 g, >99%, 0.158 mol, 1 eq) in methanol (1 L) was added sodium hydroxide (powder, 12.6 g, 0.315 mol, 2 eq) and the mixture was refluxed overnight. The mixture was acidified to pH 6 with 1 N hydrochloric acid and the volatiles were removed under reduced pressure. The residues were dissolved in ethyl acetate (3 L), washed with water (1 L), then with brine (1 L), dried over sodium sulfate, filtered and concentrated to give a white foam. The foam was recrystallized in refluxing ethanol/water (v/v=1:3, 20 mL/g (crude)) twice to give a white solid (58 g, purity of 99.3%, yield 90%).

Example 21

This Example Illustrates the Preparation of 1-(4-(2-chloro-5-((1R,2S,3R,4R,5S,6R)-2,3,4,6-tetrahydroxy-5-(hydroxymethyl)cyclohexyl)benzyl)phenyl)ethanone (39)

Preparation of (1S,2R,3R,4S,5R,6R)-4-(acetoxymethyl)-6-(3-(4-acetylbenzyl)-4-chlorophenyl)cyclohexane-1,2,3,5-tetrayl tetraacetate (38)

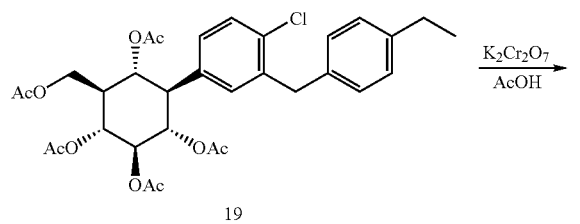

To a vigorously stirred solution of (1S,2R,3R,4S,5R,6R)-4-(acetoxymethyl)-6-(4-chloro-3-(4-ethylbenzyl)phenyl)cyclohexane-1,2,3,5-tetrayl tetraacetate (19) (300 mg, 48.7 µmol) in acetic acid (5 mL) was added $K_2Cr_2O_7$ (172 mg, 0.58 mmol) and the mixture was stirred for 22 hours at 125° C. The mixture was cooled to room temperature, diluted with water (20 mL) and extracted with ethyl acetate (3×20 mL). The combined organic extracts were washed with saturated $NaHCO_3$ (3×10 mL) and then with brine (20 mL), dried ($Na_2SO_4$), filtered and concentrated. Preparative TLC (2:1 hexane:ethyl acetate) afforded 100 mg of the desired compound. MS (ESI$^+$): 631 [M+H]$^+$, 648 [M+H$_2$O]$^+$.

Preparation of 1-(4-(2-chloro-5-((1R,2S,3R,4R,5S,6R)-2,3,4,6-tetrahydroxy-5-(hydroxymethyl)cyclohexyl)benzyl)phenyl)ethanone (39)

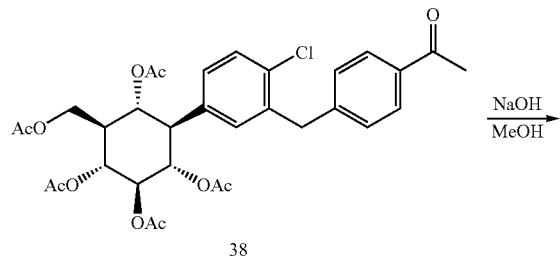

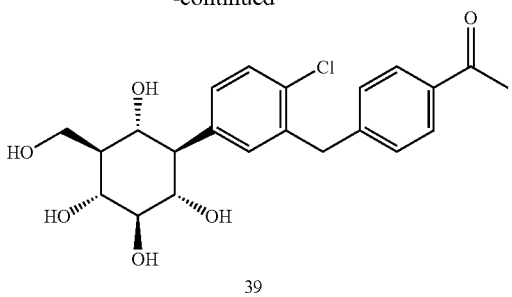

To a solution of (1S,2R,3R,4S,5R,6R)-4-(acetoxymethyl)-6-(3-(4-acetylbenzyl)-4-chlorophenyl)cyclohexane-1,2,3,5-tetrayl tetraacetate (38) (300 mg, 47.6 µmol) in MeOH (5 mL) was added sodium hydroxide (29 mg, 72 µmol) and stirred for 1.5 h under reflux. The mixture was acidified to pH 6 with 1 N hydrochloric acid and the solvents were removed under reduced pressure. The residue was purified by preparative HPLC to provide 30 mg of the desired compound. $^1$H-NMR (400 MHz, CD$_3$OD): δ 7.90 (2H, d, J=8.4 Hz), 7.35 (3H, m), 7.22 (H, d, J=1.6 Hz), 7.18 (1H, d, J=8.4, 1.6 Hz), 4.17 (2H, s), 3.91 (2H, d, J=3.2 Hz), 3.66 (1H, t, J=10.4 Hz), 3.49-3.40 (2H, m), 3.30 (1H, m), 2.57-2.52 (4H, m), 1.55-1.50 (1H, m); MS (ESI$^+$): 421 [M+H]$^+$, 443 [M+Na]$^+$, (ESI$^-$): 465 [M+HCOO]$^-$.

Example 22

Preparation of (1R,2R,3S,4R,5R,6S)-4-(4-chloro-3-(4-(1-hydroxyethyl)benzyl)phenyl)-6-(hydroxymethyl)cyclohexane-1,2,3,5-tetraol (40)

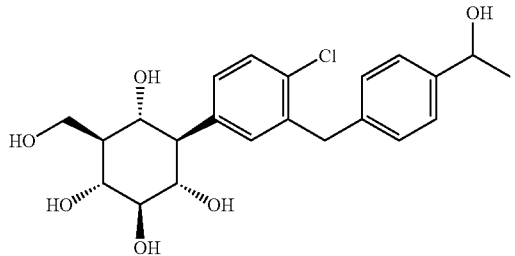

Compound 40 was prepared by reduction of (1S,2R,3R,4S,5R,6R)-4-(acetoxymethyl)-6-(3-(4-acetylbenzyl)-4-chlorophenyl)cyclohexane-1,2,3,5-tetrayl tetraacetate (38) with excess sodium borohydride and purification by preparative HPLC to give 0.6 mg of a clear film. MS (ESI$^+$): 445 [M+Na]$^+$, (ESI$^-$): 467 [M+HCOO]$^-$.

Example 23

The SGLT inhibitory effects of the compounds of the present invention were demonstrated by the following procedures.

Preparation of Human SGLT2 Expression Vector

A full-length cDNA clone expressing human SGLT2 (GenScript Corporation) was subcloned into Hind III and Not I sites of pEAK15 expression vector. Clones harboring the cDNA inserts were identified by restriction analysis.

Preparation of a Cell Line Stably Expressing Human SGLT2

Plasmid containing human SGLT2 was linearized with Nsi I and purified by agarose gel electrophoresis. Using Lipofectamine 2000 Transfection Reagent (Invitrogen Corporation), DNA was transfected into HEK293.ETN cells and cultured in Dulbecco's Modified Eagle Medium (DMEM) containing 10% fetal bovine serum (FBS) at 37° C. under 5% $CO_2$ for 24 h. Transfectants were selected in the same growth medium supplemented with puromycin (Invitrogen Corporation) for two weeks. Puromycin-resistant cells were recovered and seeded on a fresh 96-well plate (single cell per well) and cultured in the presence of puromycin until cells became confluent. Puromycin-resistant clones were evaluated for SGLT2 activity in the methyl-α-D-[U-$^{14}$C]glucopyranoside uptake assay described below. The clone that exhibited the highest signal-to-background ratio was used for the methyl-α-D-[U-$^{14}$C]glucopyranoside uptake assay.

Preparation of Human SGLT1 Expressing Cells

Full-length human SGLT1 cDNA on pDream2.1 expression vector was obtained from GenScript Corporation and propagated in *Escherichia coli* strain DH5α using Luria-Bertani (LB) medium containing ampicillin. Plasmid DNA was isolated using the QIAGEN Plasmid Midi Kit (QIAGEN Inc.). Human SGLT1 expression plasmid DNA was transfected into COS-7 cells (American Type Culture Collection) using Lipofectamine 2000 Transfection Reagent according to a manufacturer suggested protocol. Transfected cells were stored in DMEM containing 10% dimethyl sulfoxide (DMSO) at −80° C.

Methyl-α-D-[U-$^{14}$C]glucopyranoside Uptake Assay

Cells expressing SGLT1 or SGLT2 were seeded on 96-well ScintiPlate scintillating plates (PerkinElmer, Inc.) in DMEM containing 10% FBS (1×10$^5$ cells per well in 100 µl medium) incubated at 37° C. under 5% $CO_2$ for 48 h prior to the assay. Cells were washed twice with 150 µl of either sodium buffer (137 mM NaCl, 5.4 mM KCl, 2.8 mM $CaCl_2$, 1.2 mM $MgCl_2$, 10 mM tris(hydroxymethyl)aminomethane/N-2-hydroxyethylpiperazine-N'-ethanesulfonic acid [Tris/Hepes], pH 7.2) or sodium-free buffer (137 mM N-methyl-glucamine, 5.4 mM KCl, 2.8 mM $CaCl_2$, 1.2 mM $MgCl_2$, 10 mM Tris/Hepes, pH 7.2). Test compound in 50 µl each of sodium or sodium-free buffer containing 40 µCi/ml methyl-α-D-[U-$^{14}$C]glucopyranoside (Amersham Biosciences/GE Healthcare) and 25% human serum was added per well of a 96-well plate and incubated at 37° C. with shaking for either 2 h (SGLT1 assay) or 1.5 h (SGLT2 assay). Cells were washed twice with 150 µl of wash buffer (137 mM N-methylglucamine, 10 mM Tris/Hepes, pH 7.2) and methyl-α-D-[U-$^{14}$C]glucopyranoside uptake was quantitated using a TopCount scintillation counter (PerkinElmer, Inc.). Sodium-dependent glucopyranoside uptake was measured by subtracting the values obtained with sodium-free buffer from those obtained using sodium buffer (average of triplicate determinations).

TABLE 1

| Compound | $IC_{50}$* SGLT2 | SGLT1 |
|---|---|---|
| 5 (R = Et) | + | + |
| 9 | + | ++ |
| 10 | + | + |
| 11 | + | ++ |
| 12 | + | +++ |
| 13 | + | +++ |
| 17 | + | ++ |
| 30 | + | +++ |
| 35 | + | ++ |
| 37 | + | ++ |
| 39 | + | ++ |
| 40 | + | ++ |

*Key:
+ <1 µM
++ 1 µM to 10 µM
+++ >10 µM

What is claimed is:

1. A compound of Formula I:

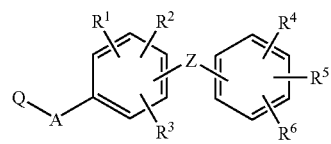

wherein

A is selected from the group consisting of oxygen and a single bond;

Q is selected from the group consisting of formulae $Q^1$ to $Q^4$;

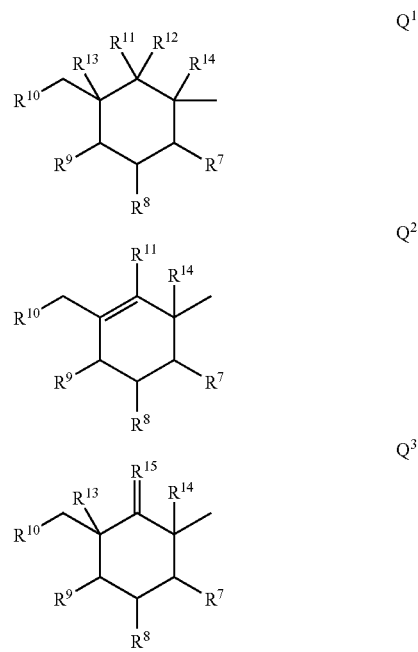

$$Q^4$$

(structure with R¹¹, R¹³, R¹⁰, R⁹, R⁸, R⁷ on cyclohexene ring)

Z is methylene optionally substituted with one to two substituents independently selected from halo, hydroxy, $C_1$-$C_6$ alkyl, $C_1$-$C_6$ alkoxy, $C_3$-$C_6$ cycloalkyl and $C_3$-$C_6$ cycloalkyloxy;

$R^1$, $R^2$ and $R^3$ are each independently selected from the group consisting of hydrogen, halo, hydroxy, $C_1$-$C_6$ alkyl, $C_2$-$C_6$ alkenyl, $C_2$-$C_6$ alkynyl, $C_3$-$C_{10}$ cycloalkyl, $C_5$-$C_{10}$ cycloalkenyl, $C_1$-$C_6$ alkyloxy, $C_3$-$C_{10}$ cycloalkyloxy, cyano, amino and nitro, wherein alkyl, alkenyl, alkynyl, cycloalkyl and cycloalkenyl groups or portions are optionally partly or completely fluorinated and are optionally mono- or disubstituted by identical or different substituents selected from the group consisting of chlorine, hydroxy, $C_1$-$C_3$ alkoxy and $C_1$-$C_3$ alkyl, and in cycloalkyl and cycloalkenyl groups or portions one or two methylene groups are optionally replaced independently of one another by $NR^a$, O, S, CO, SO or $SO_2$, and one or two methyne groups are optionally replaced by N, or in the event that $R^1$ and $R^2$ are bound to two adjacent C atoms of the phenyl ring, $R^1$ and $R^2$ are optionally joined together to form a $C_{3\text{-}5}$ alkylene, $C_{3\text{-}5}$ alkenylene or butadienylene bridge, which is optionally partly or completely fluorinated and is optionally mono- or disubstituted by identical or different substituents selected from chlorine, hydroxy, $C_1$-$C_3$ alkoxy and $C_1$-$C_3$ alkyl, and wherein one or two methylene groups are optionally replaced independently of one another by O, S, CO, SO, $SO_2$ or $NR^a$, and wherein one or two methyne groups optionally may be replaced by N;

$R^4$ is a member selected from the group consisting of hydrogen, halo, cyano, nitro, amino, hydroxy, $C_1$-$C_6$ alkyl, $C_2$-$C_6$ alkenyl, $C_2$-$C_6$ alkynyl, $C_3$-$C_{10}$ cycloalkyl, $C_5$-$C_{10}$ cycloalkenyl, $C_1$-$C_6$ alkyloxy, $C_3$-$C_{10}$ cycloalkyloxy, ($C_1$-$C_6$ alkyloxy)$C_1$-$C_6$ alkyloxy, $C_5$-$C_7$ cycloalkenyloxy, aryl, heteroaryl, aryloxy, heteroaryloxy, ($C_2$-$C_4$ alkenyl)$C_1$-$C_3$ alkyloxy, ($C_2$-$C_4$ alkynyl)$C_1$-$C_3$ alkyloxy, (aryl)$C_1$-$C_3$ alkyloxy, (heteroaryl)$C_1$-$C_3$ alkyloxy, ($C_3$-$C_{10}$ cycloalkyl)$C_1$-$C_3$ alkyl, ($C_3$-$C_{10}$ cycloalkyl)$C_1$-$C_3$ alkyloxy, ($C_5$-$C_{10}$ cycloalkenyl)$C_1$-$C_3$ alkyl, ($C_5$-$C_{10}$ cycloalkenyl)$C_1$-$C_3$ alkyloxy, ($C_1$-$C_4$ alkyloxy)$C_1$-$C_3$ alkyl, ($C_3$-$C_7$ cycloalkyloxy)$C_1$-$C_3$ alkyl, ($C_3$-$C_7$ cycloalkyloxy)$C_2$-$C_4$ alkenyl, ($C_3$-$C_7$ cycloalkyloxy)$C_2$-$C_4$ alkynyl, ($C_3$-$C_7$ cycloalkyloxy)$C_1$-$C_3$ alkyloxy, ($C_1$-$C_4$ alkylamino)$C_1$-$C_3$ alkyl, di-($C_1$-$C_3$ alkylamino)$C_1$-$C_3$ alkyl, tri-($C_1$-$C_4$ alkyl)silyl-$C_1$-$C_6$ alkyl, tri-($C_1$-$C_4$ alkyl)silyl-$C_2$-$C_6$ alkenyl, tri-($C_1$-$C_4$ alkyl)silyl-$C_2$-$C_6$ alkynyl, tri-($C_1$-$C_4$ alkyl)silyl-$C_1$-$C_6$ alkyloxy, ($C_3$-$C_7$ cycloalkyl)$C_2$-$C_5$ alkenyl, ($C_3$-$C_7$ cycloalkyl)$C_3$-$C_5$ alkenyloxy, ($C_3$-$C_7$ cycloalkyl)$C_{3\text{-}5}$ alkynyloxy, ($C_5$-$C_8$ cycloalkenyl)$C_3$-$C_5$ alkenyloxy, ($C_5$-$C_8$ cycloalkenyl)$C_3$-$C_5$ alkynyloxy, $C_3$-$C_6$ cycloalkylidenmethyl, ($C_1$-$C_4$ alkyl)carbonyl, arylcarbonyl, heteroarylcarbonyl, aminocarbonyl, ($C_1$-$C_4$ alkyl)aminocarbonyl, di-($C_1$-$C_3$ alkyl)aminocarbonyl, hydroxycarbonyl, ($C_1$-$C_4$ alkyloxy)carbonyl, $C_1$-$C_4$ alkylamino, di-($C_1$-$C_3$ alkyl)amino, ($C_1$-$C_4$ alkyl)carbonylamino, arylcarbonylamino, heteroarylcarbonylamino, $C_1$-$C_4$ alkylsulfonylamino, arylsulfonylamino, $C_1$-$C_4$ alkylsulfanyl, $C_1$-$C_4$ alkylsulfinyl, $C_1$-$C_4$ alkylsulfonyl, $C_3$-$C_{10}$ cycloalkylsulfanyl, $C_3$-$C_{10}$ cycloalkylsulfinyl, $C_3$-$C_{10}$ cycloalkylsulfonyl, $C_5$-$C_{10}$ cycloalkenylsulfanyl, $C_5$-$C_{10}$ cycloalkenylsulfinyl, $C_5$-$C_{10}$ cycloalkenylsulfonyl, arylsulfanyl, arylsulfinyl and arylsulfonyl, wherein alkyl, alkenyl, alkynyl, cycloalkyl and cycloalkenyl groups or portions are optionally partly or completely fluorinated and are optionally mono- or disubstituted by identical or different substituents selected from chlorine, hydroxy, $C_1$-$C_3$ alkoxy and $C_1$-$C_3$ alkyl, and in cycloalkyl and cycloalkenyl groups or portions one or two methylene groups are optionally replaced independently of one another by $NR^a$, O, S, CO, SO or $SO_2$, and one or two methyne groups are optionally replaced by N;

$R^5$ and $R^6$ are each independently selected from the group consisting of hydrogen, halo, cyano, nitro, hydroxy, $C_1$-$C_6$ alkyl, $C_2$-$C_6$ alkenyl, $C_2$-$C_6$ alkynyl, $C_3$-$C_{10}$ cycloalkyl, $C_1$-$C_3$ alkyloxy and $C_3$-$C_{10}$ cycloalkyloxy, wherein alkyl, alkenyl, alkynyl, cycloalkyl and cycloalkenyl groups or portions are optionally partly or completely fluorinated and are optionally mono- or disubstituted by identical or different substituents selected from chlorine, hydroxy, $C_1$-$C_3$ alkoxy and $C_1$-$C_3$ alkyl, and in cycloalkyl and cycloalkenyl groups or portions one or two methylene groups are optionally replaced independently of one another by $NR^a$, O, S, CO, SO or $SO_2$, and one or two methyne groups are optionally replaced by N, or if $R^5$ and $R^6$ are bound to two adjacent C atoms of the phenyl ring, $R^5$ and $R^6$ are optionally joined together to form a $C_3$-$C_5$ alkylene, $C_3$-$C_5$ alkenylene or butadienylene bridge, which is optionally partly or completely fluorinated and mono- or disubstituted by identical or different substituents selected from chlorine, hydroxy, $C_1$-$C_3$ alkoxy and $C_1$-$C_3$ alkyl, and wherein one or two methylene groups are optionally replaced independently of one another by O, S, CO, SO, $SO_2$ or $NR^a$, and wherein one or two methyne groups are optionally replaced by N;

$R^7$, $R^8$, $R^9$ and $R^{10}$ are each independently selected from the group consisting of hydroxy, ($C_1$-$C_{18}$ alkyl)carbonyloxy, ($C_1$-$C_{18}$ alkyl)oxycarbonyloxy, arylcarbonyloxy, aryl-($C_1$-$C_3$ alkyl)carbonyloxy, ($C_3$-$C_{10}$ cycloalkyl)carbonyloxy, hydrogen, halo, $C_1$-$C_6$ alkyl, $C_2$-$C_6$ alkenyl, $C_2$-$C_6$ alkynyl, ($C_3$-$C_{10}$ cycloalkyl)$C_1$-$C_3$ alkyl, ($C_5$-$C_7$ cycloalkenyl)$C_1$-$C_3$ alkyl, (aryl)$C_1$-$C_3$ alkyl, (heteroaryl)$C_1$-$C_3$ alkyl, $C_1$-$C_6$ alkyloxy, $C_2$-$C_6$ alkenyloxy, $C_2$-$C_6$ alkynyloxy, $C_3$-$C_7$ cycloalkyloxy, $C_5$-$C_7$ cycloalkenyloxy, aryloxy, heteroaryloxy, ($C_3$-$C_7$ cycloalkyl)$C_1$-$C_3$ alkyloxy, ($C_5$-$C_7$ cycloalkenyl)$C_1$-$C_3$ alkyloxy, (aryl)$C_1$-$C_3$ alkyloxy, (heteroaryl)$C_1$-$C_3$ alkyloxy, aminocarbonyl, hydroxycarbonyl, ($C_1$-$C_4$ alkyl)aminocarbonyl, di-($C_1$-$C_3$ alkyl)aminocarbonyl, ($C_1$-$C_4$ alkyloxy)carbonyl, (aminocarbonyl)$C_1$-$C_3$ alkyl, ($C_1$-$C_4$ alkyl)aminocarbonyl-($C_1$-$C_3$)alkyl, di-($C_1$-$C_3$ alkyl)aminocarbonyl-($C_1$-$C_3$)alkyl, (hydroxycarbonyl)$C_1$-$C_3$ alkyl, ($C_1$-$C_4$ alkyloxy)carbonyl-($C_1$-$C_3$)alkyl, ($C_3$-$C_7$ cycloalkyloxy)$C_1$-$C_3$ alkyl, ($C_5$-$C_7$ cycloalkenyloxy)$C_1$-$C_3$ alkyl, (aryloxy)$C_1$-$C_3$ alkyl, (heteroaryloxy)$C_1$-$C_3$ alkyl, $C_1$-$C_4$ alkylsulfonyloxy, arylsulfonyloxy, (aryl)$C_1$-$C_3$ alkylsulfonyloxy, trimethylsilyloxy, t-butyldimethylsilyloxy, and cyano; wherein alkyl, alkenyl, alkynyl, cycloalkyl and cycloalkenyl groups or portions are optionally partly or completely fluorinated and are optionally mono- or disubstituted by identical or different substituents selected from chlorine, hydroxy, $C_1$-$C_3$ alkoxy and $C_1$-$C_3$ alkyl, and in cycloalkyl and cycloalkenyl groups or portions one or two methylene groups are optionally replaced independently of one another by $NR^a$, O, S, CO, SO or $SO_2$;

and optionally, $R^{10}$ and $R^{11}$ can be combined with the carbon atoms to which each is attached to form a five- to seven-membered fused cycloalkane or cycloalkene ring that is optionally partly or completely fluorinated and may be mono- or disubstituted by identical or different substituents selected from chlorine, hydroxy, $C_1$-$C_3$ alkoxy and $C_1$-$C_3$ alkyl, and wherein in the cycloalkyl and cycloalkenyl rings one or two methylene groups are optionally replaced independently of one another by $NR^a$, O, S, CO, SO or $SO_2$;

$R^{11}$ is selected from the group consisting of hydroxy, halo, $C_1$-$C_6$ alkyl, $C_2$-$C_6$ alkenyl, $C_2$-$C_6$ alkynyl, $C_3$-$C_{10}$ cycloalkyl, $C_1$-$C_6$ alkyloxy, $C_2$-$C_6$ alkenyloxy, $C_2$-$C_6$ alkynyloxy or $C_3$-$C_6$ cycloalkyloxy, wherein alkyl, alkenyl, alkynyl and cycloalkyl groups or portions are optionally partly or completely fluorinated, and $R^{12}$ is hydrogen; or $R^{11}$ and $R^{12}$ are optionally joined together with the carbon atom to which they are attached to form a $C_3$-$C_7$ spirocycloalkane ring which is optionally partly or completely fluorinated and is optionally mono- or disubstituted by identical or different substituents selected from chlorine, hydroxy, $C_1$-$C_3$ alkoxy and $C_1$-$C_3$ alkyl;

$R^{13}$ and $R^{14}$ each independently selected from the group consisting of hydrogen, hydroxy, halo, $C_1$-$C_6$ alkyl, $C_2$-$C_6$ alkenyl, $C_2$-$C_6$ alkynyl, $C_3$-$C_{10}$ cycloalkyl, $C_1$-$C_6$ alkyloxy, $C_2$-$C_6$ alkenyloxy, $C_2$-$C_6$ alkynyloxy and $C_3$-$C_6$ cycloalkyloxy, wherein alkyl, alkenyl, alkynyl and cycloalkyl groups or portions are optionally partly or completely fluorinated;

$R^{15}$ is selected from the group consisting of oxygen and $CR^bR^c$;

each $R^a$ independently is selected from the group consisting of hydrogen, $C_1$-$C_4$ alkyl and ($C_1$-$C_4$ alkyl)carbonyl, wherein alkyl groups or portions are optionally partly or completely fluorinated; and $R^b$ and $R^c$ are each independently selected from the group consisting of hydrogen, halo and $C_1$-$C_4$ alkyl, wherein alkyl groups are optionally partly or completely fluorinated;

and pharmaceutically acceptable salts thereof.

2. A compound of claim 1, wherein A is a single bond.

3. A compound of claim 1, wherein Z is $CH_2$.

4. A compound of claim 1, wherein $R^1$, $R^2$ and $R^3$ are each independently selected from the group consisting of hydrogen, halo, hydroxy, $C_1$-$C_6$ alkyl, $C_2$-$C_6$ alkenyl, $C_2$-$C_6$ alkynyl, $C_3$-$C_{10}$ cycloalkyl, $C_1$-$C_6$ alkyloxy, and cyano.

5. A compound of claim 4, wherein $R^1$, $R^2$ and $R^3$ are each independently selected from the group consisting of hydrogen, halo and $C_1$-$C_6$ alkyl.

6. A compound of claim 4, wherein $R^1$ is selected from the group consisting of hydrogen, halo and $C_1$-$C_6$ alkyl, and $R^2$ and $R^3$ are each hydrogen.

7. A compound of claim 1, wherein $R^4$ is selected from the group consisting of $C_1$-$C_6$ alkyl, $C_2$-$C_6$ alkenyl, $C_2$-$C_6$ alkynyl, $C_3$-$C_{10}$ cycloalkyl, $C_1$-$C_6$ alkyloxy, $C_3$-$C_{10}$ cycloalkyloxy, ($C_3$-$C_{10}$ cycloalkyl)$C_1$-$C_3$ alkyloxy, ($C_3$-$C_7$ cycloalkyl)$C_{3-5}$ alkenyloxy, and ($C_3$-$C_7$ cycloalkyl)$C_{3-5}$ alkynyloxy.

8. A compound of claim 1, wherein $R^5$ and $R^6$ are each independently selected from the group consisting of hydrogen, halo, hydroxy, $C_1$-$C_6$ alkyl, $C_2$-$C_6$ alkenyl, $C_2$-$C_6$ alkynyl, $C_3$-$C_{10}$ cycloalkyl, $C_1$-$C_6$ alkyloxy, and cyano.

9. A compound of claim 8, wherein $R^5$ and $R^6$ are each independently selected from the group consisting of hydrogen, halo and $C_1$-$C_6$ alkyl.

10. A compound of claim 9, wherein $R^5$ and $R^6$ are each hydrogen.

11. A compound of claim 1, wherein $R^7$, $R^8$, $R^9$ and $R^{10}$ are each independently selected from the group consisting of hydroxy, halo, $C_1$-$C_6$ alkyl, $C_1$-$C_6$ alkyloxy, ($C_3$-$C_7$)cycloalkyloxy, aryloxy and ($C_3$-$C_7$)cycloalkyl-($C_1$-$C_3$)alkyloxy, wherein alkyl and cycloalkyl groups or portions are optionally partly or completely fluorinated.

12. A compound of claim 11, wherein $R^7$, $R^8$, $R^9$ and $R^{10}$ are each hydroxy.

13. A compound of claim 1, wherein $R^{11}$ is hydroxy.

14. A compound of claim 1, having Formula IA:

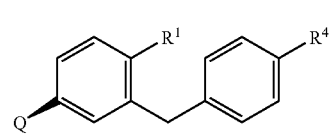

wherein $R^1$ is a member selected from the group consisting of hydrogen, halo and $C_1$-$C_6$ alkyl;

$R^4$ is a member selected from the group consisting of $C_1$-$C_6$ alkyl, $C_2$-$C_6$ alkenyl, $C_2$-$C_6$ alkynyl, $C_3$-$C_{10}$ cycloalkyl, $C_1$-$C_6$ alkyloxy, $C_3$-$C_{10}$ cycloalkyloxy, ($C_3$-$C_{10}$ cycloalkyl)$C_1$-$C_3$ alkyloxy, ($C_3$-$C_7$ cycloalkyl)$C_{3-5}$ alkenyloxy, and ($C_3$-$C_7$ cycloalkyl)$C_{3-5}$ alkynyloxy; and Q is a member selected from formulae $Q^{1A}$ to $Q^{4A}$:

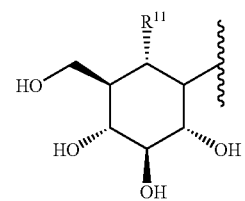

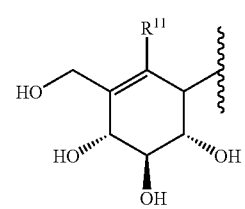

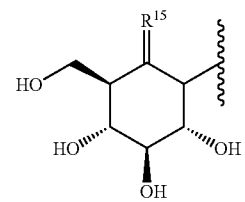

-continued $Q^{4,4}$

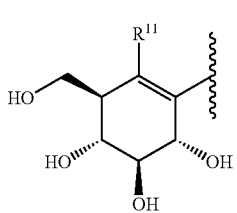

wherein
$R^{11}$ is hydroxy; and
$R^{15}$ is a member selected from the group consisting of oxygen and $CR^bR^c$, wherein $R^b$ and $R^c$ each independently is a member selected from the group consisting of hydrogen and halo.

15. A compound of claim 14, wherein Q is a member selected from the group consisting of $Q^{1,4}$ and $Q^{3,4}$.

16. A compound of claim 1, selected from the group consisting of
(1R,2R,3S,4R,5R,6S)-4-(4-chloro-3-(4-ethylbenzyl)phenyl)-6-(hydroxymethyl)cyclohexane-1,2,3,5-tetraol;
(1R,2R,3S,4R,5R,6S)-4-(4-chloro-3-(4-ethylbenzyl)phenyl)-6-(hydroxymethyl)cyclohexane-1,2,3,5-tetraol;
(1R,2R,3S,4R,5R,6S)-4-(4-chloro-3-(4-cyclopropylbenzyl)phenyl)-6-(hydroxymethyl)cyclohexane-1,2,3,5-tetraol;
(1R,2R,3S,4R,5R,6S)-4-(4-chloro-3-(4-propylbenzyl) phenyl)-6-(hydroxymethyl)cyclohexane-1,2,3,5-tetraol;
(1R,2R,3S,4R,5R,6S)-4-(4-chloro-3-(4-cyclohexylbenzyl)phenyl)-6-(hydroxymethyl)cyclohexane-1,2,3,5-tetraol;
((1S,2R,3R,4S,5R,6R)-3-(4-chloro-3-(4-ethylbenzyl) phenyl)-2,4,5,6-tetrahydroxycyclohexyl)methyl acetate;
(1R,2S,3R,4R,5S,6R)-4-(2-(4-ethylbenzyl)phenoxy)-6-(hydroxymethyl)cyclohexane-1,2,3,5-tetraol;
(1R,2R,3S,4S,6R)-4-(4-chloro-3-(4-ethylbenzyl)phenyl)-6-(hydroxymethyl)-5-methylenecyclohexane-1,2,3-triol;
(4S,5S,6R,7R,8R)-4-(4-chloro-3-(4-ethylbenzyl)phenyl)-8-(hydroxymethyl)spiro[2.5]octane-5,6,7-triol;
1-(4-(2-chloro-5-((1R,2S,3R,4R,5S,6R)-2,3,4,6-tetrahydroxy-5-(hydroxymethyl)cyclohexyl)benzyl)phenyl) ethanone; and
(1R,2R,3S,4R,5R,6S)-4-(4-chloro-3-(4-(1-hydroxyethypbenzyl)phenyl)-6-(hydroxymethypcyclohexane-1,2,3,5-tetraol.

17. A compound of claim 1 which is isotopically labeled.

18. A pharmaceutical composition comprising a pharmaceutically acceptable carrier and a compound of claim 1.

19. A method of treating a disease or condition mediated by SGLT, said method comprising administering to a subject in need thereof a therapeutically effective amount of a compound of claim 1.

20. A method of treating diabetes, said method comprising administering to a subject in need thereof a therapeutically effective amount of a compound of claim 1.

21. A method in accordance with claim 20, wherein said diabetes is type 1 diabetes.

22. A method in accordance with claim 20, wherein said diabetes is type 2 diabetes.

23. A method in accordance with claim 20, wherein said compound is administered in combination with a therapeutic agent selected from the group consisting of antidiabetic agents, lipid-lowering/lipid-modulating agents, agents for treating diabetic complications, anti-obesity agents, antihypertensive agents, antihyperuricemic agents, and agents for treating chronic heart failure or atherosclerosis.

24. A method in accordance with claim 19, wherein said disease or condition is selected from the group consisting of type 1 diabetes mellitus, type 2 diabetes mellitus, hyperglycemia, diabetic complications, insulin resistance, metabolic syndrome, hyperinsulinemia, hypertension, hyperuricemia, obesity, edema, dyslipidemia, chronic heart failure, and atherosclerosis.

25. A compound of the formula:

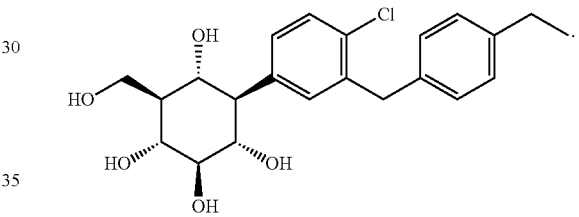

26. A method of treating a disease or condition mediated by SGLT, wherein said disease or condition is selected from the group consisting of type 1 diabetes mellitus, type 2 diabetes mellitus, hyperglycemia, diabetic complications, insulin resistance, metabolic syndrome, hyperinsulinemia, hypertension, hyperuricemia, obesity, edema, dyslipidemia, chronic heart failure and atherosclerosis, said method comprising administering to a subject in need thereof a therapeutically effective amount of a compound of claim 25.

27. A method of treating diabetes, said method comprising administering to a subject in need thereof a therapeutically effective amount of a compound of claim 25.

28. A pharmaceutical composition comprising a pharmaceutically acceptable carrier and a compound of claim 25.

* * * * *

UNITED STATES PATENT AND TRADEMARK OFFICE
CERTIFICATE OF CORRECTION

PATENT NO. : 8,129,434 B2
APPLICATION NO. : 12/333190
DATED : March 6, 2012
INVENTOR(S) : Chen et al.

Page 1 of 1

It is certified that error appears in the above-identified patent and that said Letters Patent is hereby corrected as shown below:

On the Title Page:

In the References Cited section, item (56), page 2, first column, line 13, under the FOREIGN PATENT DOCUMENTS subsection: please delete "WO 01/27128" and insert --WO 01/027128--.

In the References Cited section, item (56), page 2, first column, line 14, under the FOREIGN PATENT DOCUMENTS subsection: please delete "WO 01/74834" and insert --WO 01/074834--.

In the References Cited section, item (56), page 2, first column, line 15, under the FOREIGN PATENT DOCUMENTS subsection: please delete "WO 01/74835" and insert --WO 01/074835--.

In the Claims:

Claim 1, Column 53, Line 52: please delete "alkyloxy)C $_1$-C$_3$" and insert --alkyloxy)C$_1$-C$_3$--.

Claim 16, Column 57, Lines 48-49: please delete "(1R,2R,3S,4R,5R,6S)-4-(4-chloro-3-(4-(1-hydroxyethypbenzyl)phenyl)-6-(hydroxymethypcyclohexane-1,2,3,5-tetraol" and insert --(1R,2R,3S,4R,5R,6S)-4-(4-chloro-3-(4-(1-hydroxyethyl)benzyl)phenyl)-6-(hydroxymethyl)cyclohexane-1,2,3,5-tetraol--.

Signed and Sealed this
Tenth Day of July, 2012

David J. Kappos
*Director of the United States Patent and Trademark Office*